(12) United States Patent
Kawamura et al.

(10) Patent No.: US 7,833,632 B2
(45) Date of Patent: Nov. 16, 2010

(54) NITROGENOUS HETEROCYCLE DERIVATIVE, AND ORGANIC ELECTROLUMINESCENT ELEMENT EMPLOYING THE SAME

(75) Inventors: Masahiro Kawamura, Sodegaura (JP); Hiroshi Yamamoto, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1008 days.

(21) Appl. No.: 10/594,323

(22) PCT Filed: Apr. 4, 2005

(86) PCT No.: PCT/JP2005/006605

§ 371 (c)(1),
(2), (4) Date: Sep. 27, 2006

(87) PCT Pub. No.: WO2005/097756

PCT Pub. Date: Oct. 20, 2005

(65) Prior Publication Data

US 2007/0200490 A1 Aug. 30, 2007

(30) Foreign Application Priority Data

Apr. 7, 2004 (JP) ............................. 2004-112799

(51) Int. Cl.
*C07D 403/02* (2006.01)
(52) U.S. Cl. ...................... 428/690; 313/504; 548/305.1
(58) Field of Classification Search ........................ None
See application file for complete search history.

(56) References Cited

U.S. PATENT DOCUMENTS

2006/0147747 A1 * 7/2006 Yamamoto et al. .......... 428/690

FOREIGN PATENT DOCUMENTS

| JP | 2002 47274 | 2/2002 |
|---|---|---|
| WO | 03 060956 | 7/2003 |
| WO | WO 03/060956 A2 * | 7/2003 |
| WO | 2004 080975 | 9/2004 |

OTHER PUBLICATIONS

U.S. Appl. No. 11/722,609, issued Jun. 22, 2007, Kawamura, et al.

\* cited by examiner

*Primary Examiner*—D. Lawrence Tarazano
*Assistant Examiner*—Gregory Clark
(74) *Attorney, Agent, or Firm*—Oblon, Spivak, McClelland, Maier & Neustadt, L.L.P.

(57) ABSTRACT

Provided is a material for an organic EL device realizing an organic EL device capable of having a high current efficiency even at a low voltage. Provided is a derivative of heterocyclic compound having a nitrogen atom represented by the following general formula (A-1) or (A-2). In the formulae, $R^{1a}$ to $R^{5a}$ each represent a substituent, $Ar^{1a}$ to $Ar^{3a}$ each represent a single bond or a divalent connecting group, and HAr represents a group represented by a general formula (A-3) or (A-4). $R^{6a}$ to $R^{10a}$ each represent a substituent.

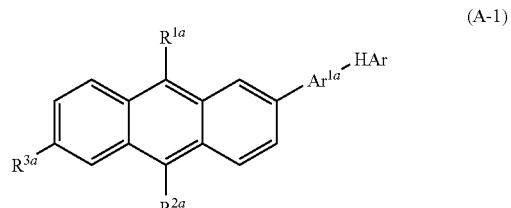

(A-1)

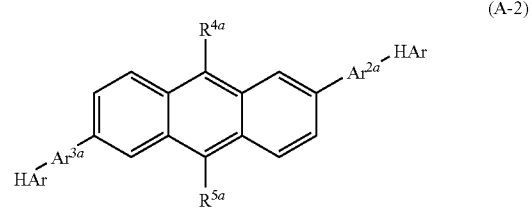

(A-2)

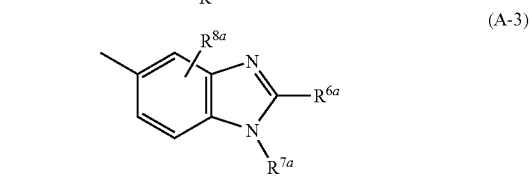

(A-3)

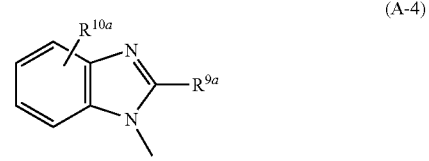

(A-4)

21 Claims, No Drawings

NITROGENOUS HETEROCYCLE DERIVATIVE, AND ORGANIC ELECTROLUMINESCENT ELEMENT EMPLOYING THE SAME

TECHNICAL FIELD

The present invention relates to a novel compound and an organic electroluminescence device capable of having a high efficiency of light emission at a low voltage.

BACKGROUND ART

An organic electroluminescence device using an organic substance (hereinafter, electroluminescence may be abbreviated as EL) has a potential to find use in an application as a thin, inexpensive, large-screen, full-color display device, and a large number of such devices have been developed. In general, an organic EL device is a spontaneous light-emitting device utilizing a principle in which an electric field is applied so that an organic substance emits light owing to the recombination energy between a hole injected from an anode and an electron injected from a cathode.

A conventional organic EL device has a higher driving voltage, a lower emission luminance, and a lower efficiency of light emission that those of an inorganic light-emitting diode. Although a recent organic EL device is gradually improved, an increased emission luminance and an increased efficiency of light emission at a low voltage have been requested.

For example, a blue light-emitting device using a benzimidazole derivative as an electron-transmitting material has been disclosed as means for emitting light at a high emission luminance and a high efficiency of light emission at a low voltage (see, for example, Patent Document 1 below). In this invention, a compound represented by the following formula (a) is used as an electron-transmitting layer, so blue light emission having an emission luminance of 537 cd/m$^2$ and a efficiency of light emission of 2.69 cd/A at a current density of 20 mA/m$^2$ is obtained. In addition, a compound represented by the following formula (b) having a benzimidazole ring and an anthracene skeleton has been disclosed (see, for example, Patent Document 2 below). However, an organic EL device using any one of those compounds does not have a sufficient efficiency of light emission, so an additional improvement in efficiency of light emission has been desired.

(a)

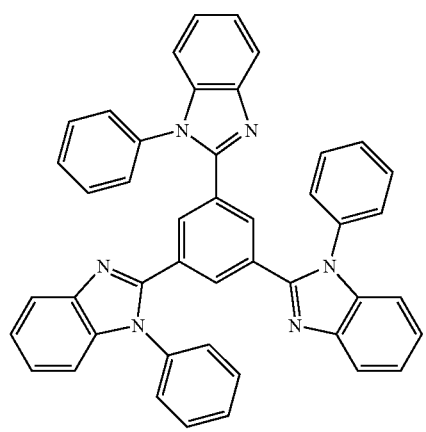

-continued (b)

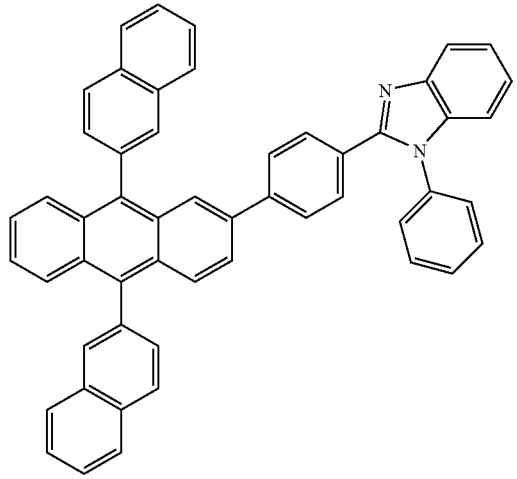

Patent Document 1: JP-A-10-106749
Patent Document 2: WO 03/060956

DISCLOSURE OF THE INVENTION

The present invention has been made in view of the above circumstances, and an object of the present invention is to provide an organic EL device capable of having a high efficiency of light emission even at a low voltage and a material for an organic EL device for realizing the above-mentioned device.

The inventors of the present invention have made extensive studies with a view to achieving the above object. As a result, they have found that the use of a specific derivative of heterocyclic compound having a nitrogen atom as a material for an organic EL device achieves the above object. The present invention has been completed on the basis of such finding.

That is, the present invention provides the following derivative of heterocyclic compound having a nitrogen atom and organic electroluminescence device.

1. A derivative of heterocyclic compound having a nitrogen atom represented by the following general formula (A-1) or (A-2).

(A-1)

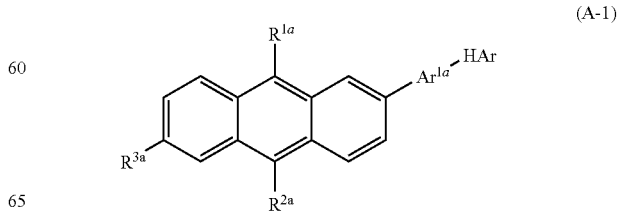

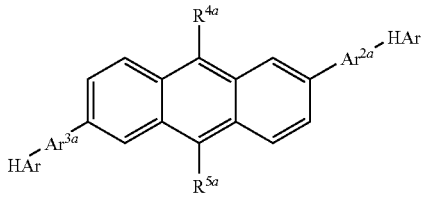

(A-2)

In the formulae, $R^{1a}$ to $R^{5a}$ each represent a substituent, $Ar^{1a}$ to $Ar^{3a}$ each represent a single bond or a divalent connecting group, and HAr represents a group represented by the following general formula (A-3) or (A-4).

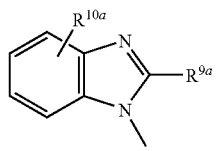

(A-3)

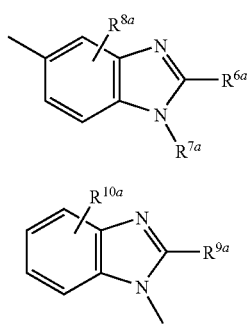

(A-4)

In the formulae, $R^{6a}$ to $R^{10a}$ each represent a substituent.

2. A derivative of heterocyclic compound having a nitrogen atom according to the above item 1, in which the derivative of heterocyclic compound having a nitrogen atom represented by the general formula (A-1) is represented by the following general formula (1-I) or (1-II).

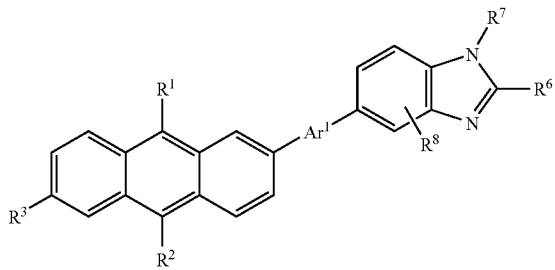

(1-I)

(1-II)

In the formulae, $R^1$ and $R^2$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^1$ and $R^2$ cannot simultaneously represent hydrogen atoms; $R^3$ represents any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; and $Ar^1$ represents a group selected from a substituted or unsubstituted arylene group, a substituted or unsubstituted heteroarylene group, and a substituted or unsubstituted divalent aliphatic hydrocarbon group.

3. A derivative of heterocyclic compound having a nitrogen atom according to the above item 1, wherein the derivative of heterocyclic compound having a nitrogen atom represented by the general formula (A-2) is represented by the following general formula (2-I) or (2-II).

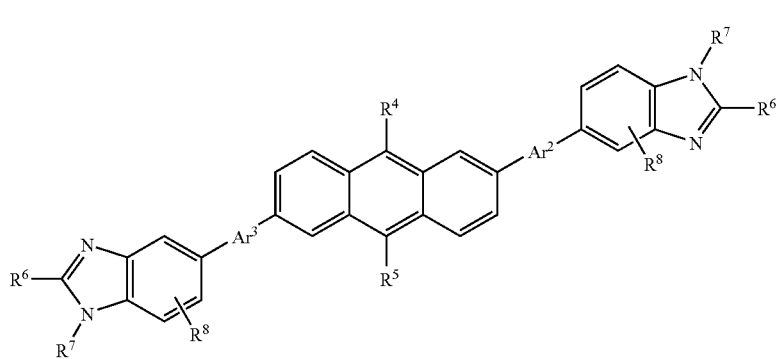

(2-I)

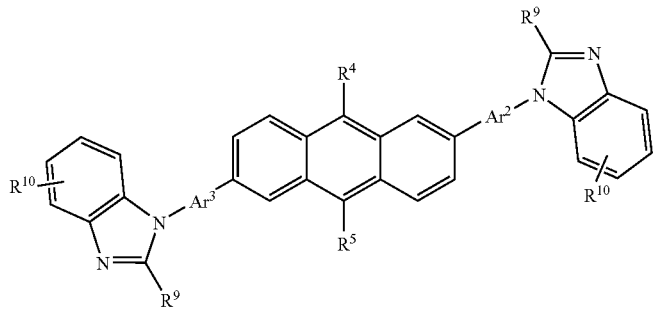

In the formulae, $R^4$ and $R^5$ each represent the same as that represented by $R^1$ and $R^2$; $R^6$, $R^7$, $R^8$, and $R^9$ each represent the same as described above; $Ar^2$ and $Ar^3$ each independently represent the same group as that of $Ar^1$.

4. A derivative of heterocyclic compound having a nitrogen atom according to the above item 1, in which the derivative of heterocyclic compound having a nitrogen atom represented by the general formula (A-1) is represented by the following general formula (3-I) or (3-II).

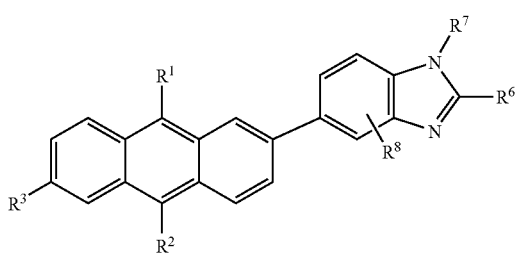

(3-I)

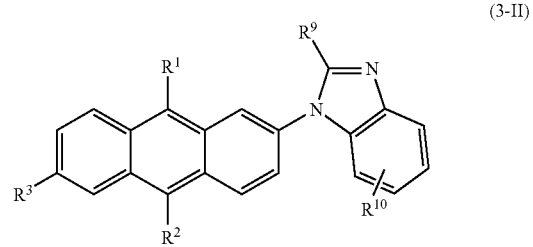

(3-II)

In the formulae, $R^1$, $R^2$, $R^3$, $R^6$, $R^7$, $R^8$, $R^9$, and $R^{10}$ each represent the same as described above.

5. A derivative of heterocyclic compound having a nitrogen atom according to the above item 1, in which the derivative of heterocyclic compound having a nitrogen atom represented by the general formula (A-2) is represented by the following general formula (4-I) or (4-II).

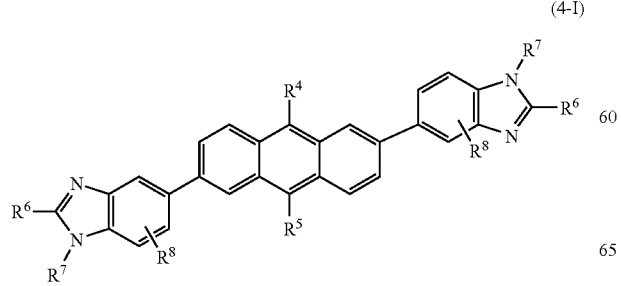

(4-I)

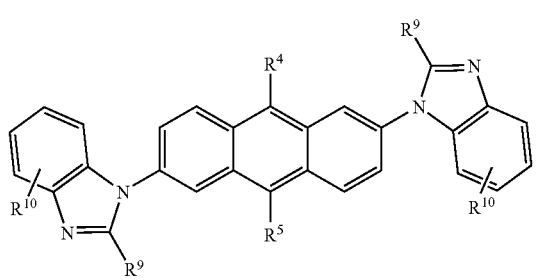

(4-II)

In the formulae, $R^4$, $R^5$, $R^6$, $R^7$, $R^8$, $R^9$, and $R^{10}$ each represent the same as described above.

6. A derivative of heterocyclic compound having a nitrogen atom according to the above item 1, in which the derivative of heterocyclic compound having a nitrogen atom represented by the general formula (A-2) is represented by the following general formula (5-I) or (5-II).

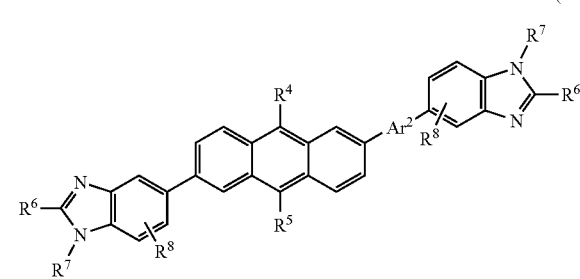

(5-I)

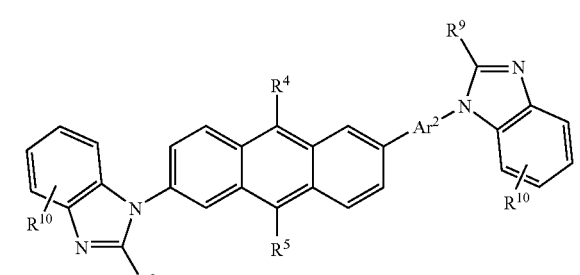

(5-II)

In the formulae, $R^4$, $R^5$, $R^6$, $R^7$, $R^8$, $R^9$, $R^{10}$ and $Ar^2$ each represent the same as described above.

7. A derivative of heterocyclic compound having a nitrogen atom according to the above item 1, in which $R^{7a}$ in the general formula (A-3) represents a substituted or unsubstituted aliphatic hydrocarbon group, or $Ar^{1a}$ to $Ar^{3a}$ in the general formulae (A-1) and (A-2) each represent a substituted or unsubstituted divalent aliphatic hydrocarbon group.

8. A derivative of heterocyclic compound having a nitrogen atom according to any one of the above items 2 to 6, in which, $R^7$ in the general formula (1-I), (2-I), (3-I), (4-I), or (5-I) represents a substituted or unsubstituted aliphatic hydrocarbon group, or $Ar^1$ to $Ar^3$ in the general formula (1-I), (2-I), (3-I), (4-I), or (5-I) each represent a substituted or unsubstituted divalent aliphatic hydrocarbon group.

9. A derivative of heterocyclic compound having a nitrogen atom according to any one of the above items 2 to 6, in which, $Ar^1$ to $Ar^3$ in the general formula (1-II), (2-II), (3-II), (4-II), or (5-II) each represent a substituted or unsubstituted divalent aliphatic hydrocarbon group.

10. An organic electroluminescence device comprising:
one or more organic thin-film layers sandwiched between a cathode and an anode, and having at least a light-emitting layer, in which the organic thin-film layer comprises the derivative of heterocyclic compound having a nitrogen atom according to any one of the above items 1 to 9.

11. An organic electroluminescence device according to the above item 10, which comprises the derivative of heterocyclic compound having a nitrogen atom mainly in a light-emitting domain.

12. An organic electroluminescence device according to the above item 10 or 11, which comprises the derivative of heterocyclic compound having a nitrogen atom mainly in a light-emitting layer.

13. An organic electroluminescence device according to the above item 10, in which:
the organic thin-film layer has an electron-injecting layer and/or an electron-transporting layer; and the derivative of heterocyclic compound having a nitrogen atom is a material for the electron-injecting layer and/or a material for the electron-transporting layer.

14. An organic electroluminescence device according to the above item 13, in which the electron-injecting layer and/or the electron-transporting layer contains a reductive dopant.

15. An organic electroluminescence device according to the above item 14, in which the reductive dopant is one or more kinds of substances selected from the group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal.

The use of the derivative of heterocyclic compound having a nitrogen atom of the present invention for at least one organic thin-film layer of an organic EL device provides the organic EL device with a high emission luminance and an extremely high efficiency of light emission even at a low voltage.

BEST MODE FOR CARRYING OUT THE INVENTION

The derivative of heterocyclic compound having a nitrogen atom of the present invention is represented by the following general formula (A-1) or (A-2).

(A-1)

(A-2)

In the formulae, $R^{1a}$ to $R^{5a}$ each represent a substituent, $Ar^{1a}$ to $Ar^{3a}$ each represent a single bond or a divalent connecting group, and HAr represents a group represented by the following general formula (A-3) or (A-4).

(A-3)

(A-4)

In the formulae, $R^{6a}$ to $R^{10a}$ each represent a substituent.

Among the heterocyclic derivatives having a nitrogen atom each represented by the general formula (A-1) or (A-2), derivative of heterocyclic compound having a nitrogen atom represented by the following general formulae (1-I) to (5-II) are preferable.

(1-I)

(1-II)

In the formulae, $R^1$ and $R^2$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^1$ and $R^2$ cannot simultaneously represent hydrogen atoms; $R^3$ represents any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; and $Ar^1$ represents a group selected from a substituted or unsubstituted arylene group, a substituted or unsubstituted heteroarylene group, and a substituted or unsubstituted divalent aliphatic hydrocarbon group.

(2-I)

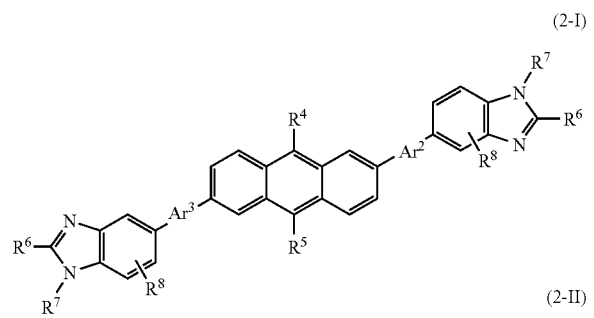

(2-II)

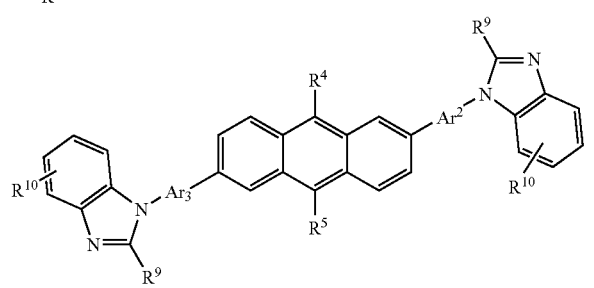

In the formulae, $R^4$ and $R^5$ each represent the same as described above; $R^6$, $R^7$, $R^8$, $R^9$, and $R^{10}$ each represent the same as described above; $Ar^2$ and $Ar^3$ each independently represent the same group as that of $Ar^1$.

(3-I)

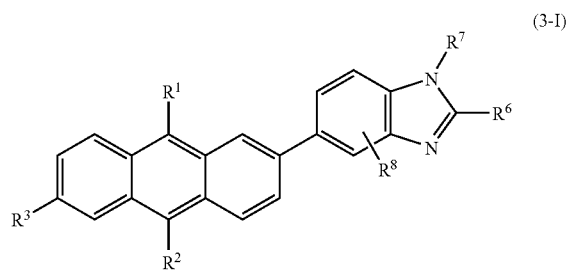

(3-II)

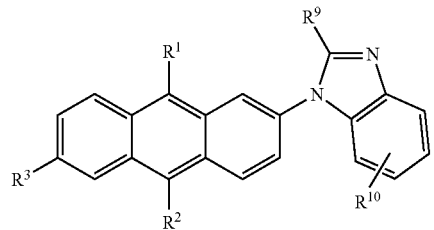

In the formulae, $R^1$, $R^2$, $R^3$, $R^6$, $R^7$, $R^8$, $R^9$, and $R^{10}$ each represent the same as described above.

(4-I)

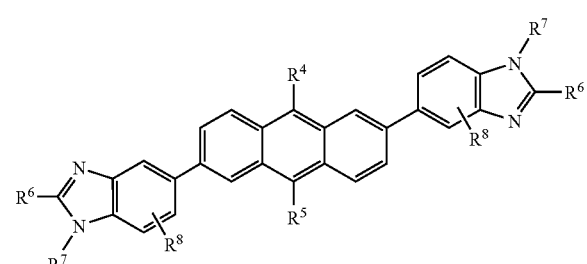

(4-II)

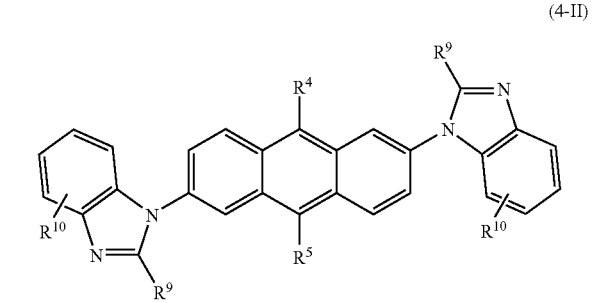

In the formulae, $R^4$, $R^5$, $R^6$, $R^7$, $R^8$, $R^9$, and $R^{10}$ each represent the same as described above.

(5-I)

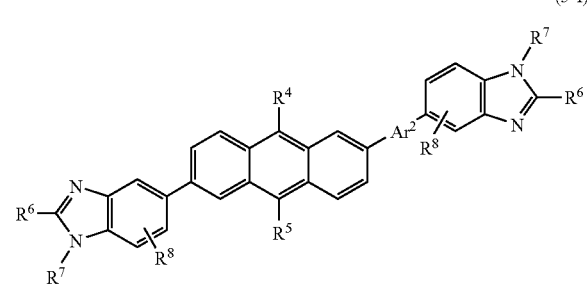

(5-II)

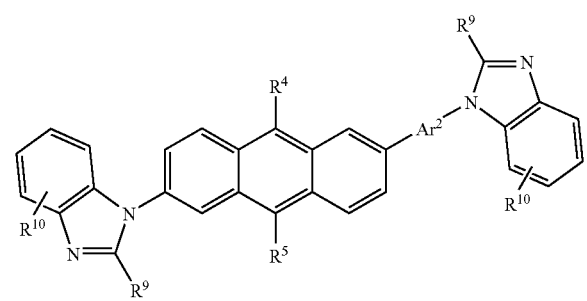

In the formulae, $R^1$, $R^2$, $R^3$, $R^6$, $R^7$, $R^8$, $R^9$, $R^{10}$, and $Ar^2$ each represent the same as described above.

Among the heterocyclic derivatives having a nitrogen atom each represented by the general formula (A-1) or (A-2), a derivative of heterocyclic compound having a nitrogen atom in which $R^{7a}$ in the general formula (A-3) represents a substituted or unsubstituted aliphatic hydrocarbon group, or $Ar^{1a}$ to $Ar^{3a}$ in the general formulae (A-1) and (A-2) each represent a substituted or unsubstituted divalent aliphatic hydrocarbon group is preferable. In addition, among the heterocyclic derivatives having a nitrogen atom each represented by the general formula (1-I), (2-I), (3-I), (4-I), or (5-I), a derivative of heterocyclic compound having a nitrogen atom in which $R^7$ represents a substituted or unsubstituted aliphatic hydrocarbon group, or $Ar^1$ to $Ar^3$ each represent a substituted or unsubstituted divalent aliphatic hydrocarbon group is preferable. Furthermore, among the heterocyclic derivatives having a nitrogen atom each represented by the general formula (1-II), (2-II), (3-II), (4-II), or (5-II), a derivative of heterocyclic compound having a nitrogen atom in which $Ar^1$ to $Ar^3$ each represent a substituted or unsubstituted divalent aliphatic hydrocarbon group is preferable.

Here, examples of a halogen atom represented by each of $R^1$, $R^2$, $R^3$, $R^4$, $R^5$, $R^6$, $R^8$, $R^9$, and $R^{10}$ in the general formulae (1-I) to (5-II) include fluorine, chlorine, bromine, and iodine. Of those, fluorine is preferable.

Examples of an unsubstituted aliphatic hydrocarbon group represented by each of $R^1$ to $R^{10}$ include an alkyl group having 1 to 40 carbon atoms, an alkynyl group having 2 to 40 carbon atoms, and an alkenyl group having 2 to 40 carbon atoms. Examples of the alkyl group include a methyl group, an ethyl group, a 1-propyl group, a 2-propyl group, a 1-butyl group, a 2-butyl group, an sec-butyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamanthyl group, a 2-adamanthyl group, a norbornyl group, a trifluoromethyl group, and a trichloromethyl group. Of those, a methyl group, an ethyl group, a 1-propyl group, a 2-propyl group, a 1-butyl group, a 2-butyl group, a sec-butyl group, and a tert-butyl group are preferable.

Examples of the alkynyl group include an ethynyl group and a methylethynyl group. Of those, an ethynyl group is preferable. Examples of the alkenyl group include a vinyl group, a propenyl group, a butenyl group, an oleyl group, an eicosapentaenyl group, and a docosahexaenyl group. Of those, a vinyl group and a propenyl group are preferable.

Each of the above aliphatic hydrocarbon groups may have a substituent, and examples of the substituent include: an aryl group (having preferably 6 to 30, more preferably 6 to 20, or particularly preferably 6 to 12 carbon atoms, such as a phenyl group, a p-methylphenyl group, or a naphthyl group); an amino group (having preferably 0 to 20, more preferably 0 to 12, or particularly preferably 0 to 6 carbon atoms, such as an amino group, a methylamino group, a dimethylamino group, a diethylamino group, a diphenylamino group, or a dibenzylamino group); an alkoxy group (having preferably 1 to 20, more preferably 1 to 12, or particularly preferably 1 to 8 carbon atoms, such as a methoxy group, an ethoxy group, or a butoxy group); an aryloxy group (having preferably 6 to 20, more preferably 6 to 16, or particularly preferably 6 to 12 carbon atoms, such as a phenyloxy group or a 2-naphthyloxy group); an acyl group (having preferably 1 to 20, more preferably 1 to 16, or particularly preferably 1 to 12 carbon atoms, such as an acetyl group, a benzoyl group, a formyl group, or a pivaloyl group); an alkoxycarbonyl group (having preferably 2 to 20, more preferably 2 to 16, or particularly preferably 2 to 12 carbon atoms, such as a methoxycarbonyl group or an ethoxycarbonyl group); an aryloxycarbonyl group (having preferably 7 to 20, more preferably 7 to 16, or particularly preferably 7 to 10 carbon atoms, such as a phenyloxycarbonyl group); an acyloxy group (having preferably 2 to 20, more preferably 2 to 16, or particularly preferably 2 to 10 carbon atoms, such as an acetoxy group or a benzoyloxy group); and an acylamino group (having preferably 2 to 20, more preferably 2 to 16, or particularly preferably 2 to 10 carbon atoms, such as an acetylamino group or a benzoylamino group).

Examples of the substituent further include: an alkoxycarbonyl group (having preferably 2 to 20, more preferably 2 to 16, or particularly preferably 2 to 12 carbon atoms, such as a methoxycarbonylamino group); an aryloxycarbonylamino group (having preferably 7 to 20, more preferably 7 to 16, or particularly preferably 7 to 12 carbon atoms, such as a phenyloxycarbonyl group); a sulfonylamino group (having preferably 1 to 20, more preferably 1 to 16, or particularly preferably 1 to 12 carbon atoms, such as a methane sulfonylamino group or a benzene sulfonylamino group); a sulfamoyl group (having preferably 0 to 20, more preferably 0 to 16, or particularly preferably 0 to 12 carbon atoms, such as a sulfamoyl group, a methylsulfamoyl group, a dimethylsulfamoyl group, or a phenylsulfamoyl group); a carbamoyl group (having preferably 1 to 20, more preferably 1 to 16, or particularly preferably 1 to 12 carbon atoms, such as a carbamoyl group, a methylcarbamoyl group, a diethylcarbamoyl group, or a phenylcarbamoyl group); an alkylthio group (having preferably 1 to 20, more preferably 1 to 16, or particularly preferably 1 to 12 carbon atoms, such as a methylthio group or an ethylthio group); and an arylothio group (having preferably 6 to 20, more preferably 6 to 16, or particularly preferably 6 to 12 carbon atoms, such as a phenylthio group).

The examples further include: a sulfonyl group (having preferably 1 to 20, more preferably 1 to 16, or particularly preferably 1 to 12 carbon atoms, such as a methyl group or a tosyl group); a sulfinyl group (having preferably 1 to 20, more preferably 1 to 16, or particularly preferably 1 to 12 carbon atoms, such as a methanesulfinyl group or a benzenesulfinyl group; a ureido group (having preferably 1 to 20, more preferably 1 to 16, or particularly preferably 1 to 12 carbon atoms, such as a ureido group, a methylureido group, or a phenylureido group); a phosphoric amide group (having preferably 1 to 20, more preferably 1 to 16, or particularly preferably 1 to 12 carbon atoms, such as a diethylphosphoric amide group or a phenylphosphoric amide group); a hydroxyl group; a mercapto group; a halogen atom (such as a fluorine atom, a chlorine atom, a bromine atom, or an iodine atom); a cyano group; a sulfo group; a carboxyl group; a nitro group; a hydroxamic group; a sulfino group; a hydrazino group; an imino group; and a heterocyclic group (having preferably 1 to 30, or more preferably 1 to 12 carbon atoms and containing, as a hetero atom, a nitrogen atom, an oxygen atom, a sulfur atom, or the like, specifically an imidazolyl group, a pyridyl group, a quinolyl group, a furyl group, a thienyl group, a piperidyl group, a morpholino group, a benzoxazolyl group, a benzoimidazolyl group, a benzothiazolyl group, a carbazolyl group, or the like); and a silyl group (having preferably 3 to 40, more preferably 3 to 30, or particularly preferably 3 to 24 carbon atoms, such as a trimethylsilyl group or a triphenylsilyl group). Each of those substituents may be additionally substituted. When two or more substituents are present, they may be identical to or different from each other. In addition, the substituents may bind to each other to form a ring if possible.

Examples of an unsubstituted aryl group represented by each of $R^1$ to $R^{10}$ include those each having 5 to 60 carbon atoms. Preferable examples thereof include a phenyl group, a 2-biphenylyl group, a 3-biphenylyl group, a 4-biphenylyl group, a terphenylyl group, a 3,5-diphenylphenyl group, a 3,4-diphenylphenyl group, a pentaphenylphenyl group, a fluorenyl group, a 1-naphthyl group, a 2-naphthyl group, a 9-anthryl group, a 2-anthryl group, a 9-phenanthryl group, a 1-pyrenyl group, a chrysenyl group, a naphthacenyl group, a coronyl group, a 10-phenyl-anthracen-9-yl group, a 10-naphthalen-2-yl-anthracen-9-yl group, a 12-phenyl-chrysen-6-yl group, a (10-phenyl-anthracen-9-yl)-4-phenyl group, a (10-naphthalen-2yl-anthracen-9-yl)-4-phenyl group, and a spiro aromatic ring group. The spiro aromatic ring group is a compound represented by the following general formula.

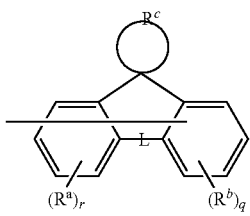

In the formula, $R^a$ and $R^b$ each independently represent any one selected from a group consisting of a hydrogen atom, an alkyl group, a substituted or unsubstituted aromatic ring, and a substituted or unsubstituted heterocyclic ring; $R^c$ represents an atomic group forming a cyclic structure; $R^a$ and $R^b$ may bind to each other to form a ring; r and q each represent an integer of 0 to 4.

Examples of the spiro aromatic ring group include a spiro (cyclohexane-1,9'-fluoren)-2'-yl group, a spiro(cyclopentane-1,9'-fluoren)-2'-yl group, a spiro(indene-1,9'-fluoren)-2'-yl group, a dispiro(bisfluorene-9,10,9',9'''-9,9,10,10-tetrahydroanthracen)-2'-yl group, a dispiro(bisfluorene-9,10,9',9'''-9,9,10,10-tetrahydroanthracen)-2'-yl group, and a 9,9'-spirobifluoren-2-yl group.

Each of the above aryl groups may have a substituent, and examples of the substituent include: an alkyl group (having preferably 1 to 20, more preferably 1 to 12, or particularly preferably 1 to 8 carbon atoms, such as a methyl group, an ethyl group, an isopropyl group, a tert-butyl group, an n-octyl group, an n-decyl group, an n-hexadecyl group, a cyclopropyl group, a cyclopentyl group, or a cyclohexyl group); an alkenyl group (having preferably 2 to 20, more preferably 2 to 12, or particularly preferably 2 to 8 carbon atoms, such as a vinyl group, an allyl group, a 2-butenyl group, or a 3-pentenyl group); an alkynyl group (having preferably 2 to 20, more preferably 2 to 12, or particularly preferably 2 to 8 carbon atoms, such as a propargyl group or a 3-pentynyl group); an amino group (having preferably 0 to 20, more preferably 0 to 12, or particularly preferably 0 to 6 carbon atoms, such as an amino group, a methylamino group, a dimethylamino group, a diethylamino group, a diphenylamino group, or a dibenzylamino group); an alkoxy group (having preferably 1 to 20, more preferably 1 to 12, or particularly preferably 1 to 8 carbon atoms, such as a methoxy group, an ethoxy group, or a butoxy group); an aryloxy group (having preferably 6 to 20, more preferably 6 to 16, or particularly preferably 6 to 12 carbon atoms, such as a phenyloxy group or a 2-naphthyloxy group); an acyl group (having preferably 1 to 20, more preferably 1 to 16, or particularly preferably 1 to 12 carbon atoms, such as an acetyl group, a benzoyl group, a formyl group, or a pivaloyl group); an alkoxycarbonyl group (having preferably 2 to 20, more preferably 2 to 16, or particularly preferably 2 to 12 carbon atoms, such as a methoxycarbonyl group or an ethoxycarbonyl group); an aryloxycarbonyl group (having preferably 7 to 20, more preferably 7 to 16, or particularly preferably 7 to 10 carbon atoms, such as a phenyloxycarbonyl group); an acyloxy group (having preferably 2 to 20, more preferably 2 to 16, or particularly preferably 2 to 10 carbon atoms, such as an acetoxy group or a benzoyloxy group); and an acylamino group (having preferably 2 to 20, more preferably 2 to 16, or particularly preferably 2 to 10 carbon atoms, such as an acetylamino group or a benzoylamino group).

The examples further include: an alkoxycarbonylamino group (having preferably 2 to 20, more preferably 2 to 16, or particularly preferably 2 to 12 carbon atoms, such as a methoxycarbonylamino group); an aryloxycarbonylamino group (having preferably 7 to 20, more preferably 7 to 16, or particularly preferably 7 to 12 carbon atoms, such as a phenyloxycarbonylamino group); a sulfonylamino group (having preferably 1 to 20, more preferably 1 to 16, or particularly preferably 1 to 12 carbon atoms, such as a methanesulfonylamino group or a benzenesulfonylamino group); a sulfamoyl group (having preferably 0 to 20, more preferably 0 to 16, or particularly preferably 0 to 12 carbon atoms, such as a sulfamoyl group, a methylsulfamoyl group, a dimethylsulfamoyl group, or a phenylsulfamoyl group); a carbamoyl group (having preferably 1 to 20, more preferably 1 to 16, or particularly preferably 1 to 12 carbon atoms, such as a carbamoyl group, a methylcarbamoyl group, a diethylcarbamoyl group, or a phenylcarbamoyl group); an alkylthio group (having preferably 1 to 20, more preferably 1 to 16, or particularly preferably 1 to 12 carbon atoms, such as a methylthio group or an ethylthio group); and an arylthio group (having preferably 6 to 20, more preferably 6 to 16, or particularly preferably 6 to 12 carbon atoms, such as a phenylthio group).

The examples further include: a sulfonyl group (having preferably 1 to 20, more preferably 1 to 16, or particularly preferably 1 to 12 carbon atoms, such as a mesyl group or a tosyl group); a sulfinyl group (having preferably 1 to 20, more preferably 1 to 16, or particularly preferably 1 to 12 carbon atoms, such as a methanesulfinyl group or a benzenesulfinyl group); a ureido group (having preferably 1 to 20, more preferably 1 to 16, or particularly preferably 1 to 12 carbon atoms, such as a ureido group, a methylureido group, or a phenylureido group); a phosphoric amide group (having preferably 1 to 20, more preferably 1 to 16, or particularly preferably 1 to 12 carbon atoms, such as a diethylphosphoric amide group or a phenylphosphoric amide group); a hydroxyl group; a mercapto group; a halogen atom (such as a fluorine atom, a chlorine atom, a bromine atom, or an iodine atom); a cyano group; a sulfo group; a carboxyl group; a nitro group; a hydroxamic group; a sulfino group; a hydrazino group; an imino group; a heterocyclic group (having preferably 1 to 30, or more preferably 1 to 12 carbon atoms and containing, as a hetero atom, a nitrogen atom, an oxygen atom, a sulfur atom, or the like, specifically an imidazolyl group, a pyridyl group, a quinolyl group, a furyl group, a thienyl group, a piperidyl group, a morpholino group, a benzoxazolyl group, a benzoimidazolyl group, a benzothiazolyl group, a carbazolyl group, or the like); and a silyl group (having preferably 3 to 40, more preferably 3 to 30, or particularly preferably 3 to 24 carbon atoms, such as a trimethylsilyl group or a triphenylsilyl group). Each of those substituents may be additionally substituted. When two or more substituents are present, they may be identical to or different from each other. In addition, the substituents may bind to each other to form a ring if possible.

Examples of an unsubstituted heteroaryl group represented by each of $R^1$ to $R^{10}$ include those each having 3 to 60 carbon atoms. Preferable examples thereof include groups selected from residues such as furan, thiophene, pyrrole, imidazole, pyrazole, triazole, oxadiazole, pyridine, pyrazine, triazine, benzofuran, dibenzofuran, benzothiophene, dibenzothiophene, carbazole, benzimidazole, and imidazopyridine.

Each of the above heteroaryl groups may have a substituent, and examples of the substituent include: an alkyl group (having preferably 1 to 20, more preferably 1 to 12, or particularly preferably 1 to 8 carbon atoms, such as a methyl group, an ethyl group, an isopropyl group, a tert-butyl group, an n-octyl group, an n-decyl group, an n-hexadecyl group, a cyclopropyl group, a cyclopentyl group, or a cyclohexyl group); an alkenyl group (having preferably 2 to 20, more preferably 2 to 12, or particularly preferably 2 to 8 carbon atoms, such as a vinyl group, an allyl group, a 2-butenyl group, or a 3-pentenyl group); an alkynyl group (having preferably 2 to 20, more preferably 2 to 12, or particularly preferably 2 to 8 carbon atoms, such as a propargyl group or a 3-pentynyl group); an aryl group (having preferably 6 to 30, more preferably 6 to 20, or particularly preferably 6 to 12 carbon atoms, such as a phenyl group, a p-methylphenyl group, or a naphthyl group); an amino group (having preferably 0 to 20, more preferably 0 to 12, or particularly preferably 0 to 6 carbon atoms, such as an amino group, a methylamino group, a dimethylamino group, a diethylamino group, a diphenylamino group, or a dibenzylamino group); an alkoxy group (having preferably 1 to 20, more preferably 1 to 12, or particularly preferably 1 to 8 carbon atoms, such as a methoxy group, an ethoxy group, or a butoxy group); an aryloxy group (having preferably 6 to 20, more preferably 6 to 16, or particularly preferably 6 to 12 carbon atoms, such as a phenyloxy group or a 2-naphthyloxy group); an acyl group (having preferably 1 to 20, more preferably 1 to 16, or particularly preferably 1 to 12 carbon atoms, such as an acetyl group, a benzoyl group, a formyl group, or a pivaloyl group); an alkoxycarbonyl group (having preferably 2 to 20, more preferably 2 to 16, or particularly preferably 2 to 12 carbon atoms, such as a methoxycarbonyl group or an ethoxycarbonyl group); an aryloxycarbonyl group (having preferably 7 to 20, more preferably 7 to 16, or particularly preferably 7 to 10 carbon atoms, such as a phenyloxycarbonyl group); an acyloxy group (having preferably 2 to 20, more preferably 2 to 16, or particularly preferably 2 to 10 carbon atoms, such as an acetoxy group or a benzoyloxy group); and an acylamino group (having preferably 2 to 20, more preferably 2 to 16, or particularly preferably 2 to 10 carbon atoms, such as an acetylamino group or a benzoylamino group).

The examples further include: an alkoxycarbonylamino group (having preferably 2 to 20, more preferably 2 to 16, or particularly preferably 2 to 12 carbon atoms, such as a methoxycarbonylamino group); an aryloxycarbonylamino group (having preferably 7 to 20, more preferably 7 to 16, or particularly preferably 7 to 12 carbon atoms, such as a phenyloxycarbonylamino group); a sulfonylamino group (having preferably 1 to 20, more preferably 1 to 16, or particularly preferably 1 to 12 carbon atoms, such as a methanesulfonylamino group or a benzenesulfonylamino group); a sulfamoyl group (having preferably 0 to 20, more preferably 0 to 16, or particularly preferably 0 to 12 carbon atoms, such as a sulfamoyl group, a methylsulfamoyl group, a dimethylsulfamoyl group, or a phenylsulfamoyl group); a carbamoyl group (having preferably 1 to 20, more preferably 1 to 16, or particularly preferably 1 to 12 carbon atoms, such as a carbamoyl group, a methylcarbamoyl group, a diethylcarbamoyl group, or a phenylcarbamoyl group); an alkylthio group (having preferably 1 to 20, more preferably 1 to 16, or particularly preferably 1 to 12 carbon atoms, such as a methylthio group or an ethylthio group); and an arylthio group (having preferably 6 to 20, more preferably 6 to 16, or particularly preferably 6 to 12 carbon atoms, such as a phenylthio group).

The examples further include: a sulfonyl group (having preferably 1 to 20, more preferably 1 to 16, or particularly preferably 1 to 12 carbon atoms, such as a mesyl group or a tosyl group); a sulfinyl group (having preferably 1 to 20, more preferably 1 to 16, or particularly preferably 1 to 12 carbon atoms, such as a methanesulfinyl group or a benzenesulfinyl group); a ureido group (having preferably 1 to 20, more preferably 1 to 16, or particularly preferably 1 to 12 carbon atoms, such as a ureido group, a methylureido group, or a phenylureido group); a phosphoric amide group (having preferably 1 to 20, more preferably 1 to 16, or particularly preferably 1 to 12 carbon atoms, such as a diethylphosphoric amide group or a phenylphosphoric amide group); a hydroxyl group; a mercapto group; a halogen atom (such as a fluorine atom, a chlorine atom, a bromine atom, or an iodine atom); a cyano group; a sulfo group; a carboxyl group; a nitro group; a hydroxamic group; a sulfino group; a hydrazino group; an imino group; and a silyl group (having preferably 3 to 40, more preferably 3 to 30, or particularly preferably 3 to 24 carbon atoms, such as a trimethylsilyl group or a triphenylsilyl group). Each of those substituents may be additionally substituted. When two or more substituents are present, they may be identical to or different from each other. In addition, the substituents may bind to each other to form a ring if possible.

Examples of an unsubstituted alkoxy group represented by each of $R^3$, $R^8$, and $R^{10}$ include a methoxy group, an ethoxy group, a 1-propyloxy group, a 2-propyloxy group, a 1-butyloxy group, a 2-butyloxy group, an sec-butyloxy group, a tert-butyloxy group, a pentyloxy group, a hexyloxy group, an octyloxy group, a decyloxy group, a dodecyloxy group, a 2-ethylhexyloxy group, a 3,7-dimethyloctyloxy group, a cyclopropyloxy group, a cyclopentyloxy group, a cyclohexyloxy group, a 1-adamanthyloxy group, a 2-adamanthyloxy group, a norbornyloxy group, a trifluoromethoxy group, a benzyloxy group, an α,α-dimethylbenzyloxy group, a 2-phenylethoxy group, and a 1-phenylethoxy group.

Each of the above alkoxy groups may have a substituent, and examples of the substituent include: an alkenyl group (having preferably 2 to 20, more preferably 2 to 12, or particularly preferably 2 to 8 carbon atoms, such as a vinyl group, an allyl group, a 2-butenyl group, or a 3-pentenyl group); an alkynyl group (having preferably 2 to 20, more preferably 2 to 12, or particularly preferably 2 to 8 carbon atoms, such as a propargyl group or a 3-pentynyl group); an aryl group (having preferably 6 to 30, more preferably 6 to 20, or particularly preferably 6 to 12 carbon atoms, such as a phenyl group, a p-methylphenyl group, or a naphthyl group); an amino group (having preferably 0 to 20, more preferably 0 to 12, or particularly preferably 0 to 6 carbon atoms, such as an amino group, a methylamino group, a dimethylamino group, a diethylamino group, a diphenylamino group, or a dibenzylamino group); an aryloxy group (having preferably 6 to 20, more preferably 6 to 16, or particularly preferably 6 to 12 carbon atoms, such as a phenyloxy group or a 2-naphthyloxy group); an acyl group (having preferably 1 to 20, more preferably 1 to 16, or particularly preferably 1 to 12 carbon atoms, such as an acetyl group, a benzoyl group, a formyl group, or a pivaloyl group); an alkoxycarbonyl group (having preferably 2 to 20, more preferably 2 to 16, or particularly preferably 2 to 12 carbon atoms, such as a methoxycarbonyl group or an ethoxycarbonyl group); an aryloxycarbonyl group (having preferably 7 to 20, more preferably 7 to 16, or particularly preferably 7 to 10 carbon atoms, such as a phenyloxycarbonyl group); an acyloxy group (having preferably 2 to 20, more preferably 2 to 16, or particularly preferably 2 to 10 carbon atoms, such as an acetoxy group or a benzoyloxy group); and an acylamino group (having preferably 2 to 20, more preferably 2 to 16, or particularly preferably 2 to 10 carbon atoms, such as an acetylamino group or a benzoylamino group).

The examples further include: an alkoxycarbonylamino group (having preferably 2 to 20, more preferably 2 to 16, or particularly preferably 2 to 12 carbon atoms, such as a methoxycarbonylamino group) an aryloxycarbonylamino group (having preferably 7 to 20, more preferably 7 to 16, or particularly preferably 7 to 12 carbon atoms, such as a phenyloxycarbonylamino group); a sulfonylamino group (having preferably 1 to 20, more preferably 1 to 16, or particularly preferably 1 to 12 carbon atoms, such as a methanesulfonylamino group or a benzenesulfonylamino group); a sulfamoyl group (having preferably 0 to 20, more preferably 0 to 16, or particularly preferably 0 to 12 carbon atoms, such as a sulfamoyl group, a methylsulfamoyl group, a dimethylsulfamoyl group, or a phenylsulfamoyl group); a carbamoyl group (having preferably 1 to 20, more preferably 1 to 16, or particularly preferably 1 to 12 carbon atoms, such as a carbamoyl group, a methylcarbamoyl group, a diethylcarbamoyl group, or a phenylcarbamoyl group); an alkylthio group (having preferably 1 to 20, more preferably 1 to 16, or particularly preferably 1 to 12 carbon atoms, such as a methylthio group or an ethylthio group); and an arylthio group (having preferably 6 to 20, more preferably 6 to 16, or particularly preferably 6 to 12 carbon atoms, such as a phenylthio group).

The examples further include: a sulfonyl group (having preferably 1 to 20, more preferably 1 to 16, or particularly preferably 1 to 12 carbon atoms, such as a mesyl group or a tosyl group); a sulfinyl group (having preferably 1 to 20, more preferably 1 to 16, or particularly preferably 1 to 12 carbon atoms, such as a methanesulfinyl group or a benzenesulfinyl group); a ureido group (having preferably 1 to 20, more preferably 1 to 16, or particularly preferably 1 to 12 carbon atoms, such as a ureido group, a methylureido group, or a phenylureido group); a phosphoric amide group (having preferably 1 to 20, more preferably 1 to 16, or particularly preferably 1 to 12 carbon atoms, such as a diethylphosphoric amide group or a phenylphosphoric amide group); a hydroxyl group; a mercapto group; a halogen atom (such as a fluorine atom, a chlorine atom, a bromine atom, or an iodine atom); a cyano group; a sulfo group; a carboxyl group; a nitro group; a hydroxamic group; a sulfino group; a hydrazino group; an imino group; a heterocyclic group (having preferably 1 to 30, or more preferably 1 to 12 carbon atoms and containing, as a hetero atom, a nitrogen atom, an oxygen atom, a sulfur atom, or the like, specifically an imidazolyl group, a pyridyl group, a quinolyl group, a furyl group, a thienyl group, a piperidyl group, a morpholino group, a benzoxazolyl group, a benzoimidazolyl group, a benzothiazolyl group, a carbazolyl group, or the like); and a silyl group (having preferably 3 to 40, more preferably 3 to 30, or particularly preferably 3 to 24 carbon atoms, such as a trimethylsilyl group or a triphenylsilyl group). Each of those substituents may be additionally substituted. When two or more substituents are present, they may be identical to or different from each other. In addition, the substituents may bind to each other to form a ring if possible.

An arylene group represented by each of $Ar^1$ to $Ar^3$ is a divalent aromatic group, and examples thereof include a phenylene group, a naphthylene group, an anthrylene group, a biphenylene group, a terphenylene group, a pyrenylene group, a chrysenylene group, a fluorenylene group, and a spirofluorenylene group. Of those, a phenylene group is preferable. The arylene group may have a substituent, and any one of the examples of the substituent of the aryl group is applicable.

A heteroarylene group is a divalent heterocyclic group, and examples thereof include divalent groups each composed of a thiophene ring, a furan ring, a selenophene ring, a pyridine ring, a pyrazine ring, an oxadiazole ring, a thiadiazole ring, an oxazole ring, a thiazole ring, a triazole ring, or the like. Of those, a thiophene ring, a pyridine ring, an oxadiazole ring, and a triazole ring are preferable. The heteroarylene group may have a substituent, and any one of the examples of the substituent of the heteroaryl group is applicable.

Examples of a divalent aliphatic hydrocarbon group represented by each of $Ar^1$ to $Ar^3$ include a methylene group, a propylene group, a butylene group, a vinylene group, and an ethynylene group. Of those, a methylene group is preferable. The divalent aliphatic hydrocarbon group may have a substituent, and any one of the examples of the substituent of the aliphatic hydrocarbon group is applicable.

Specific examples of the derivative of heterocyclic compound having a nitrogen atoms represented by the general formulae (1-I) to (5-II) are shown below. However, the present invention is not limited thereto.

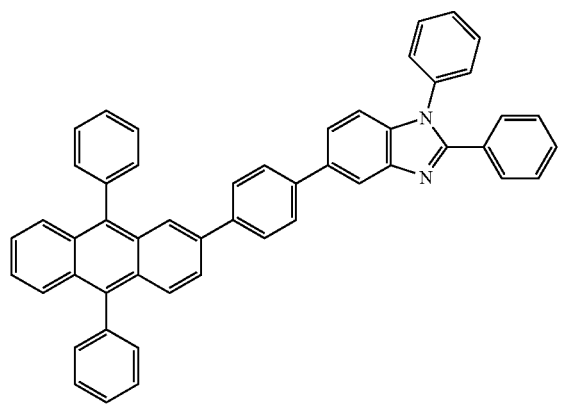

1-1

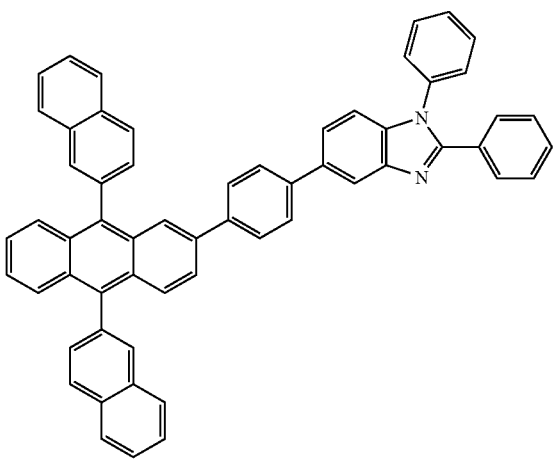

1-2

-continued
1-3 1-4
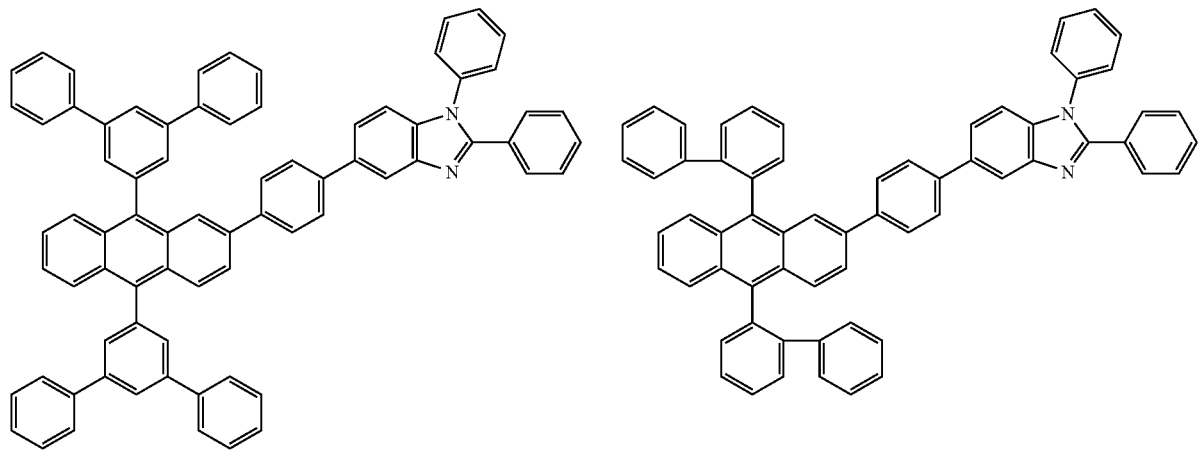
1-5 1-6
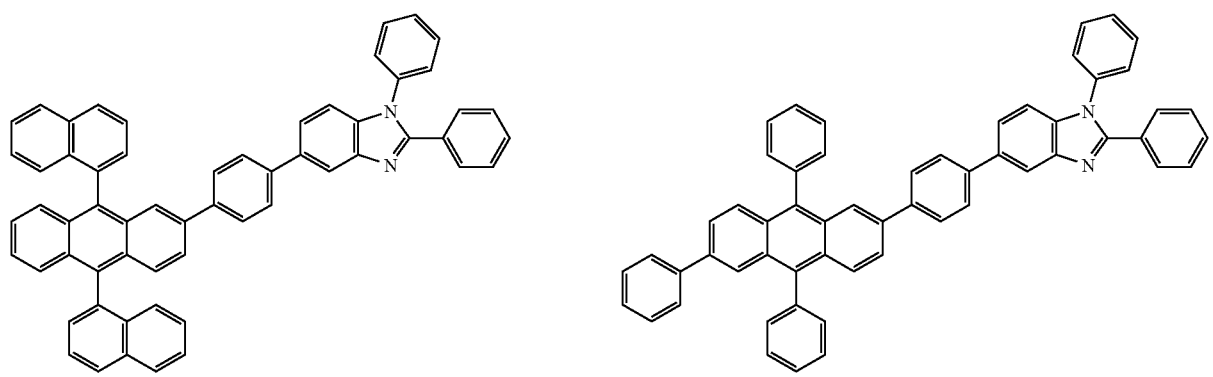
1-7 1-8
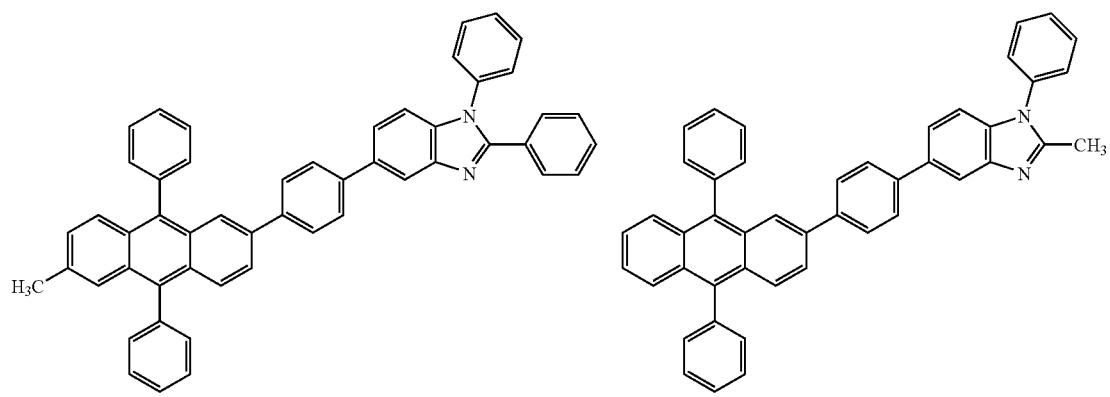
1-9 1-10
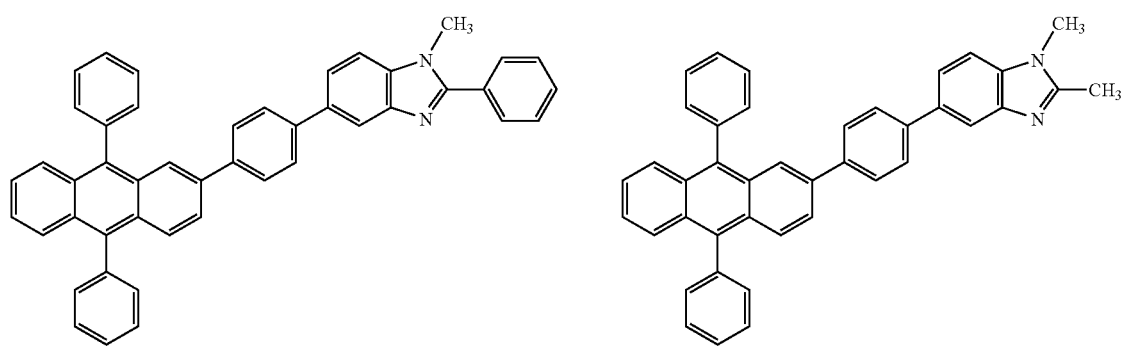

-continued
1-11
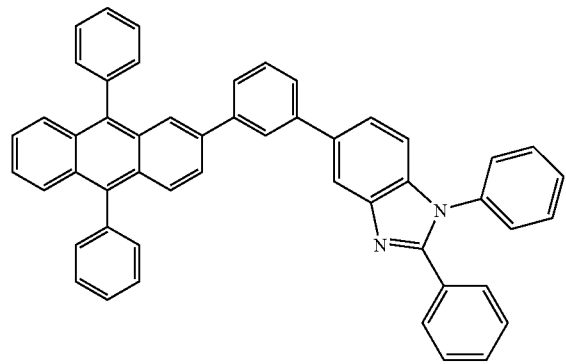
1-12
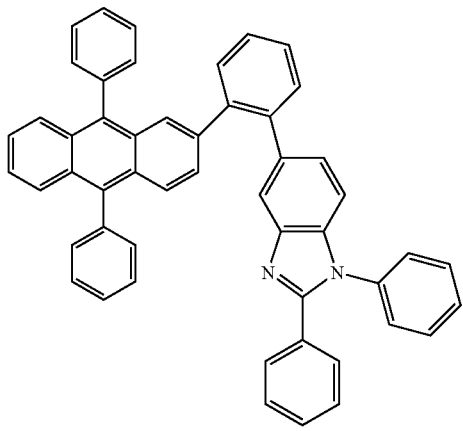
1-13
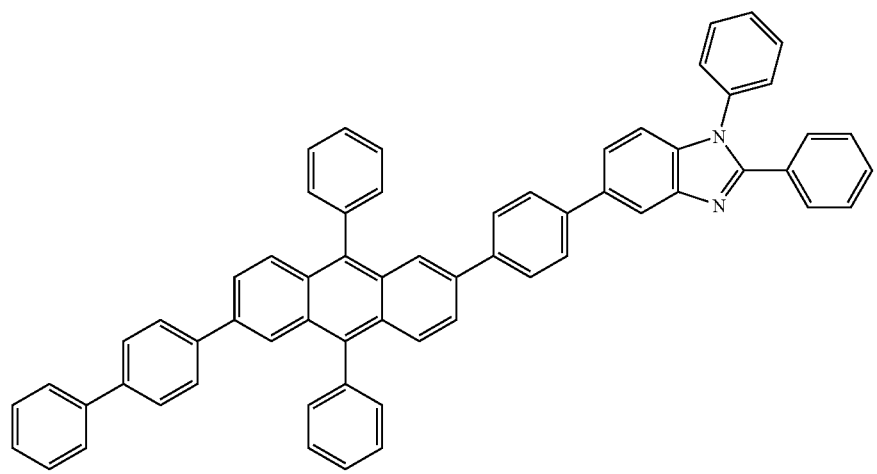
1-14
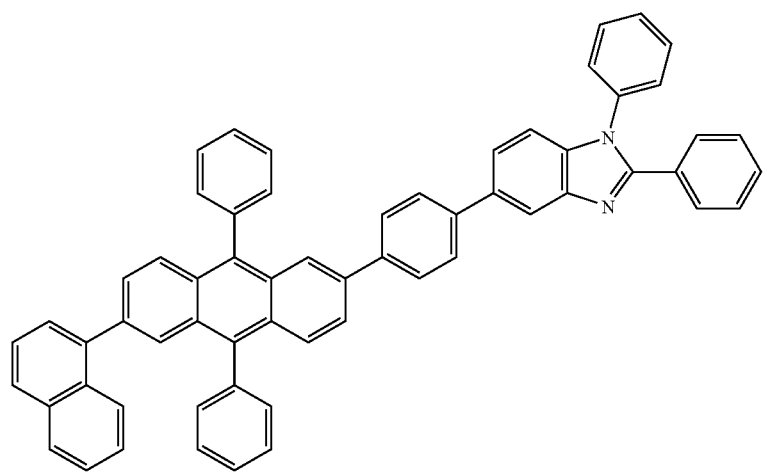

-continued
1-15
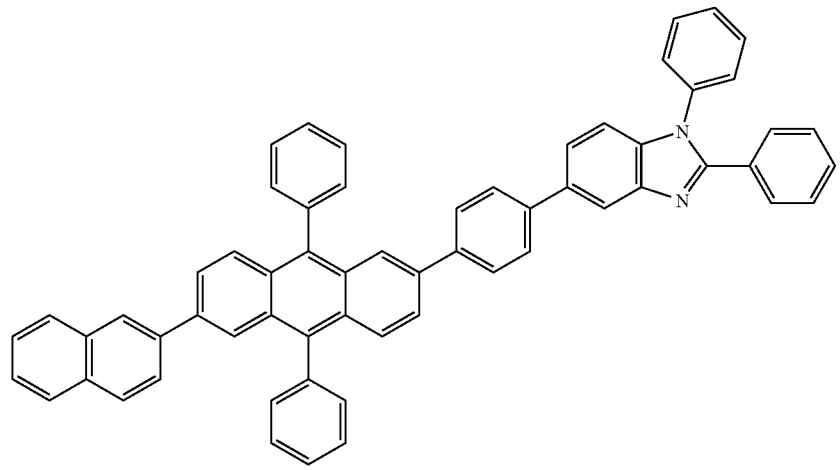
1-16
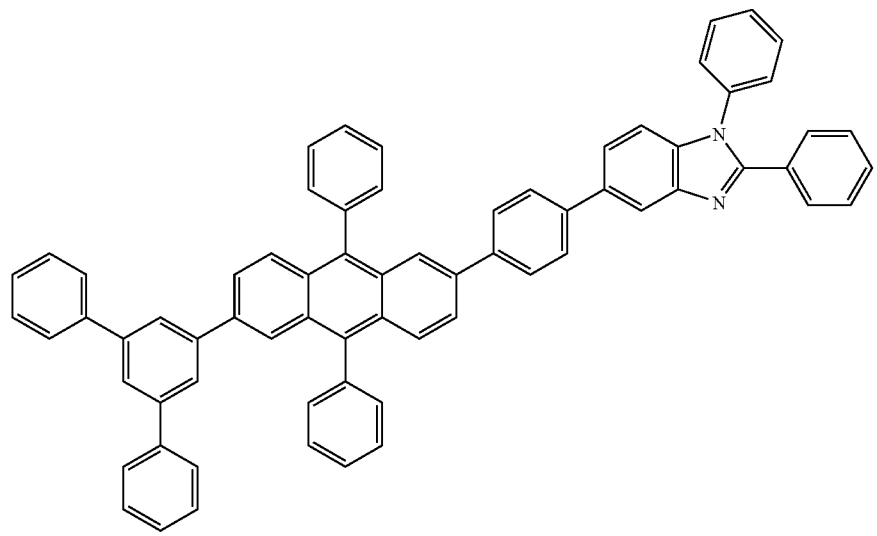
1-17
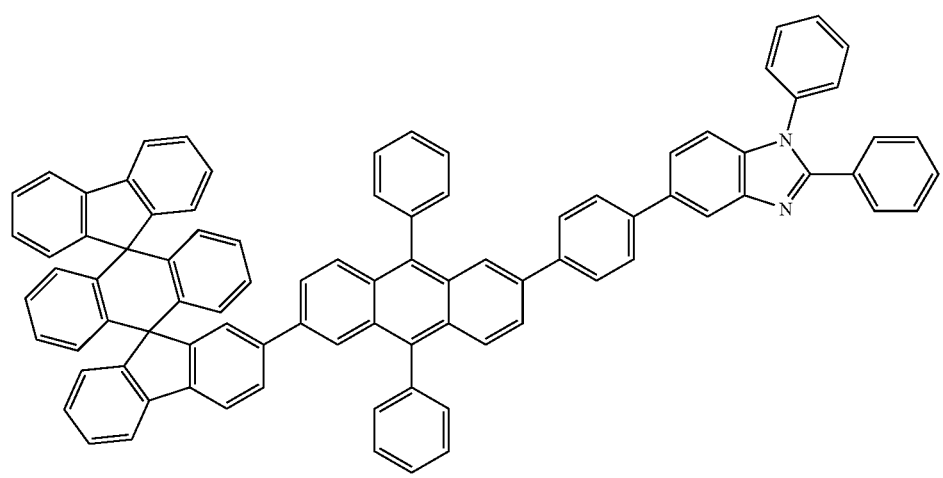

-continued
1-18
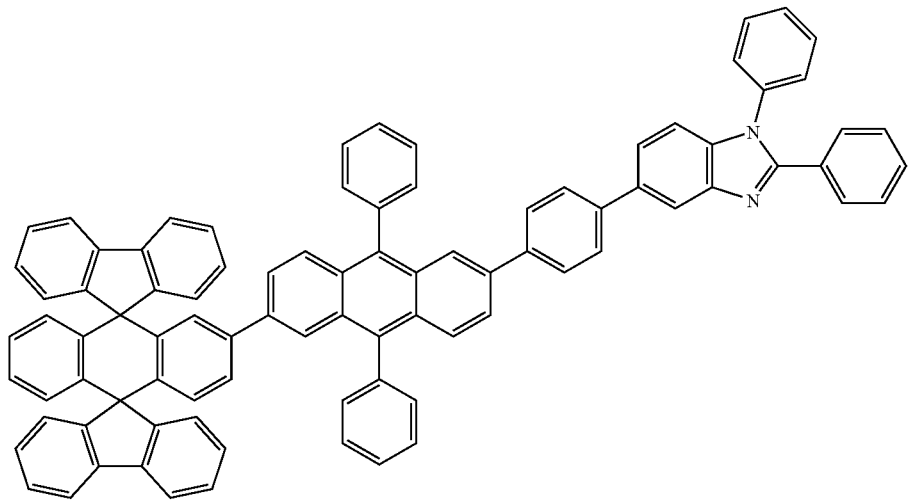
1-19
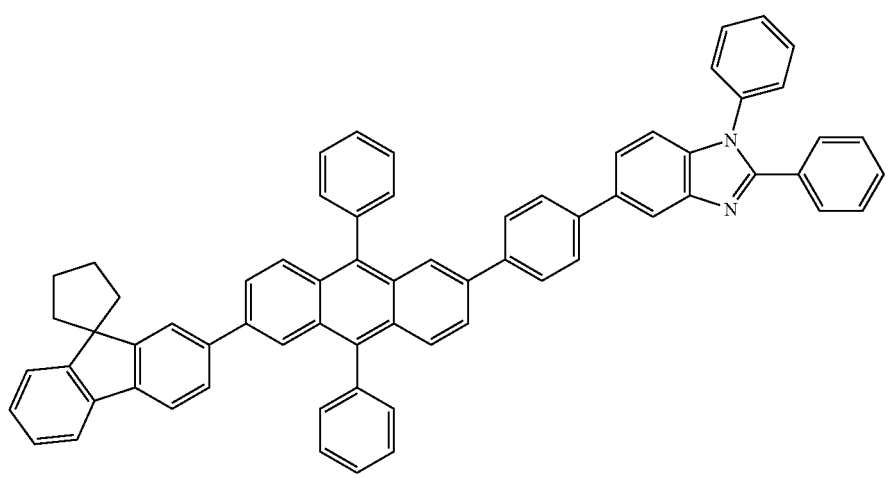
1-20
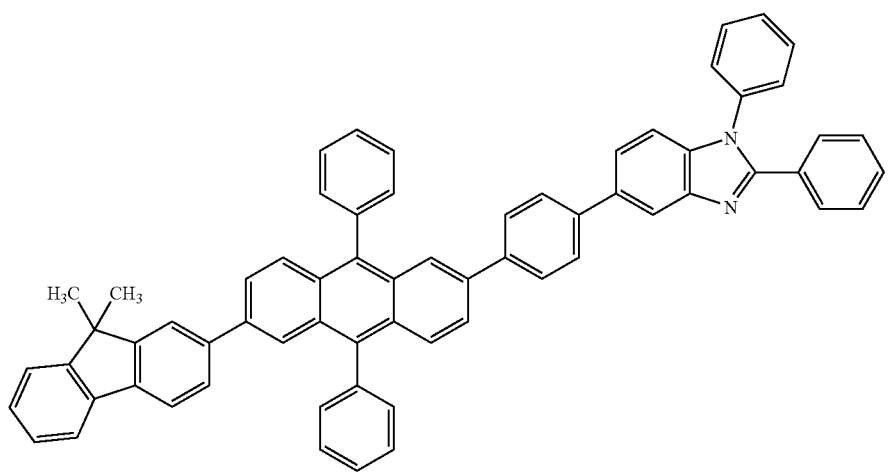

-continued
1-21
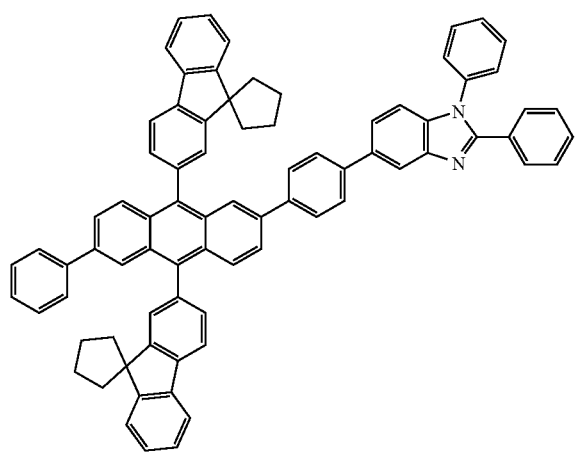
1-22
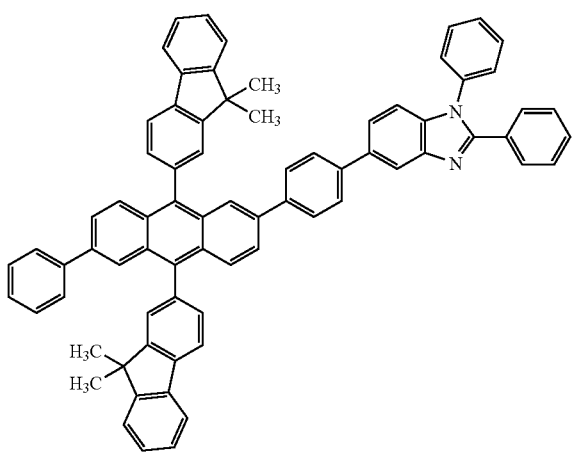
1-23
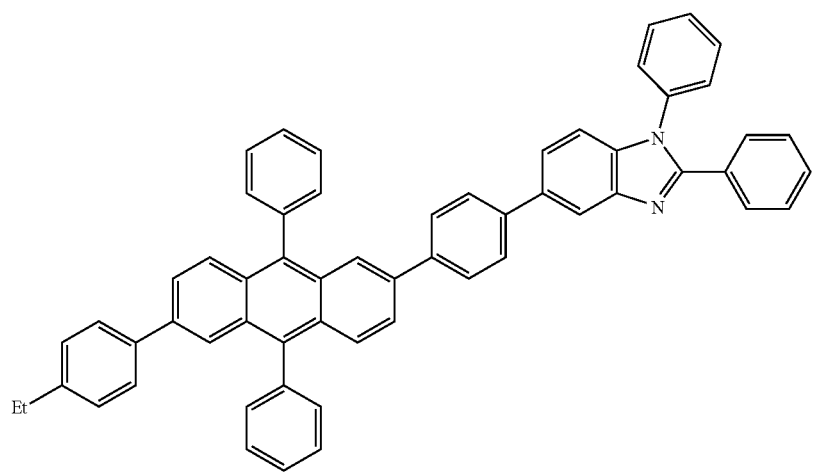
1-24
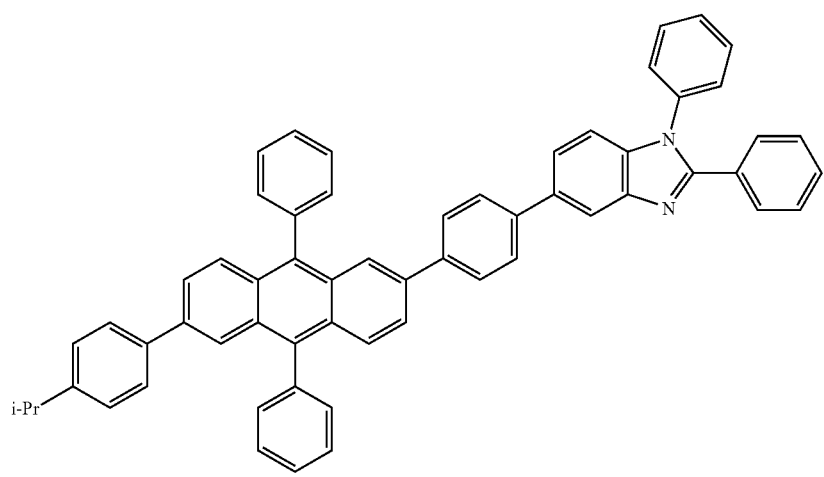

-continued
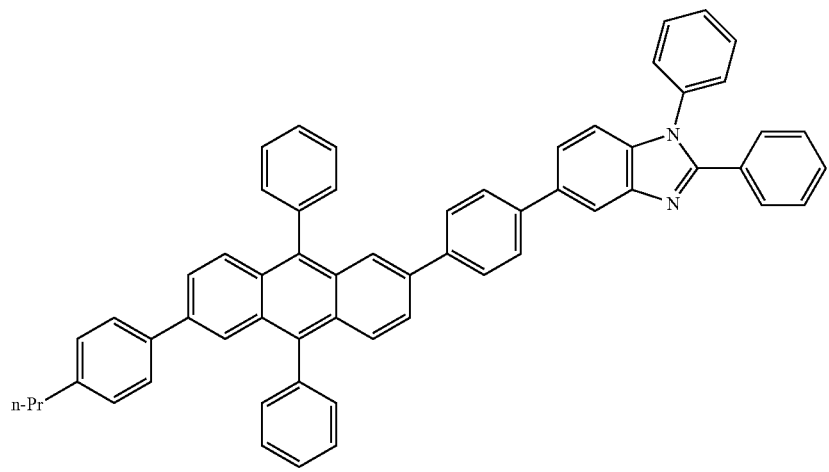
1-25
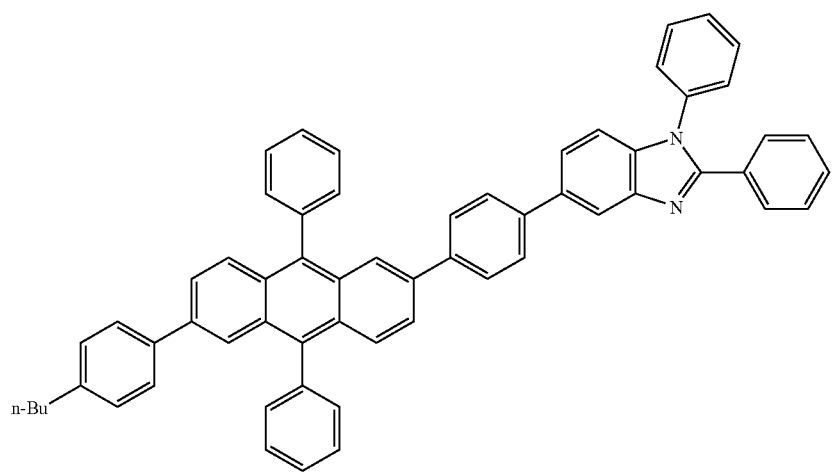
1-26
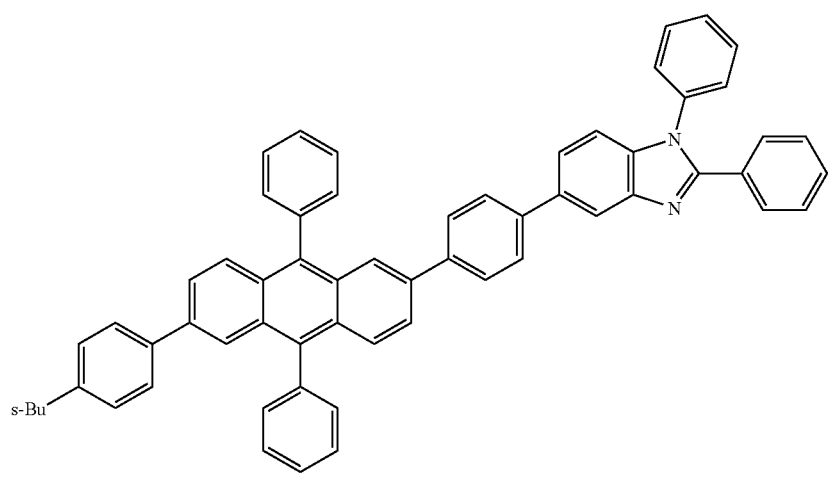
1-27

-continued
1-28
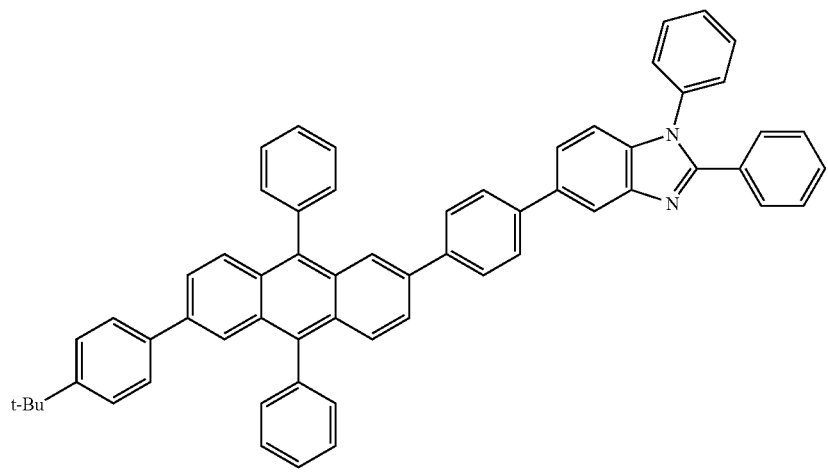
1-29 1-30
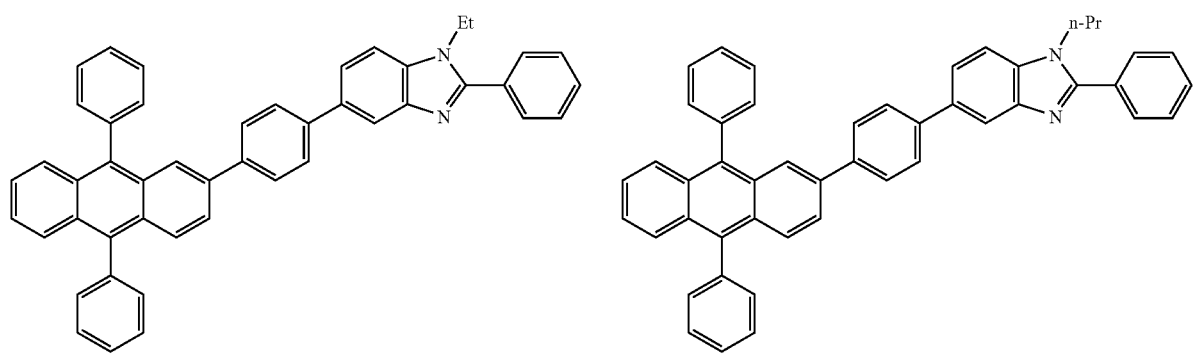
1-31 1-32
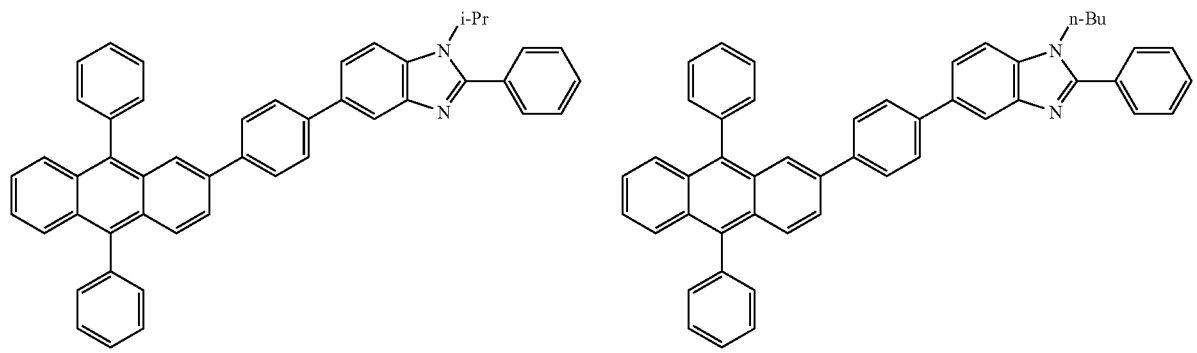
1-33 1-34
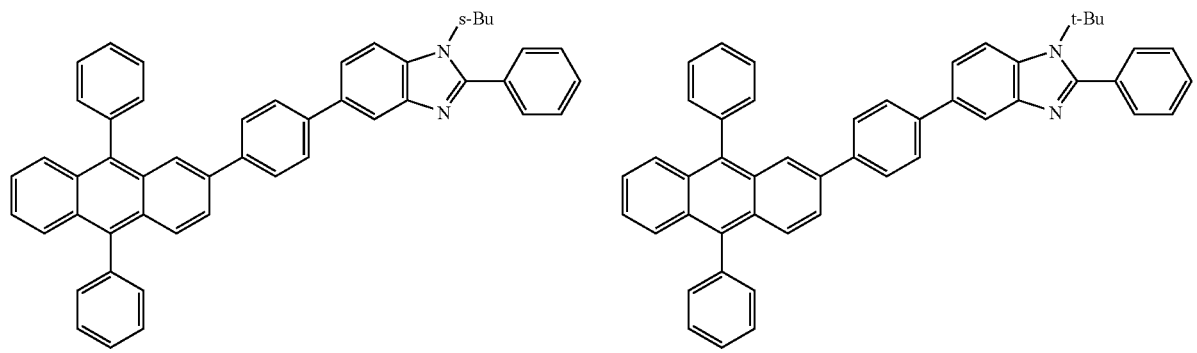

-continued
1-35
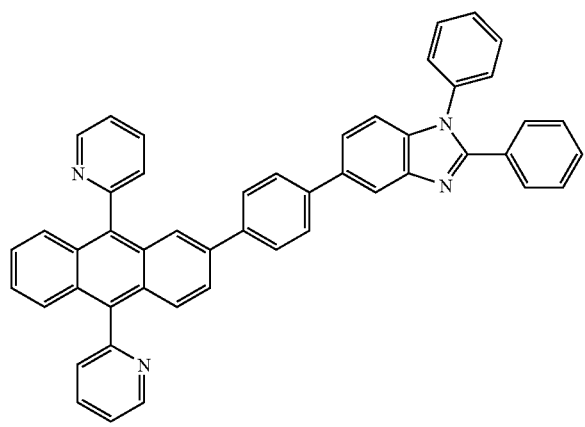
1-36
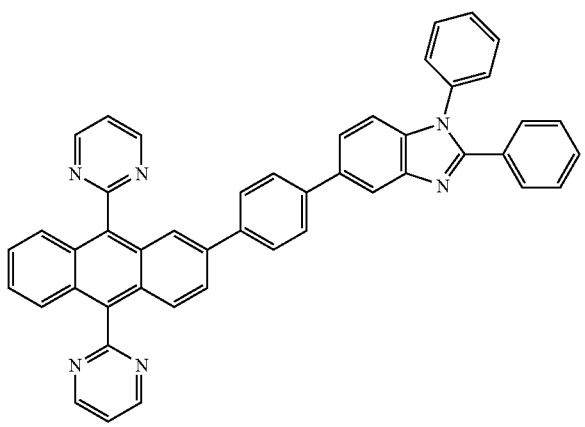
1-37
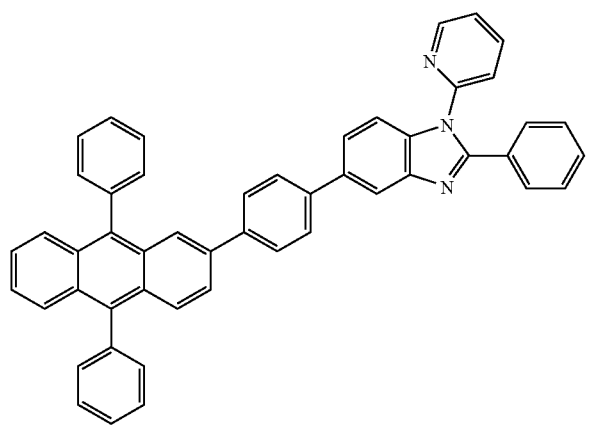
1-38
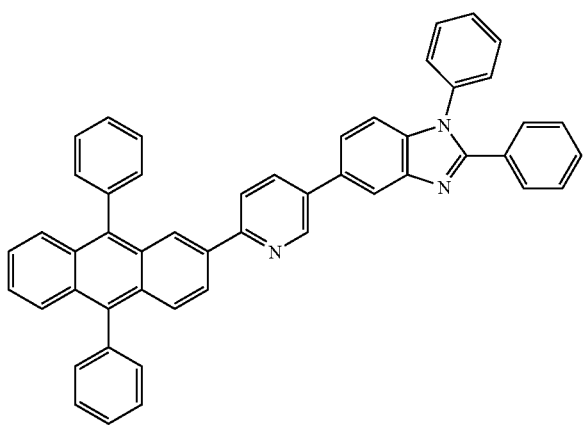
1-39
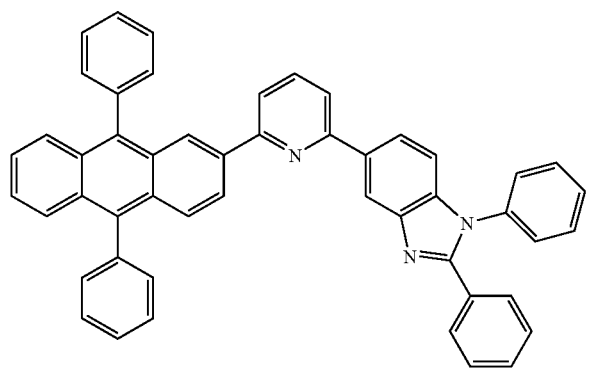
1-40
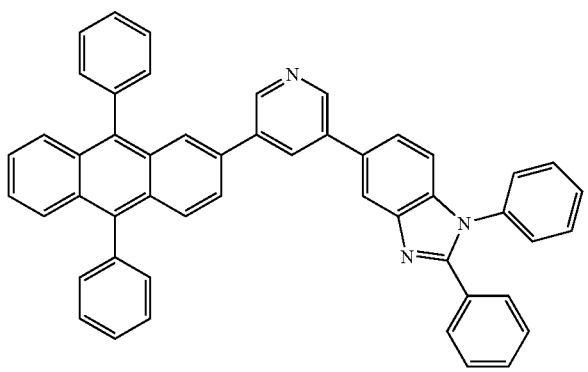

-continued
1-41
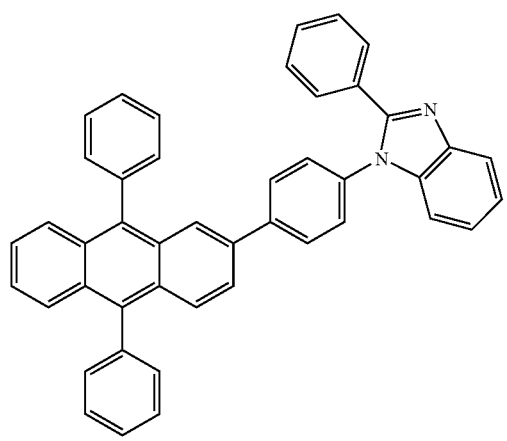
1-42
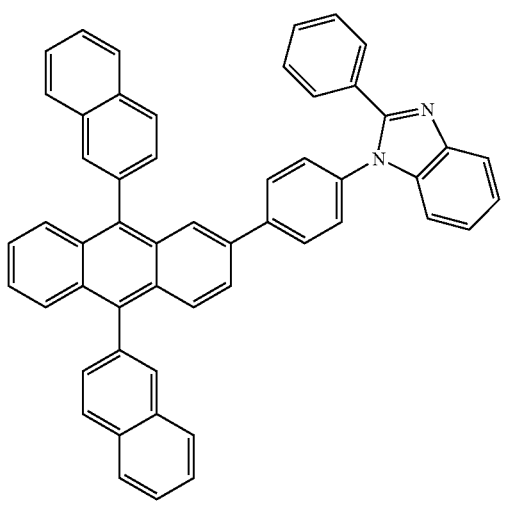
1-43
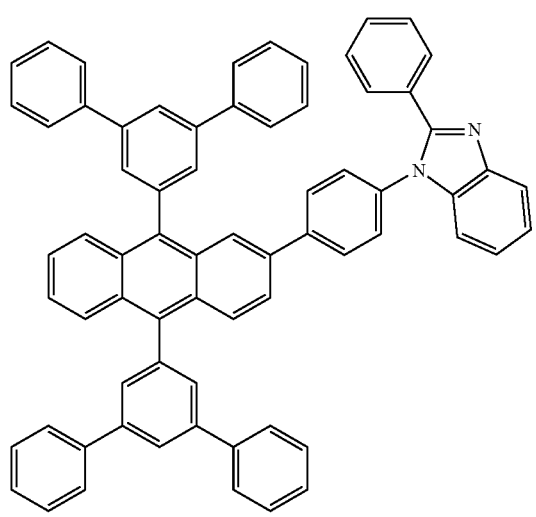
1-44
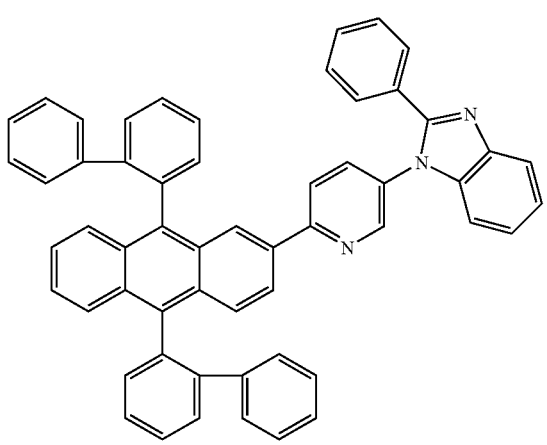
1-45
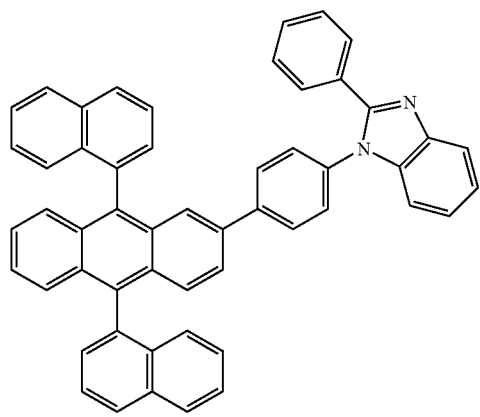
1-46
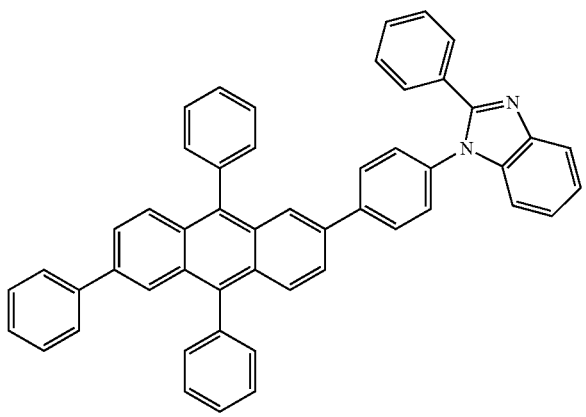

-continued
1-47
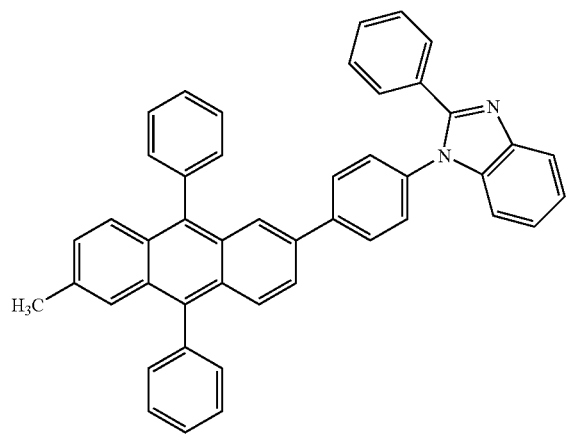
1-48
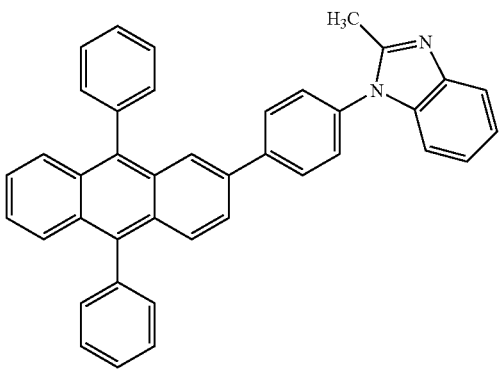
1-49
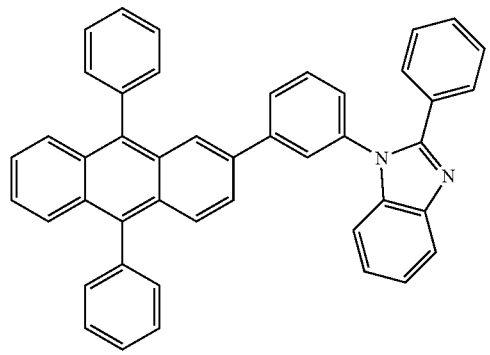
1-50
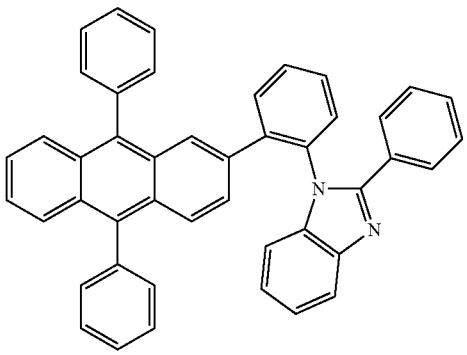
1-51
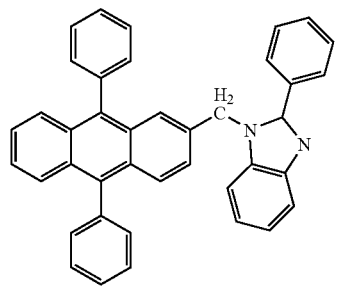
1-52
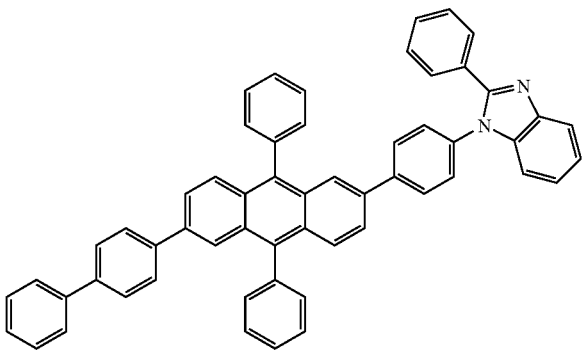
1-53
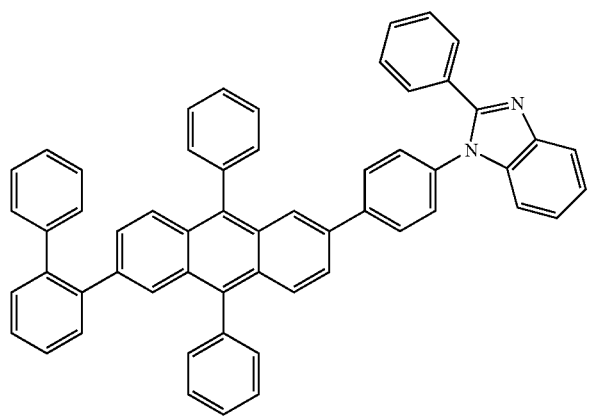
1-54
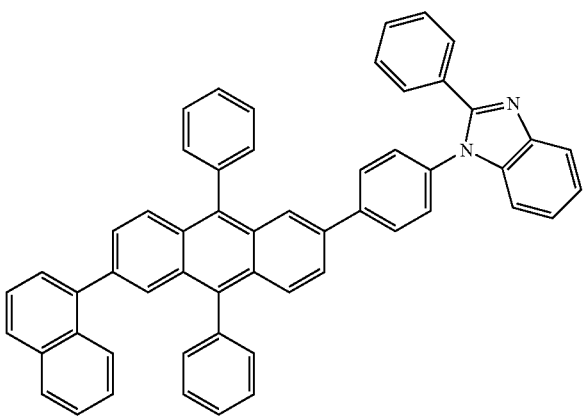

1-55
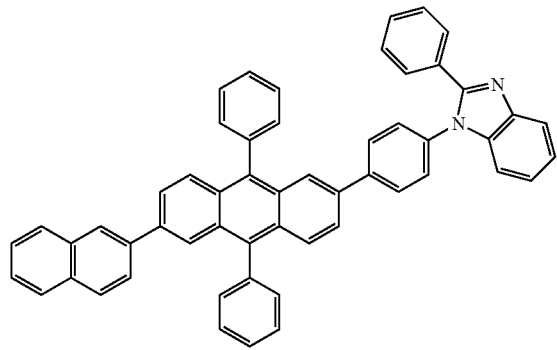
1-56
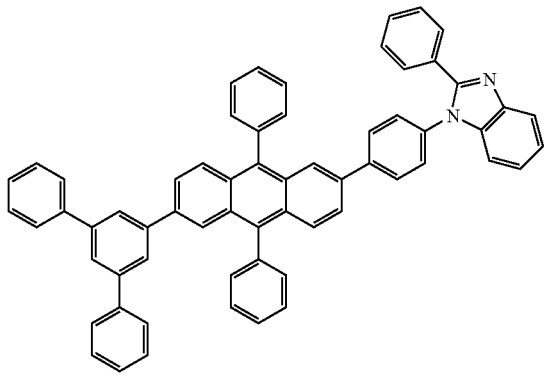
1-57
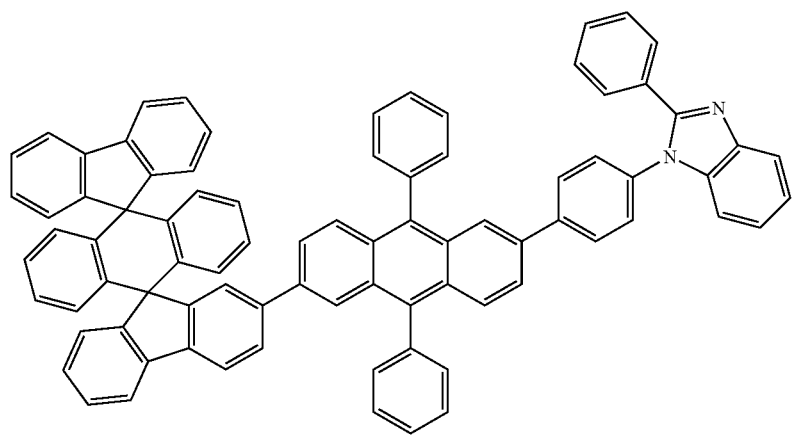
1-58
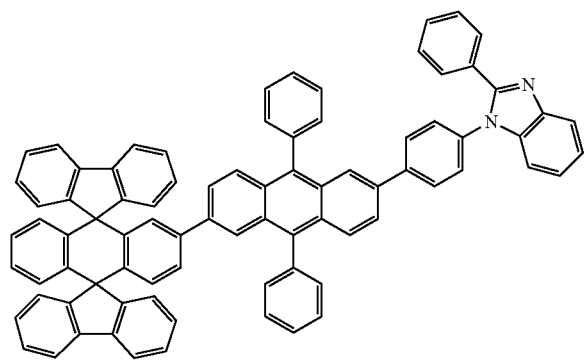
1-59
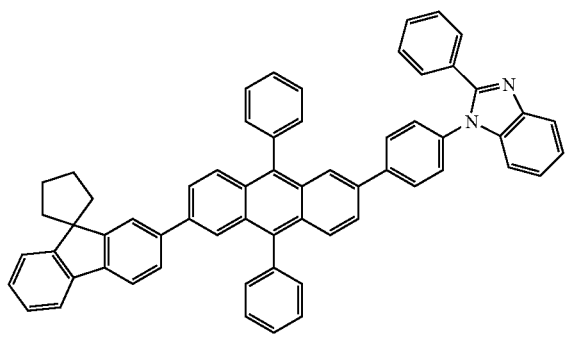

-continued
1-60
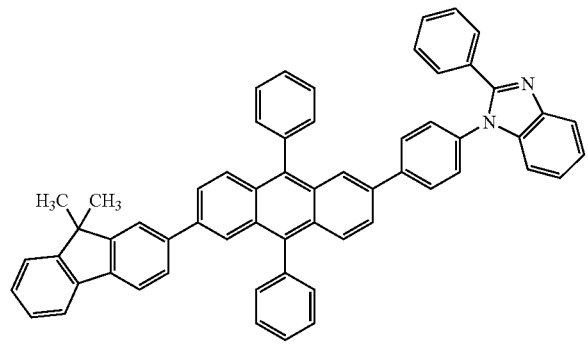
1-61
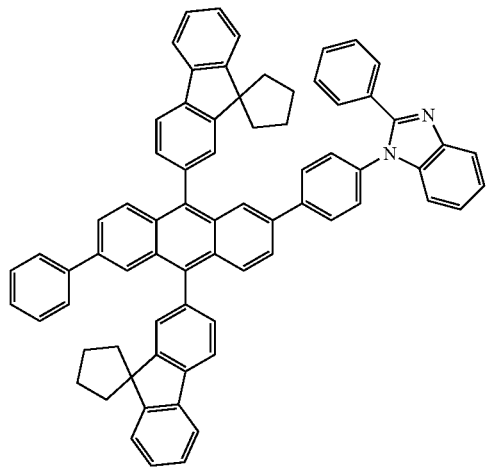
1-62
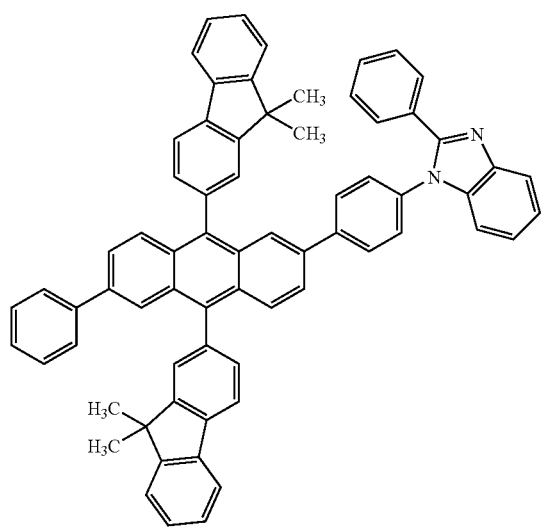
1-63
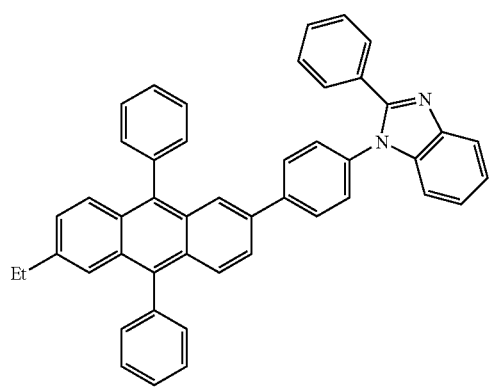
1-64
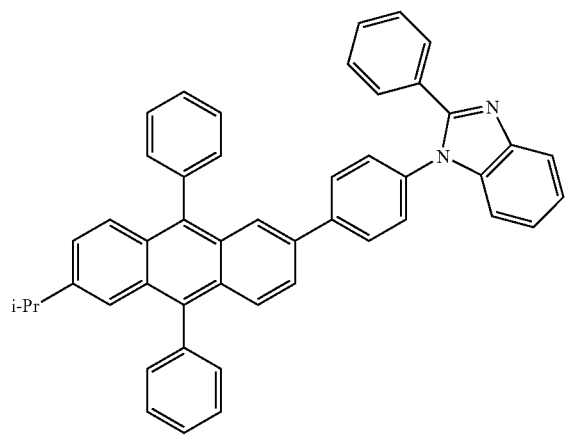
1-65
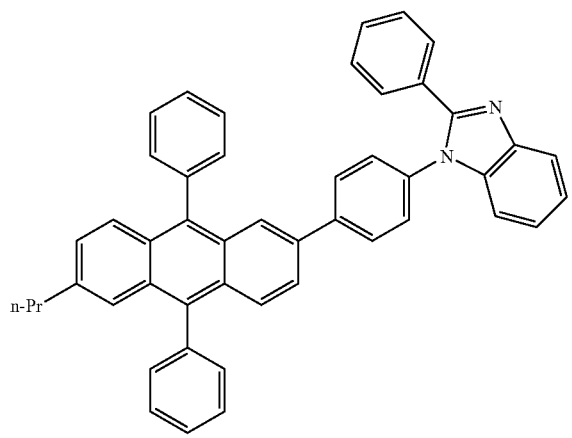

-continued
1-66
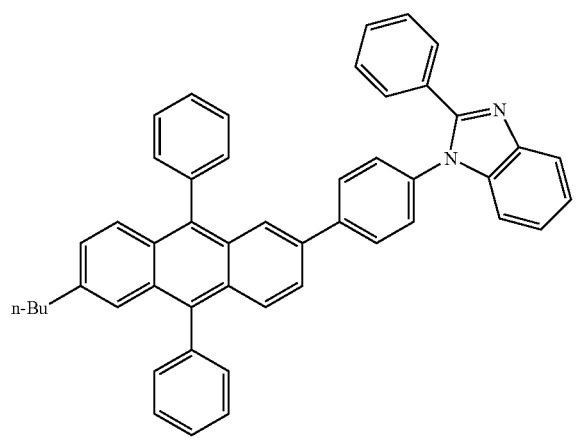
1-67
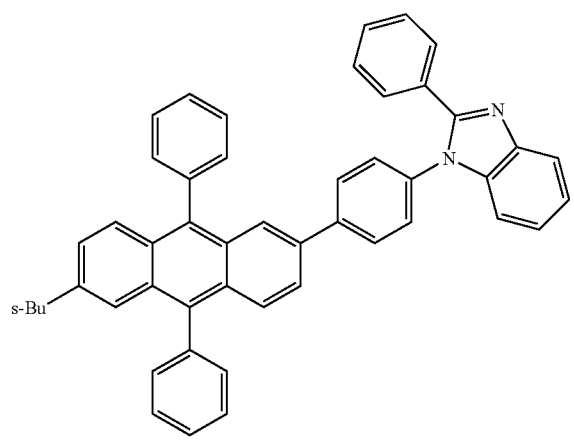
1-68
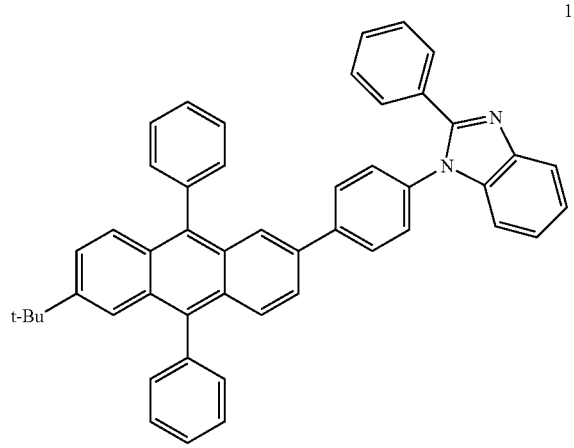
1-79
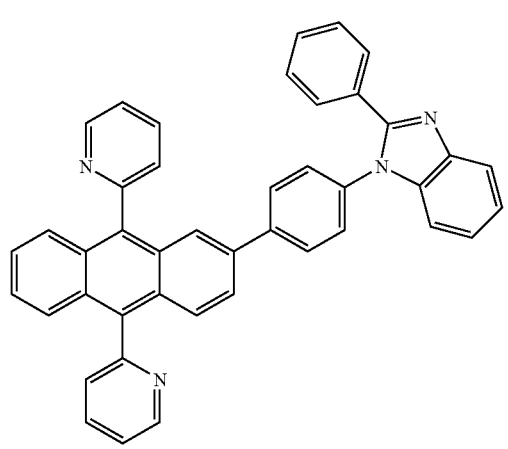
1-70
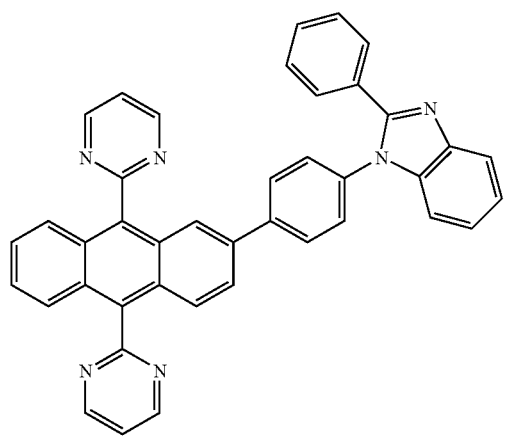
1-71
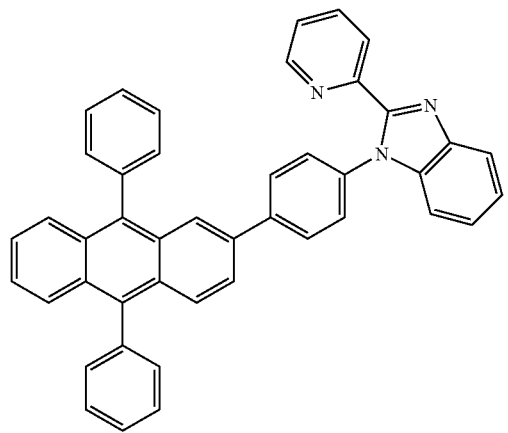

-continued
1-72
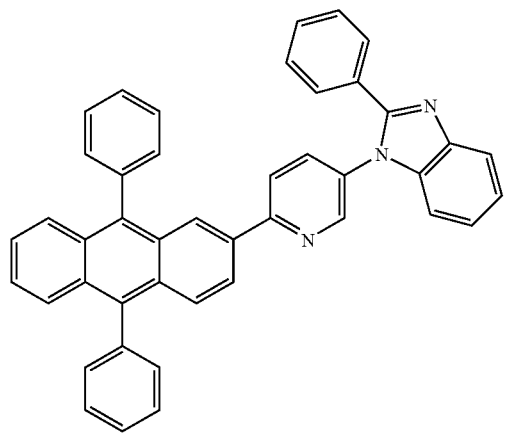
1-73
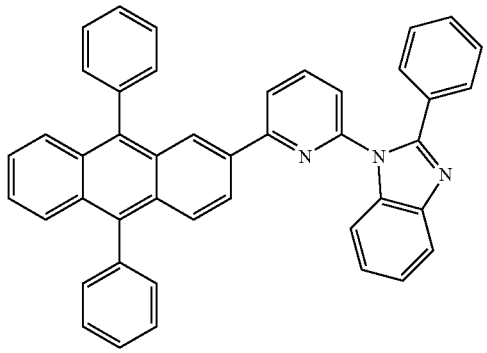
1-74
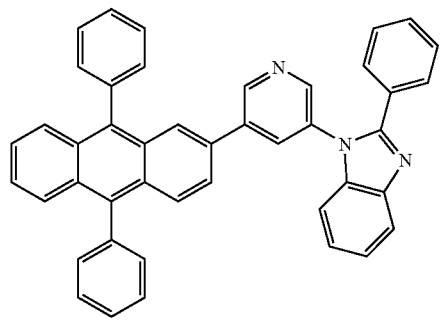
1-75
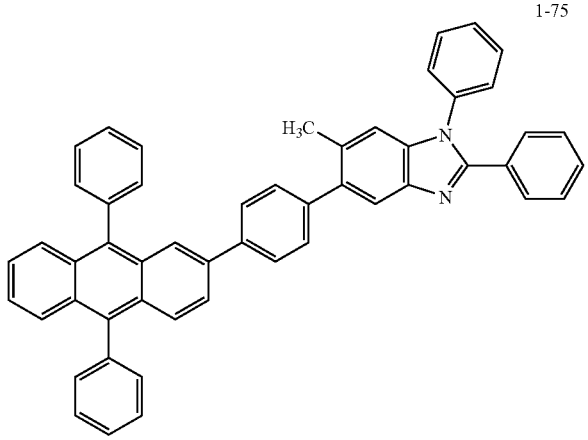
1-76
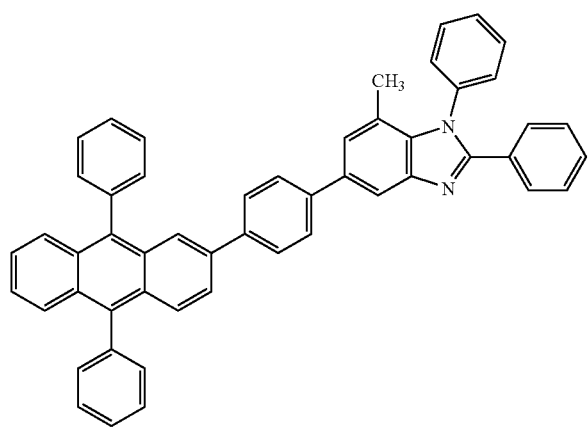
1-77
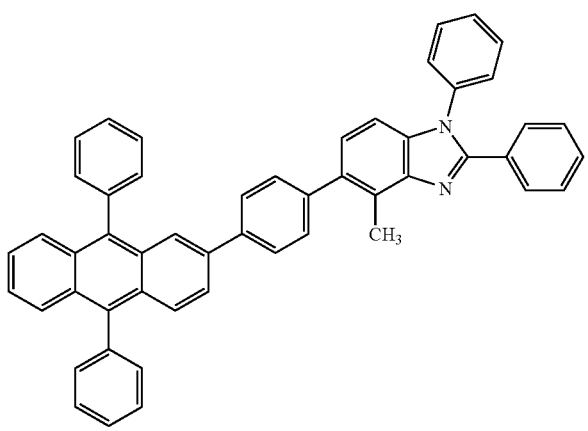

-continued
1-78
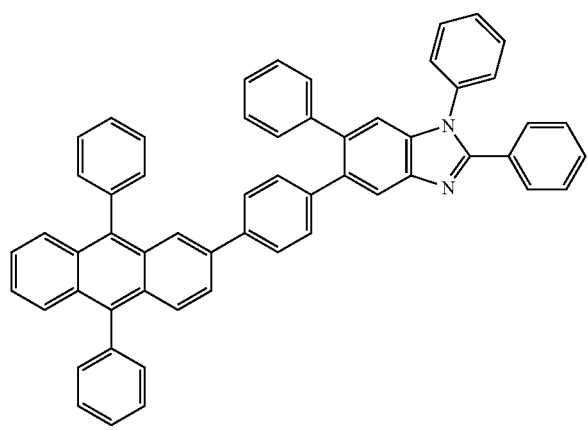
1-79
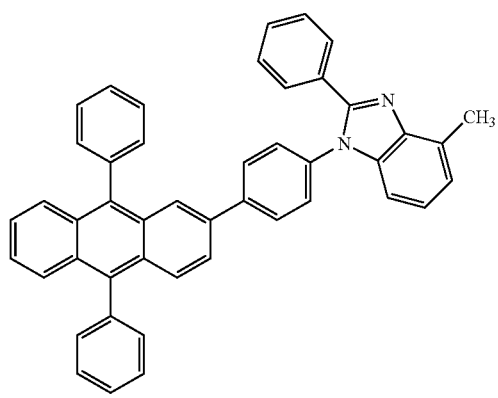
1-80
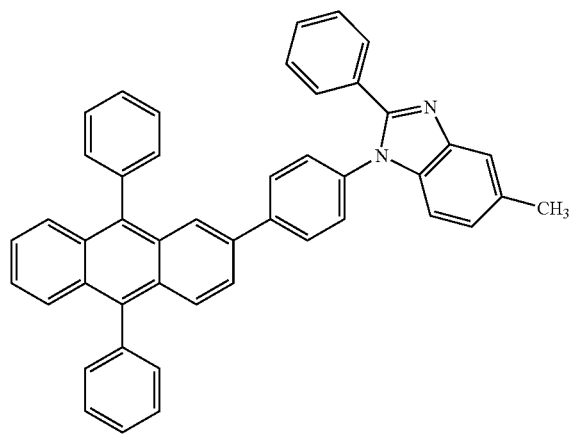
1-81
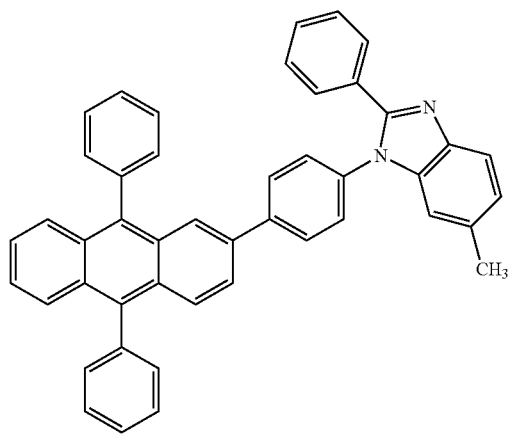
1-82
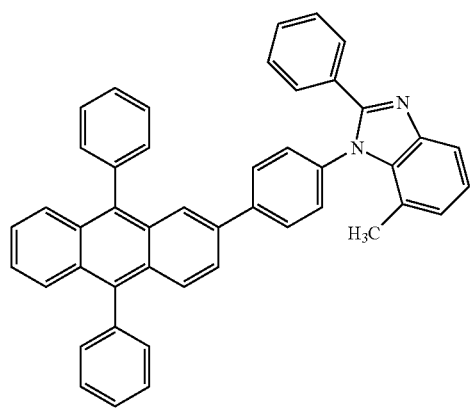
1-83
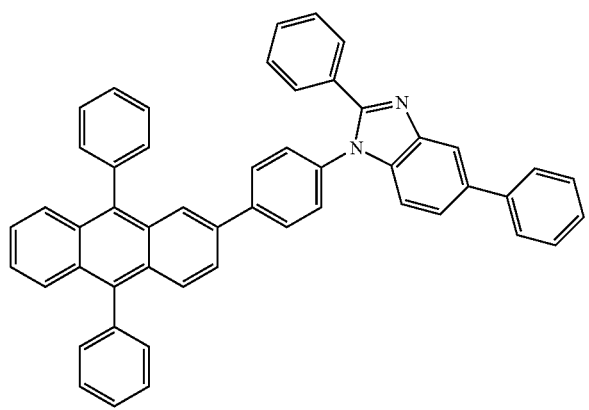

-continued
1-84
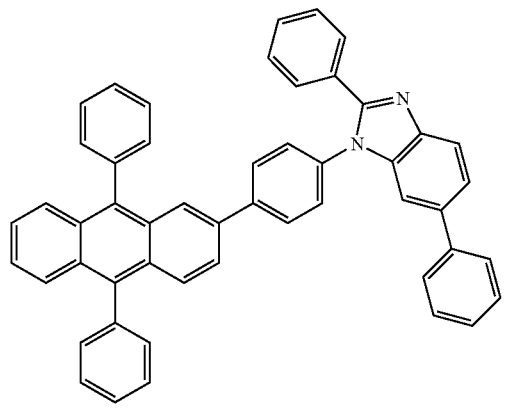
1-85
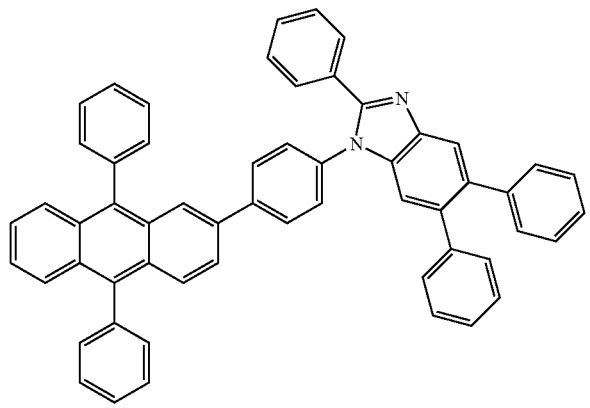
2-1
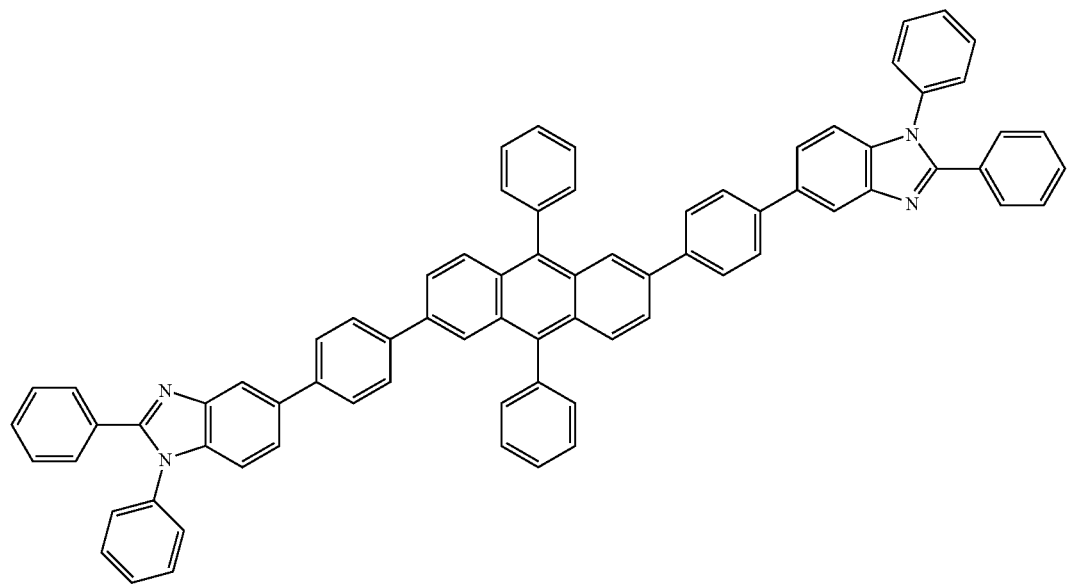
2-2
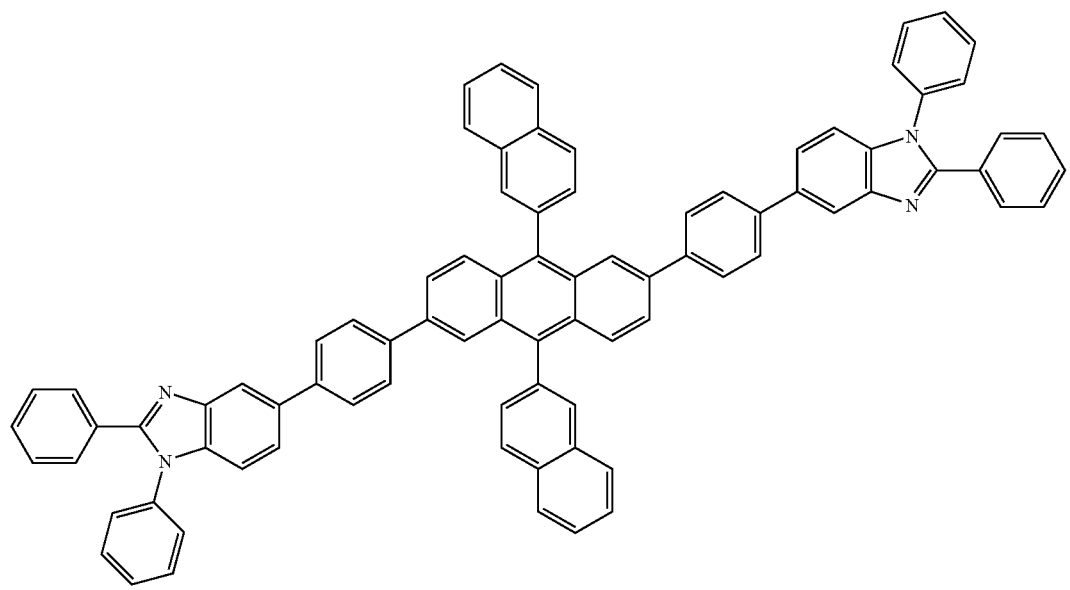

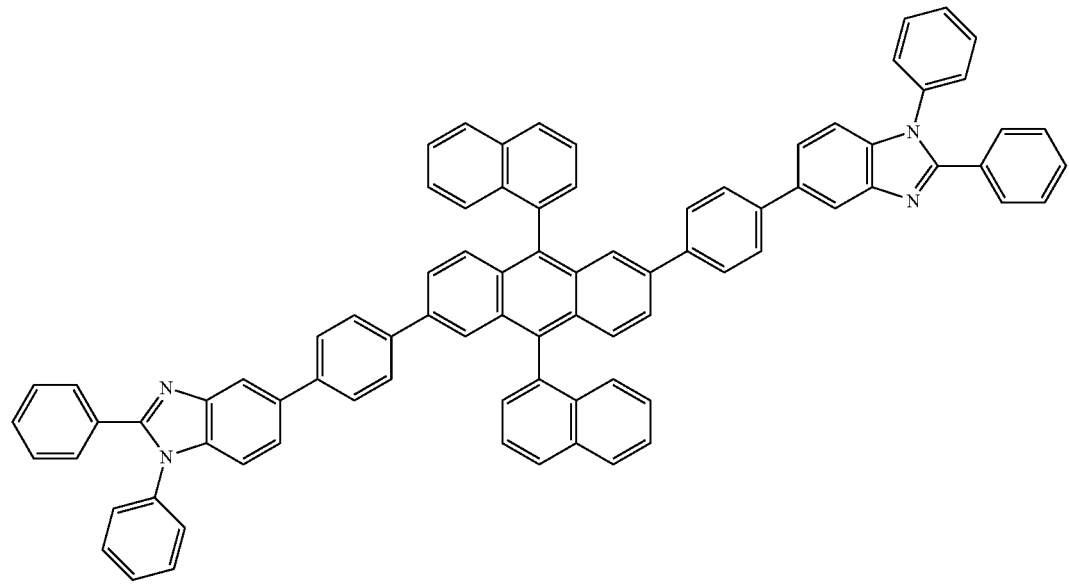
2-3
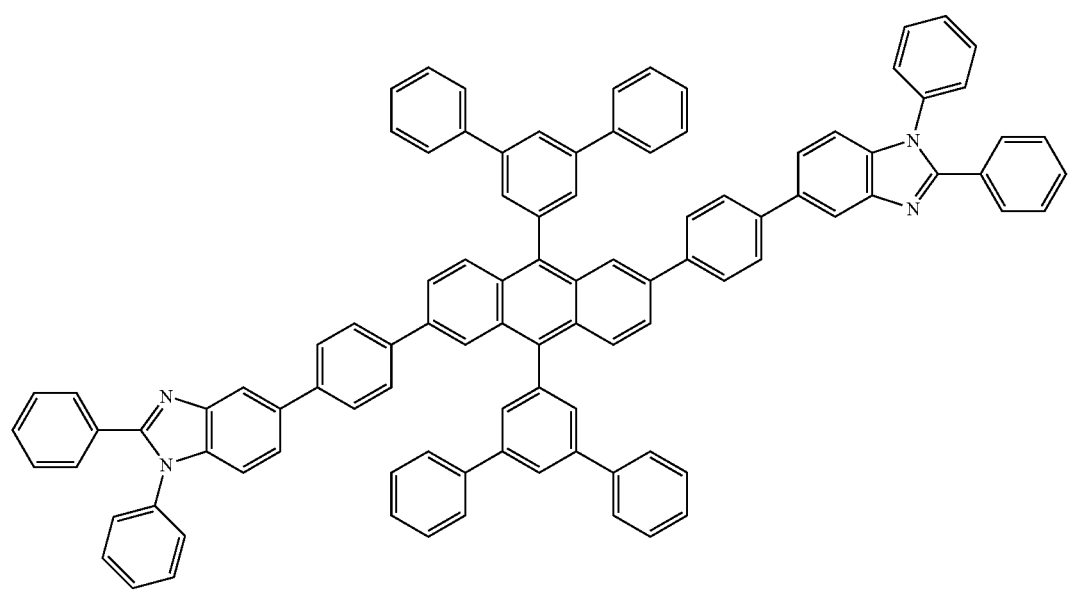
2-4

2-5
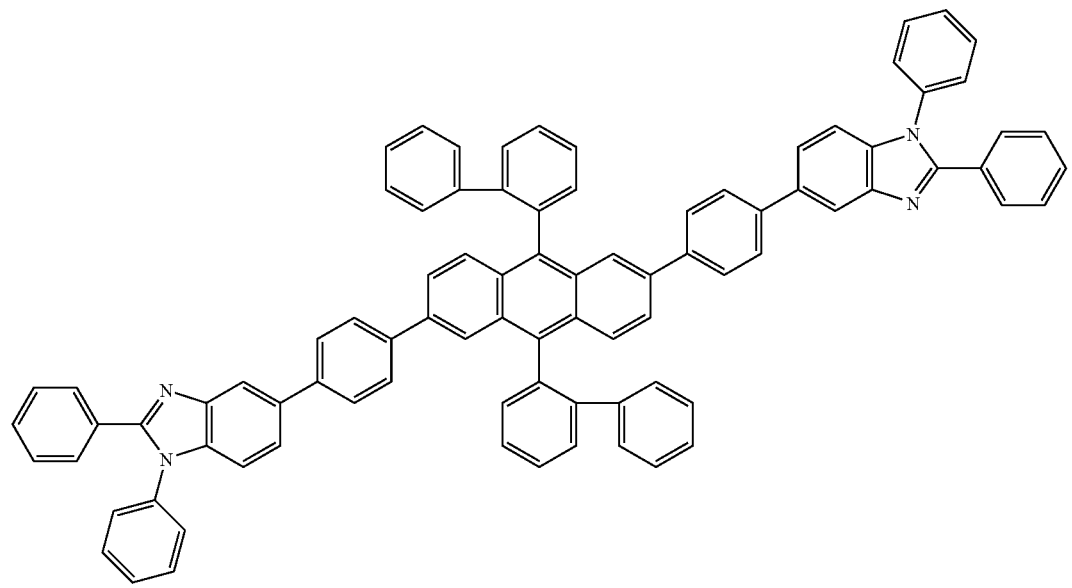
2-6
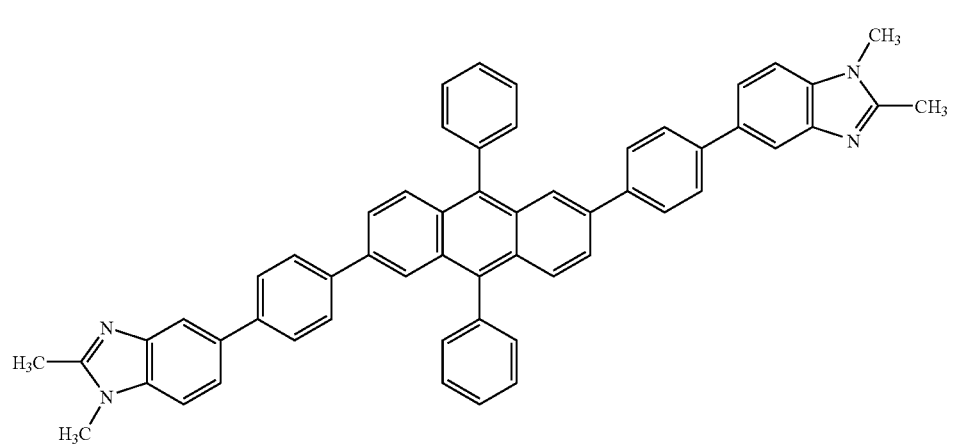
2-7
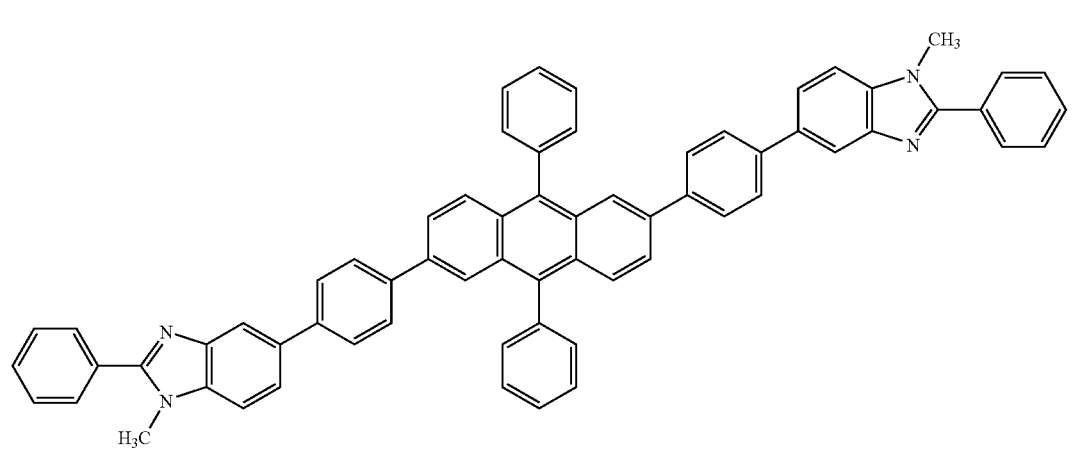

-continued
2-8
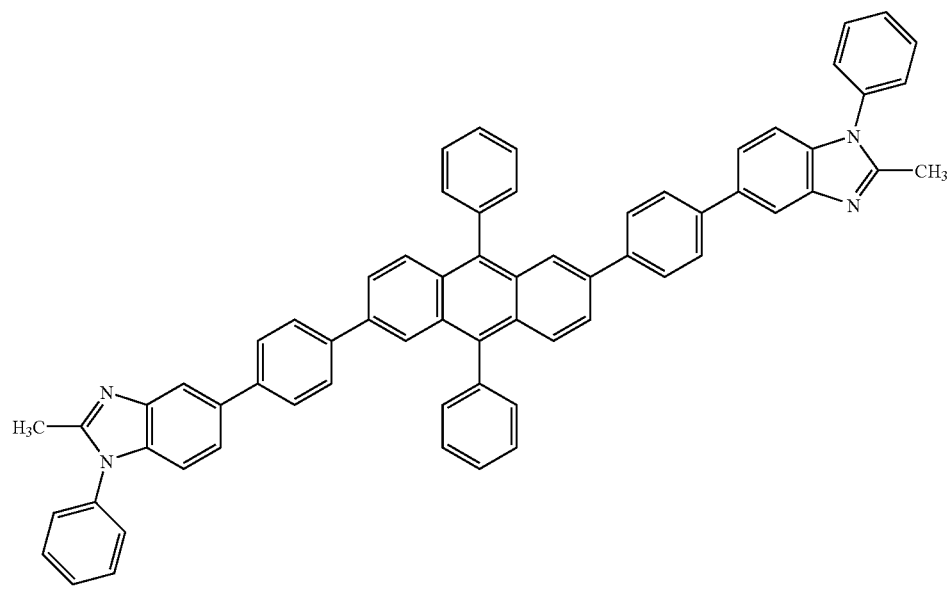
2-9
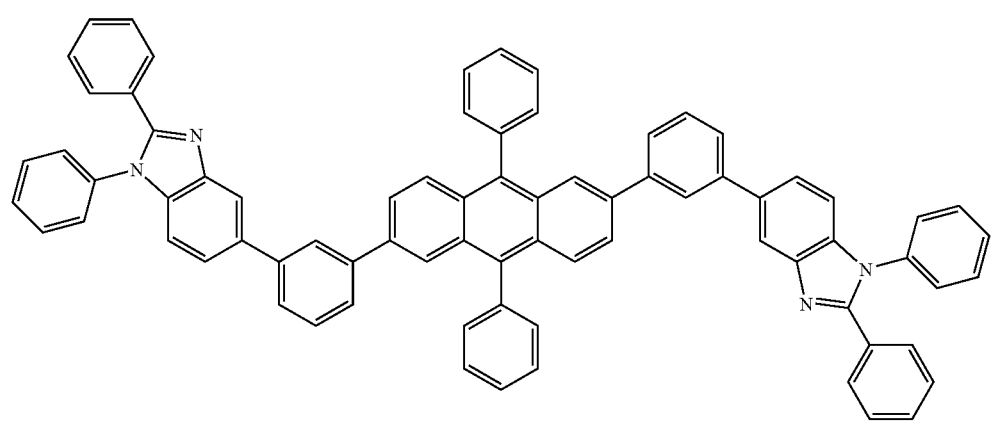
2-10 2-11
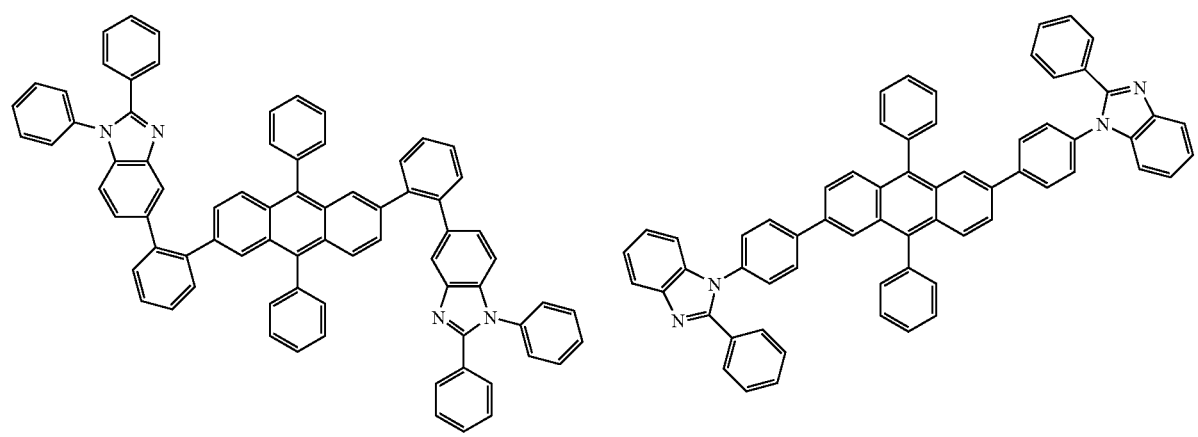

-continued
2-12
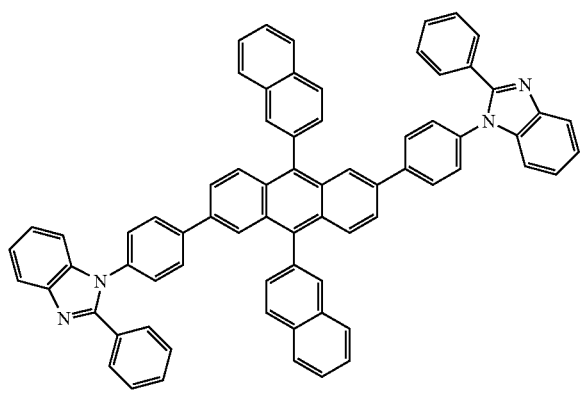
2-13
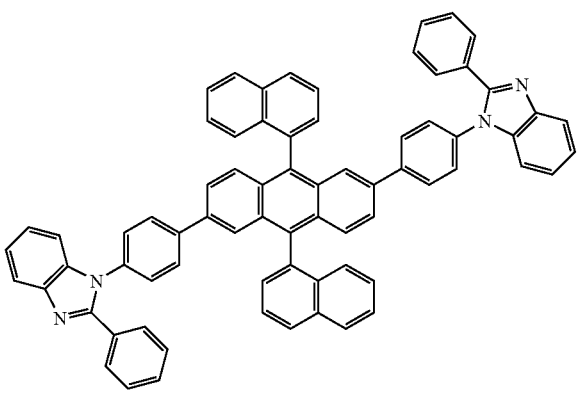
2-14
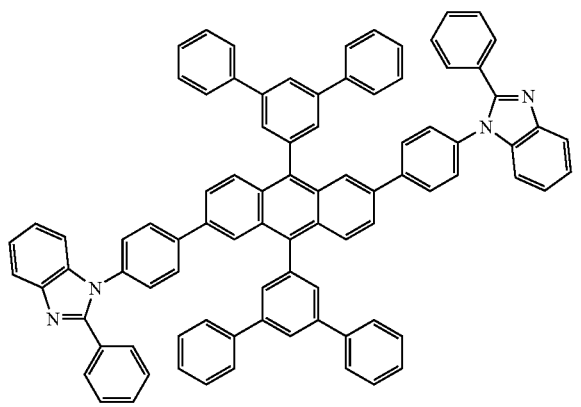
2-15
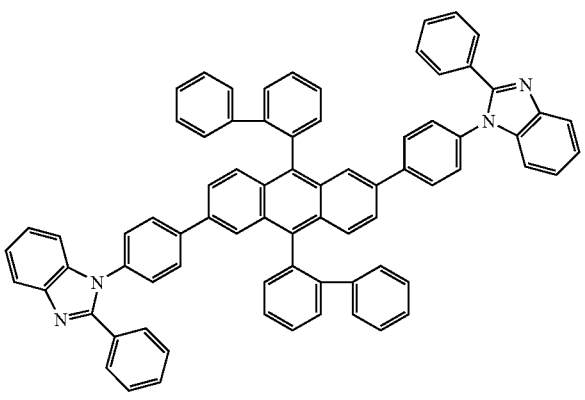
2-16
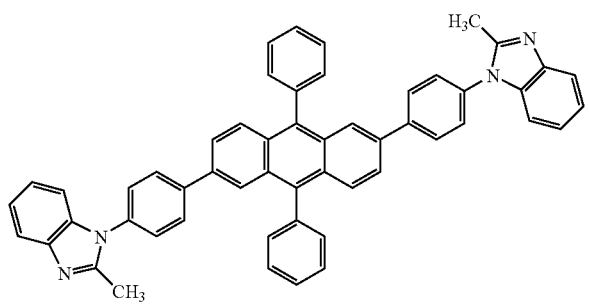
2-17
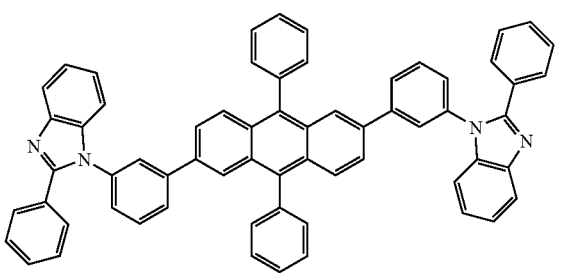
2-18
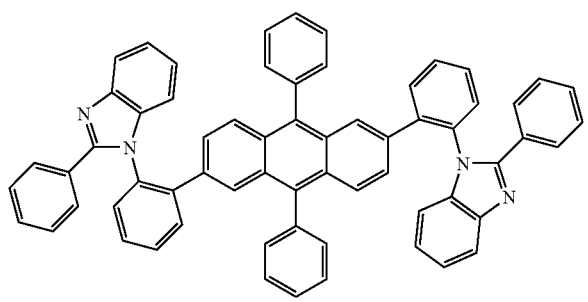
2-19
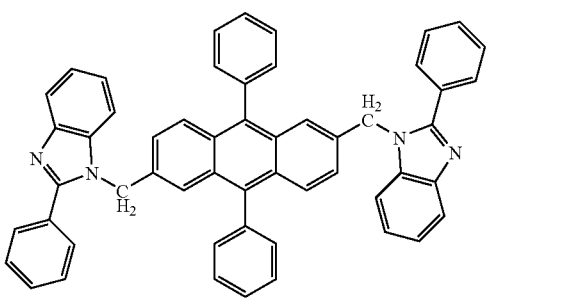

2-20
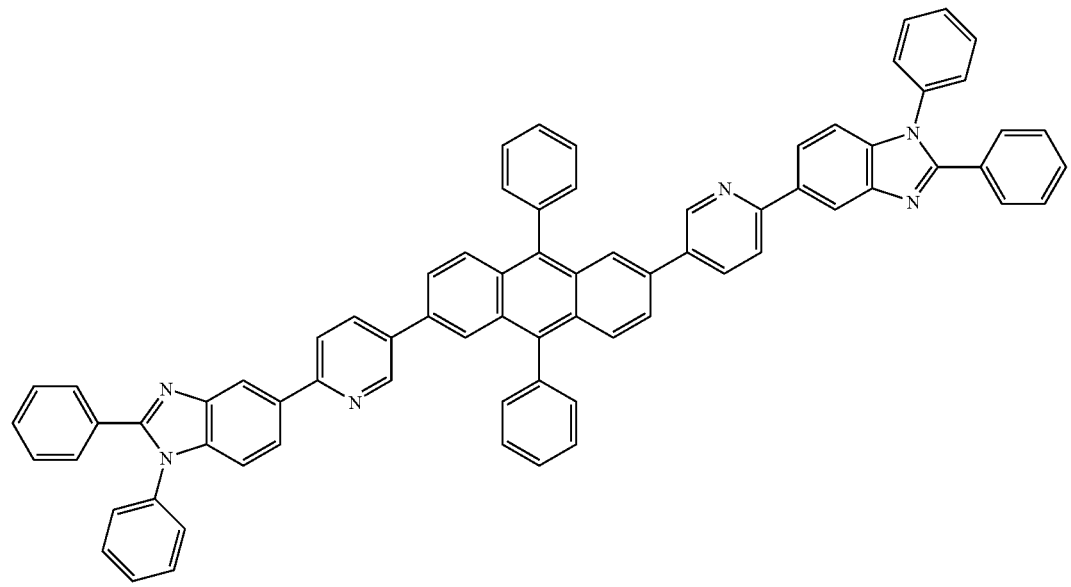
2-21
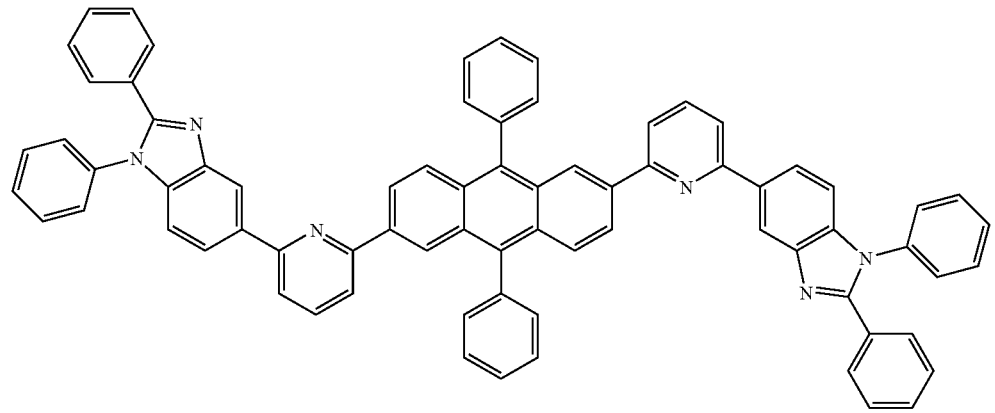
2-22
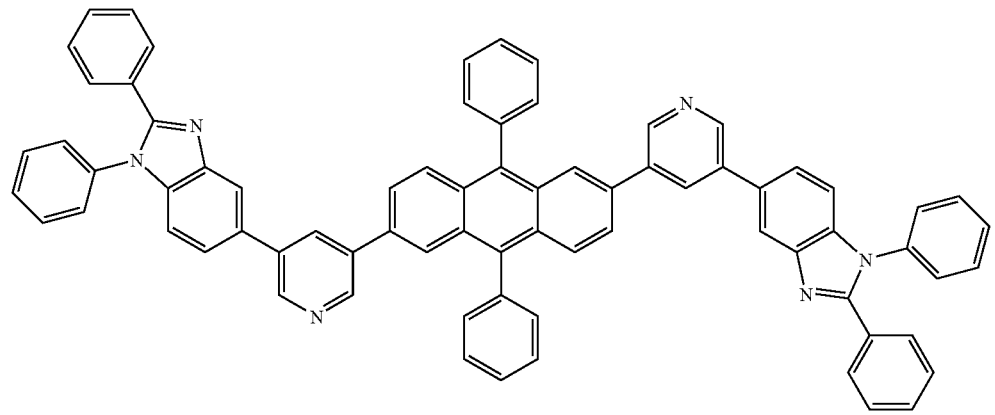

-continued
2-23
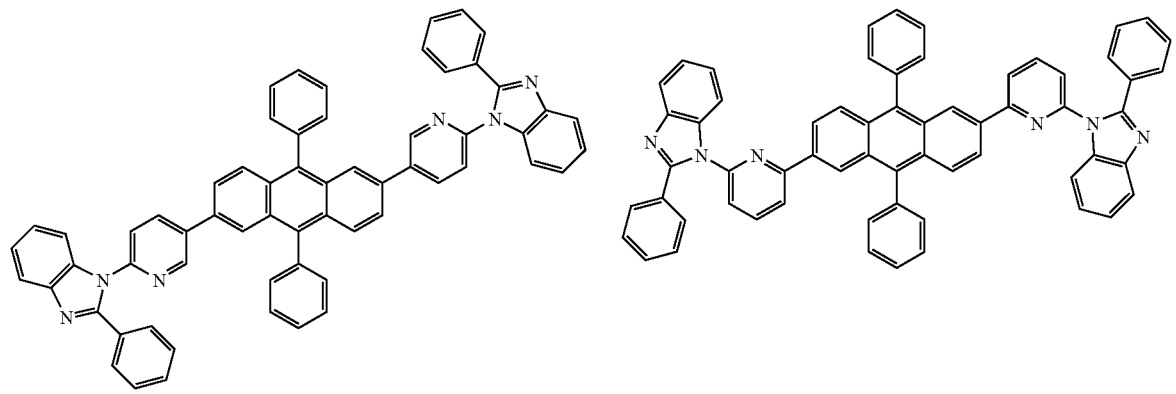
2-24
2-25
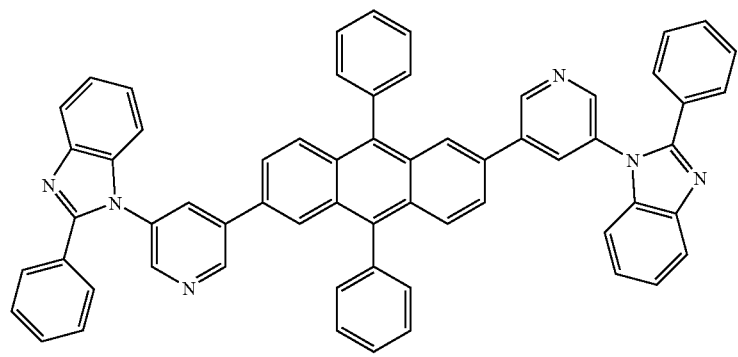
2-26
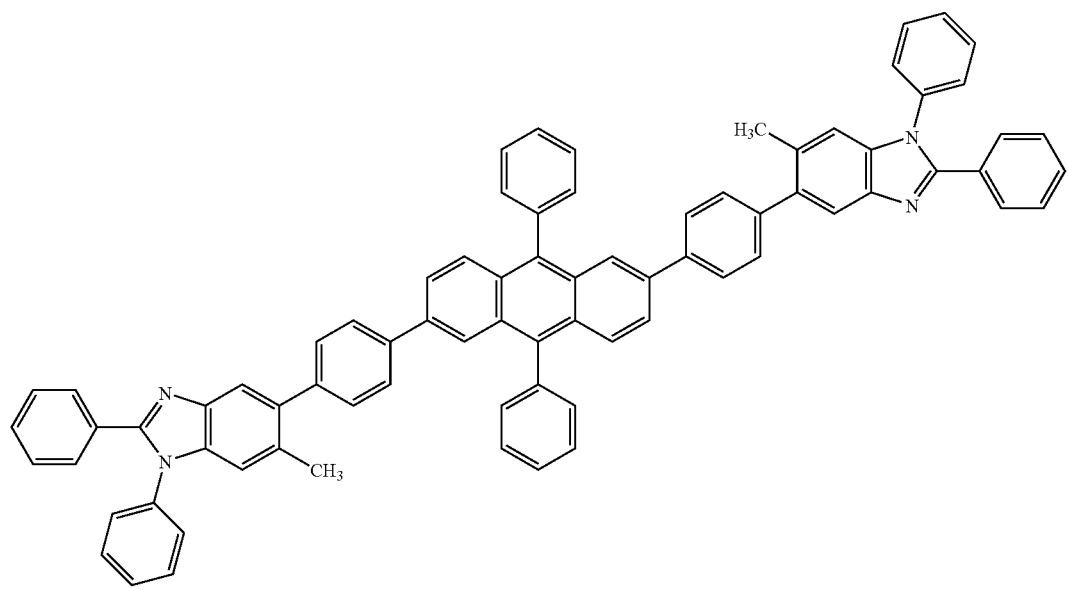

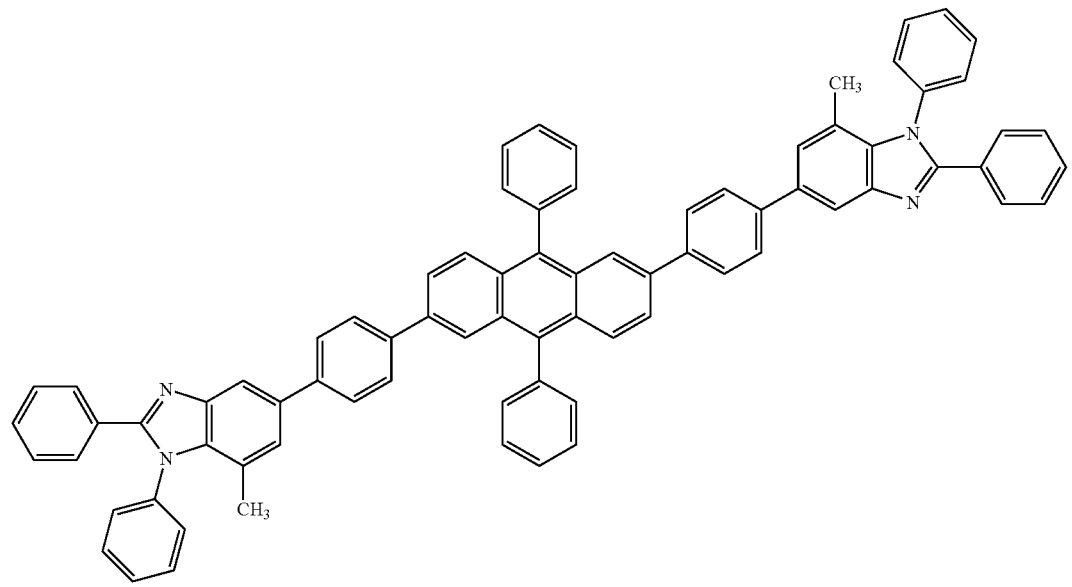
2-27
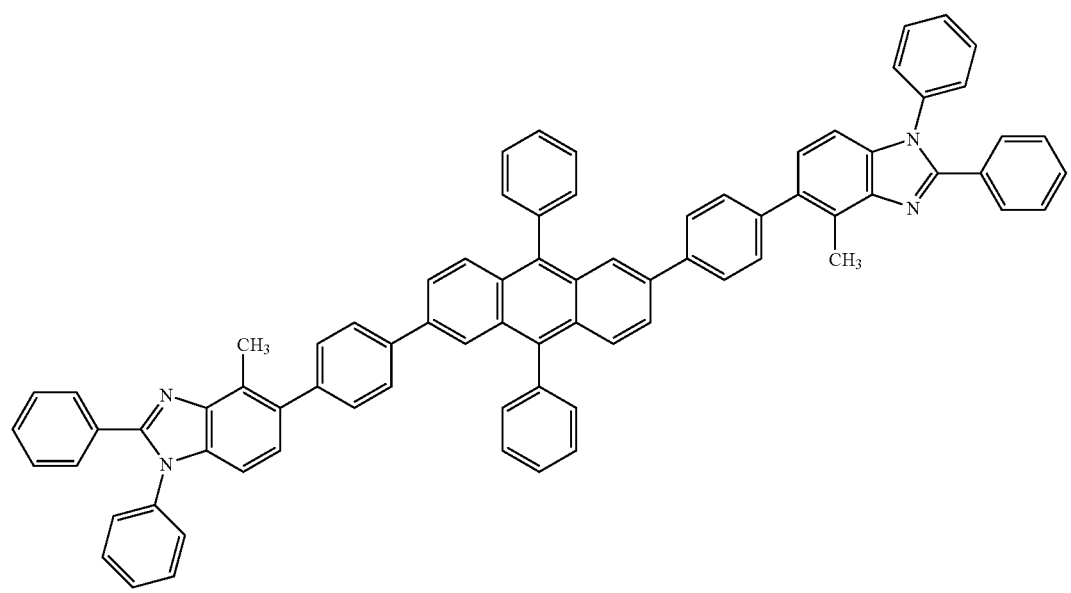
2-28

2-29
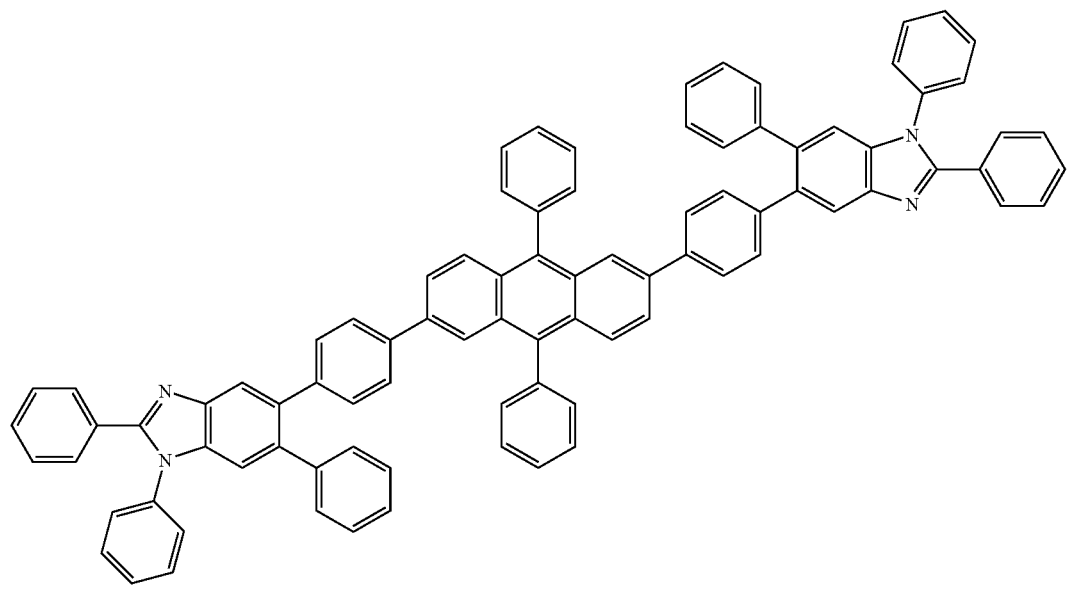
2-30
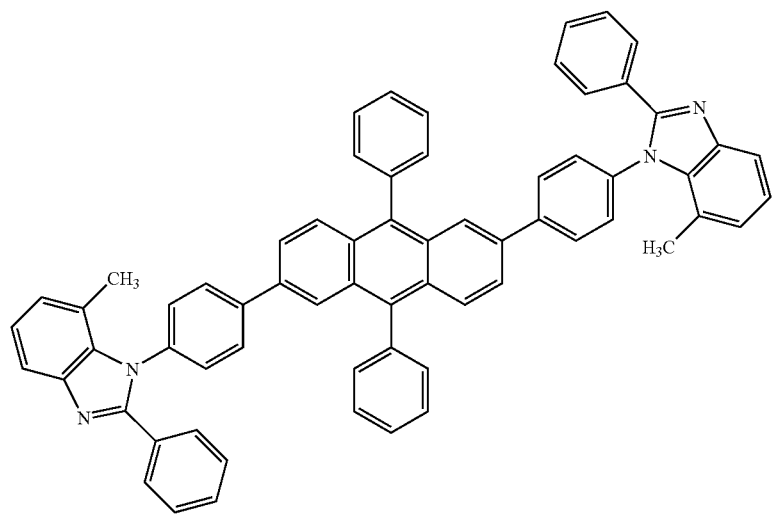
2-31
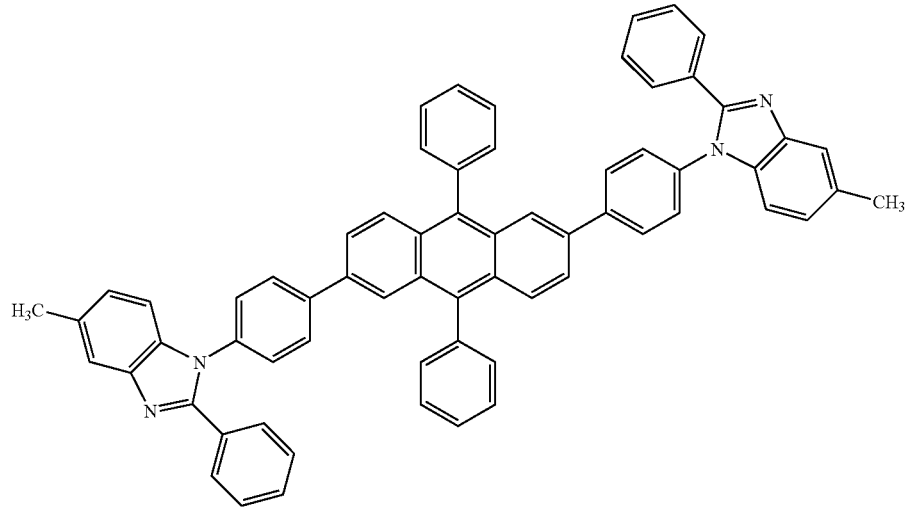

-continued
2-32
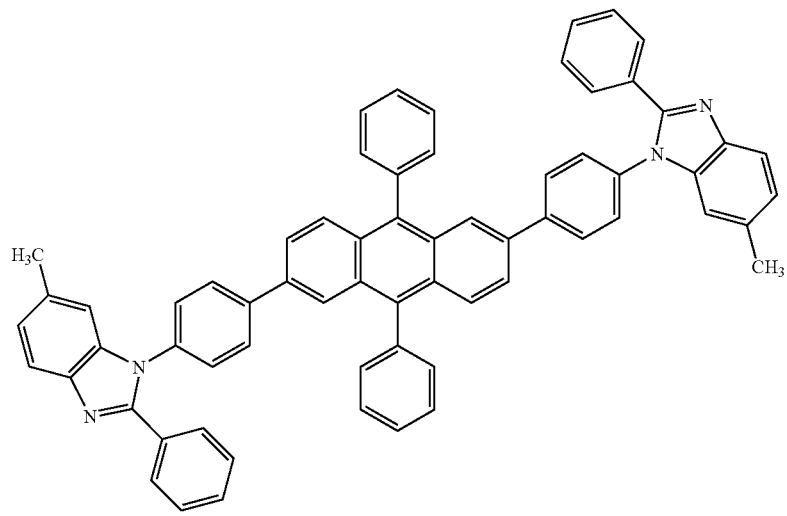
2-33
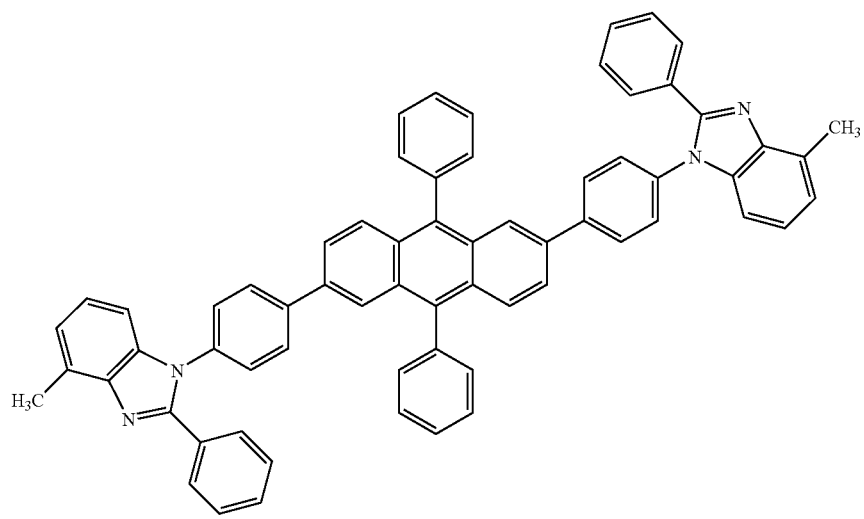
2-34
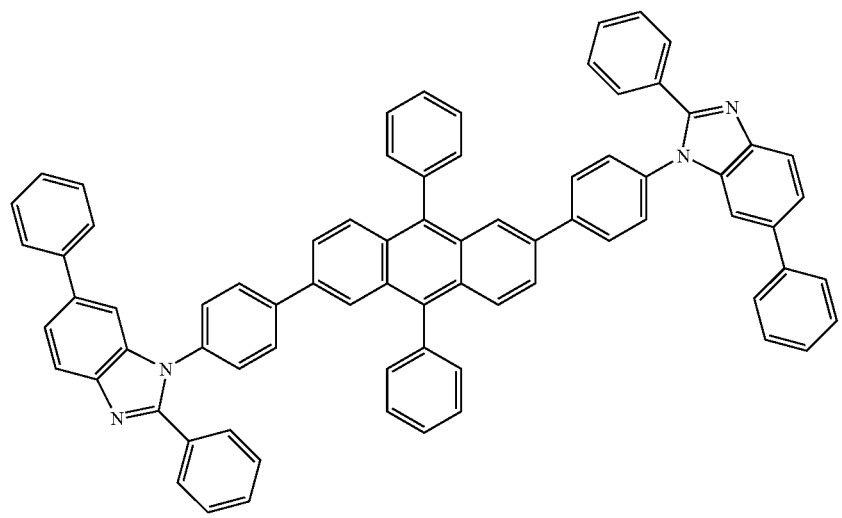

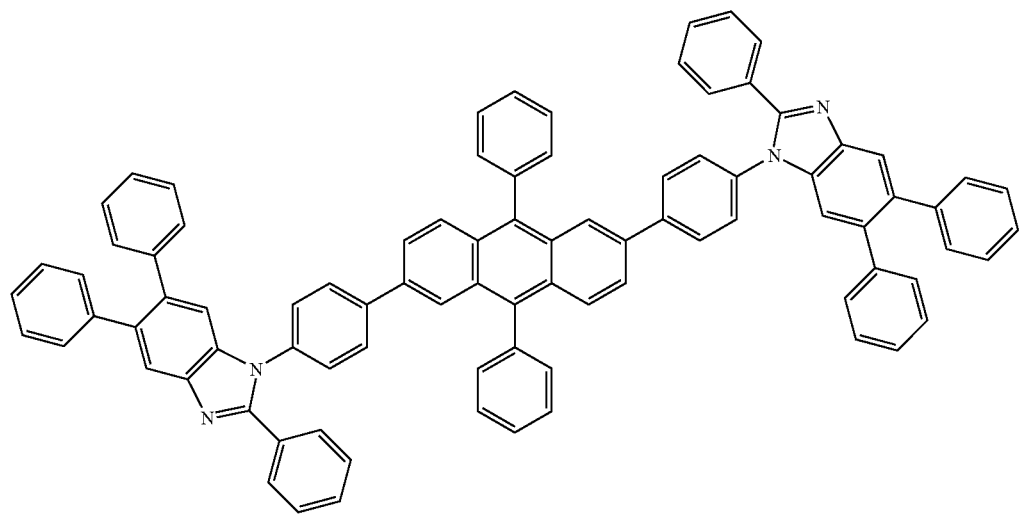
2-35
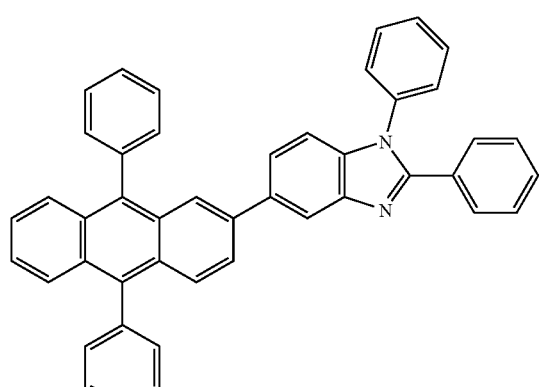
3-1
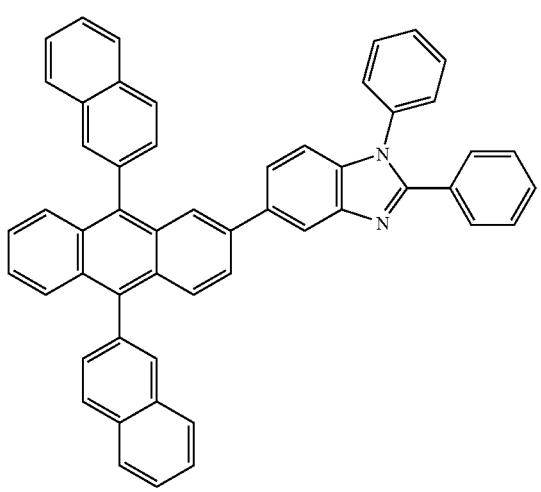
3-2
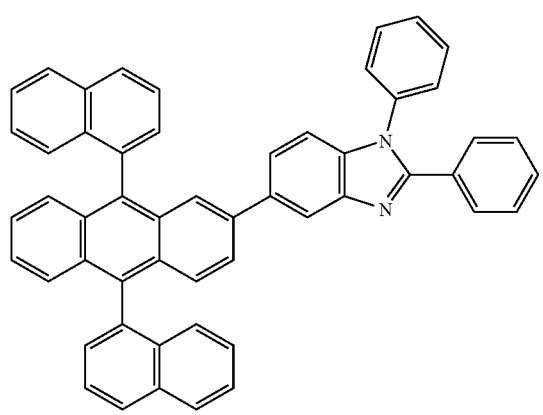
3-3
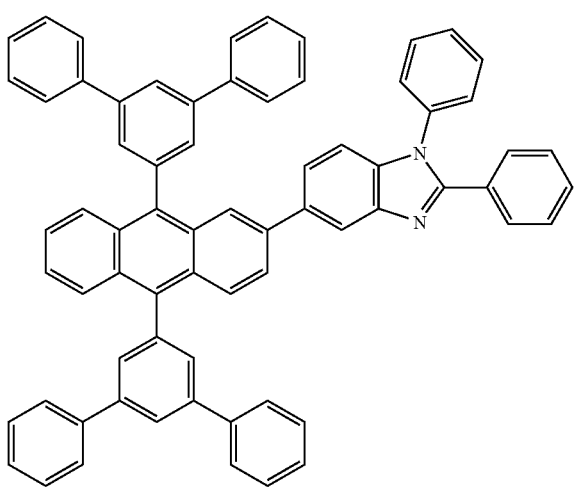
3-4

-continued
3-5
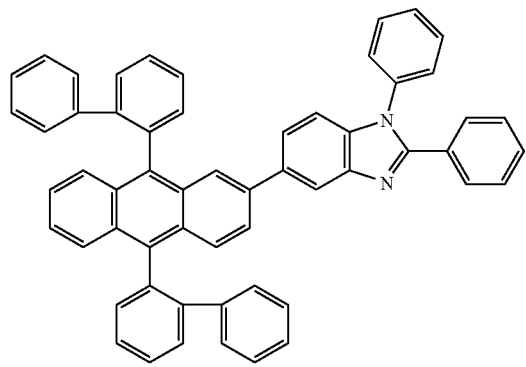
3-6
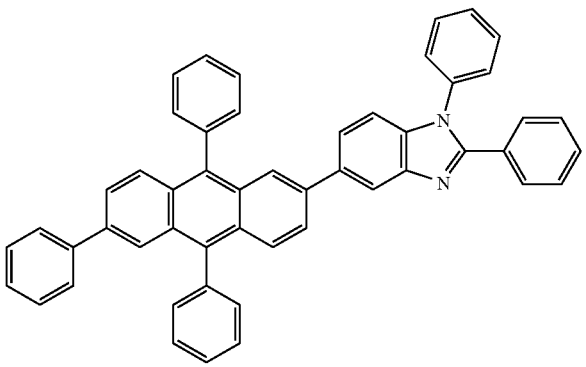
3-7
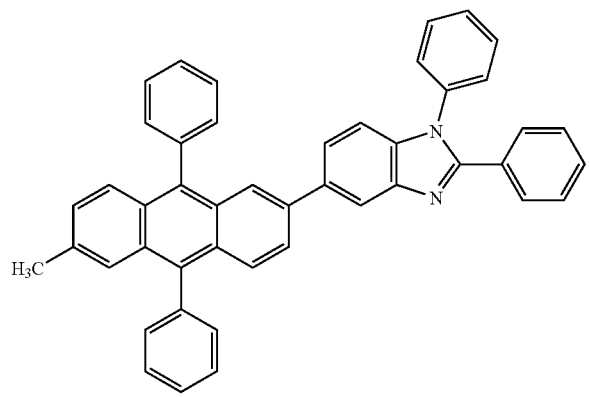
3-8
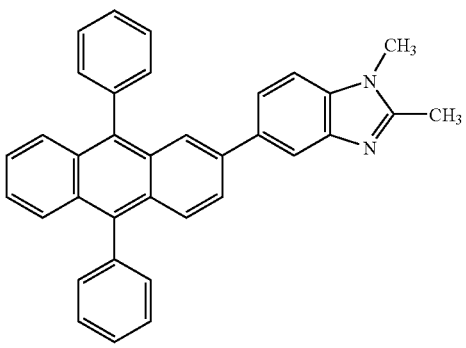
3-9
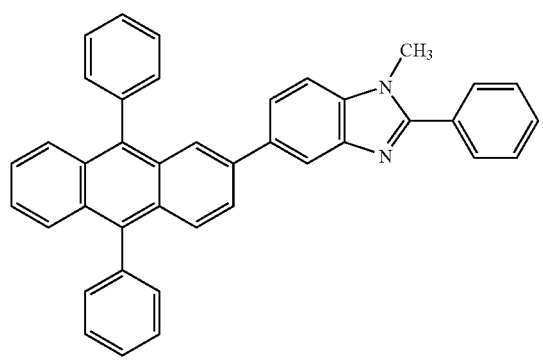
3-10
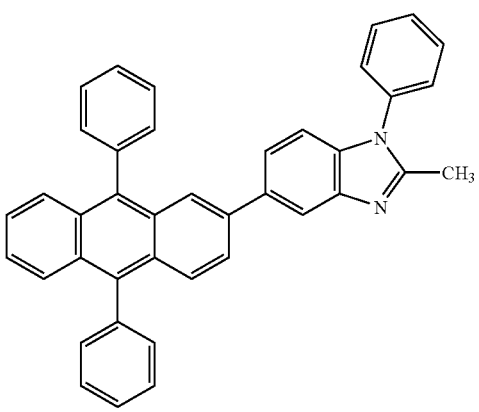
3-11
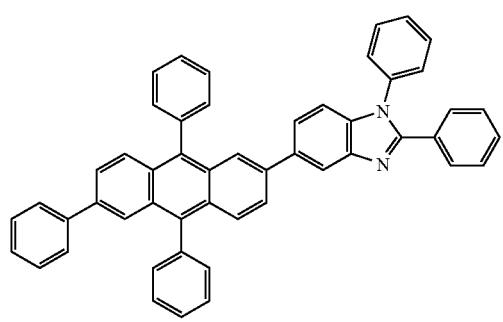
3-12
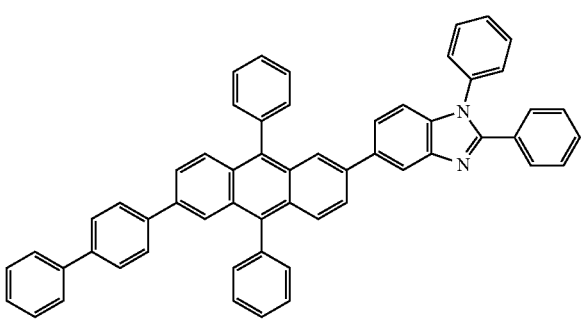

-continued
3-13
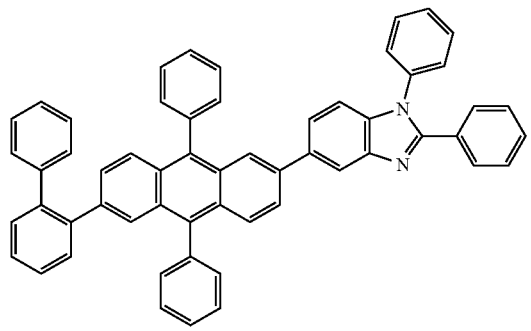
3-14
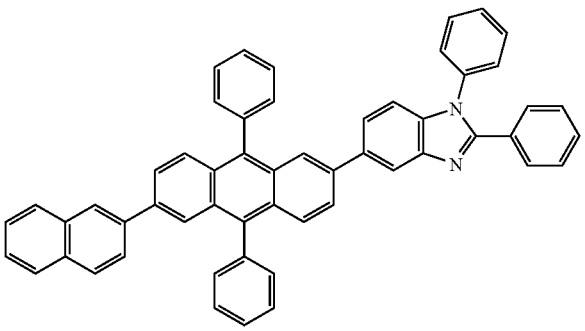
3-15
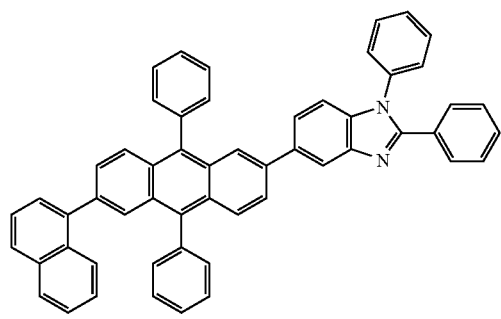
3-16
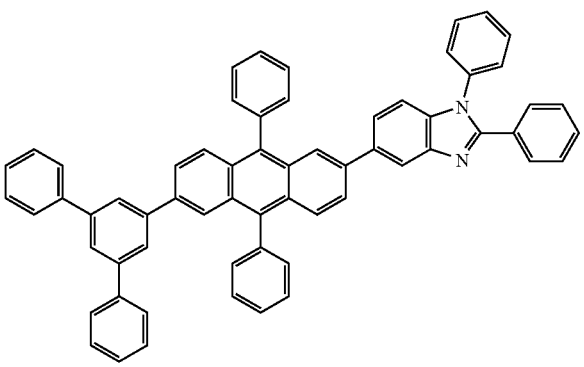
3-17
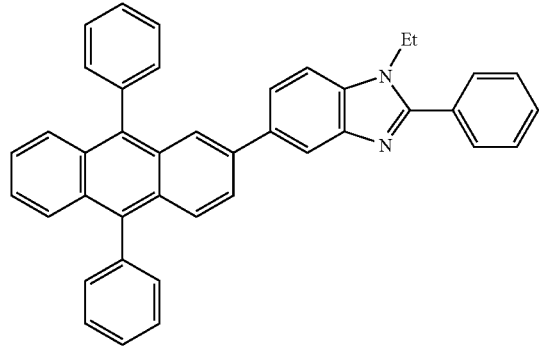
3-18
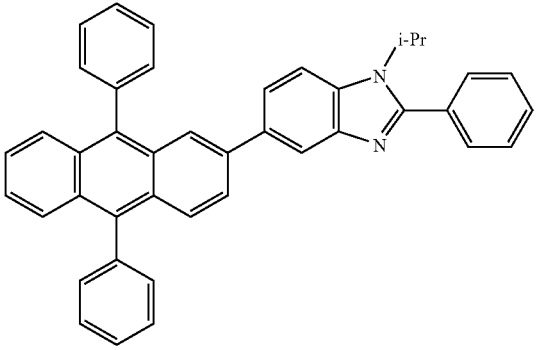
3-19
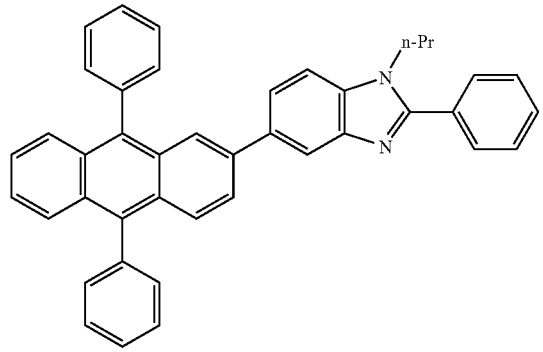
3-20
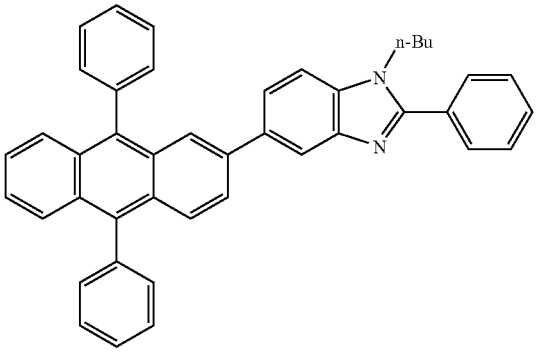

3-21
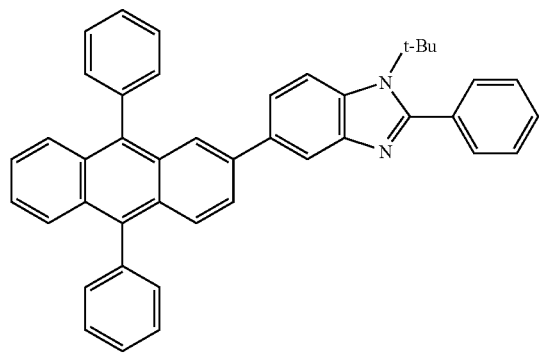
3-22
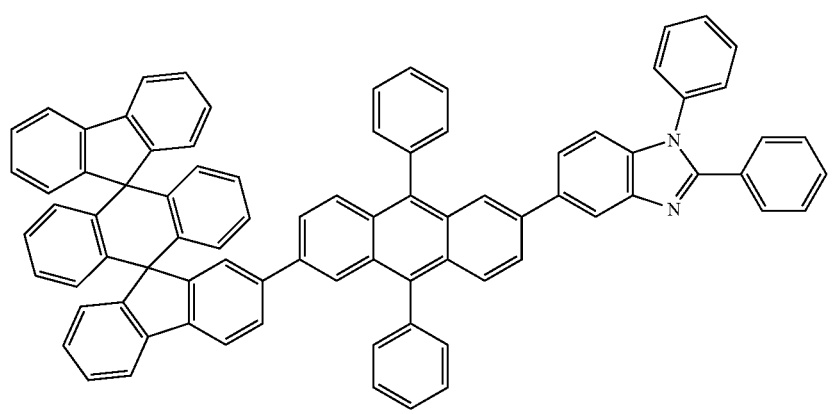
3-23
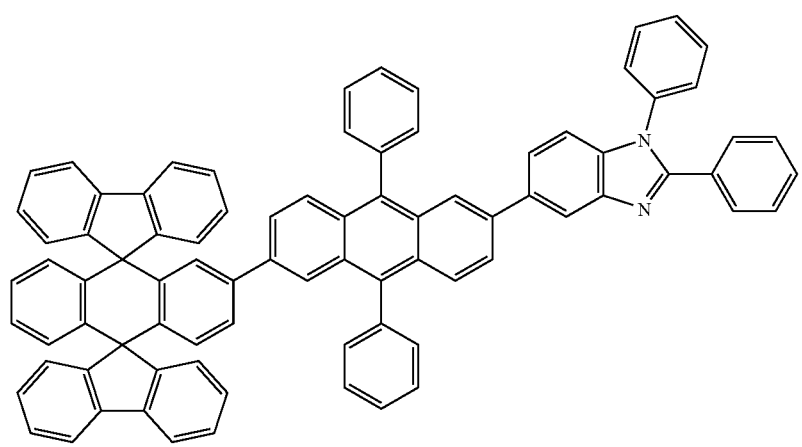
3-24
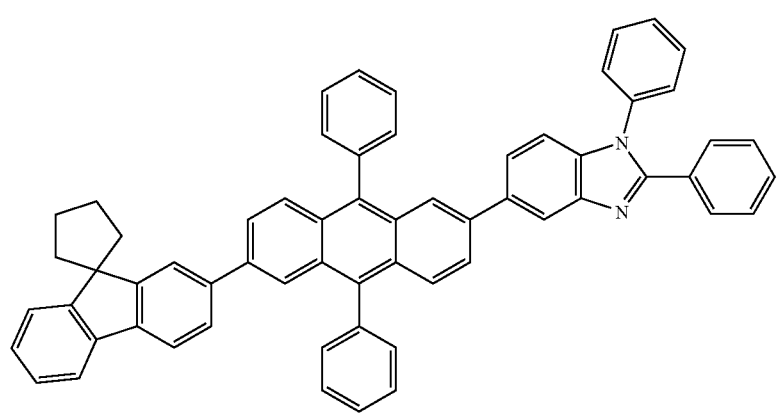

-continued
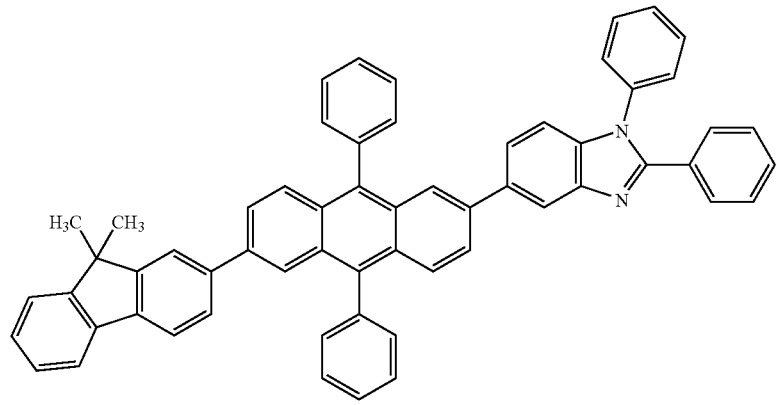
3-25
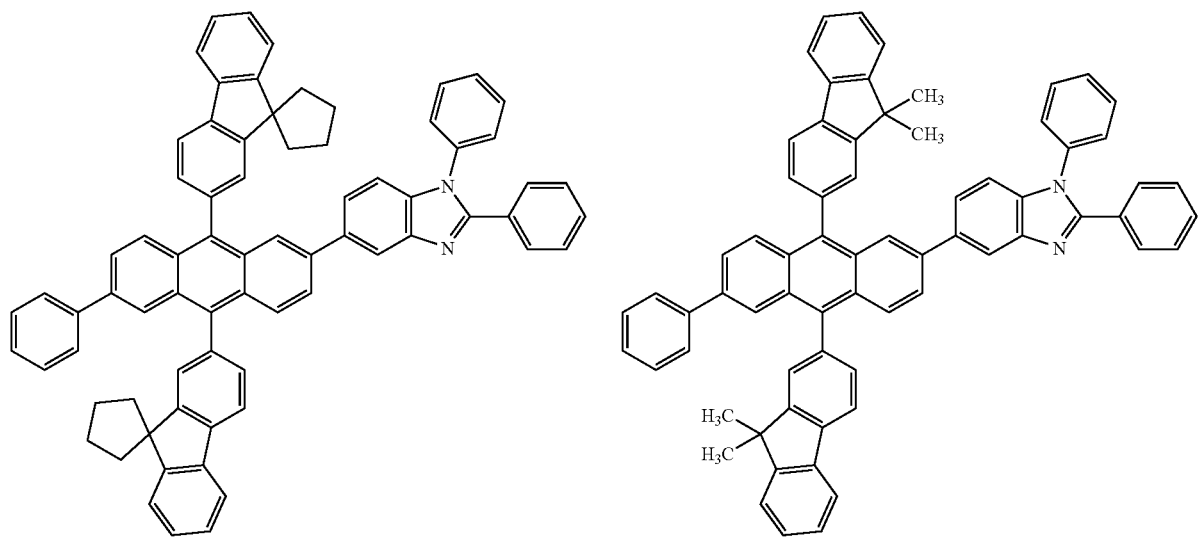
3-26    3-27
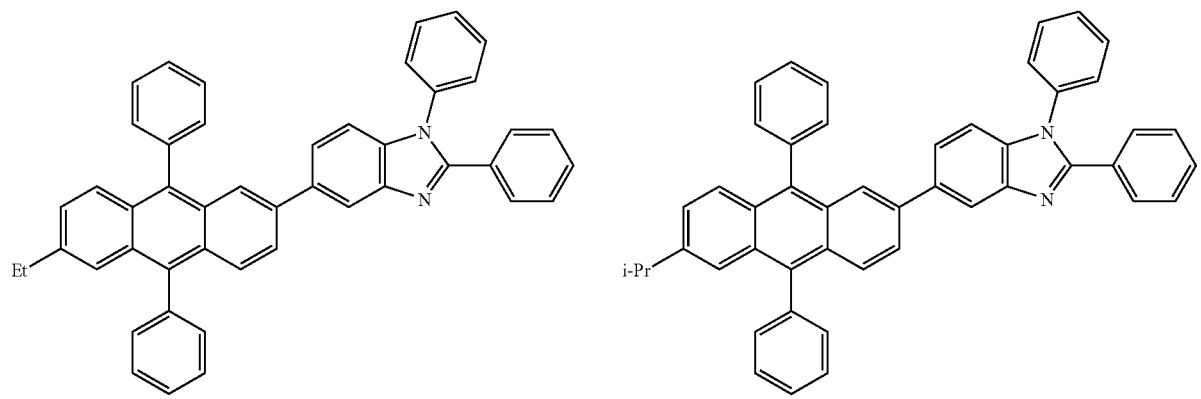
3-28    3-29

-continued
3-30
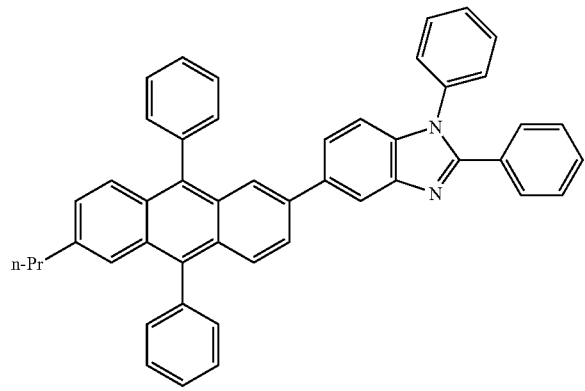
3-31
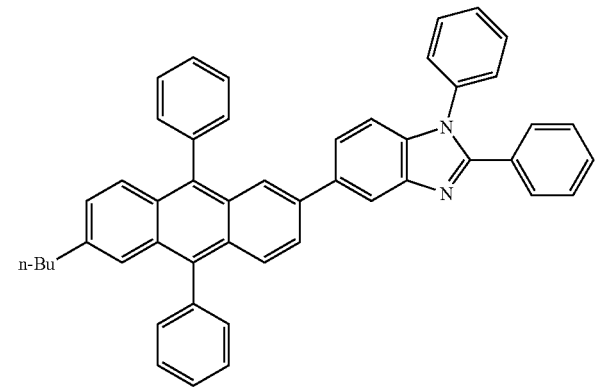
3-32
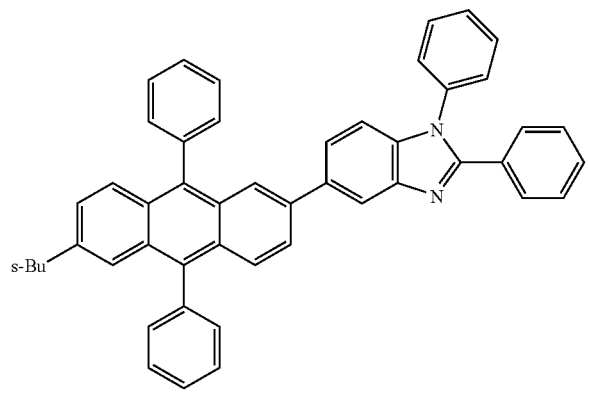
3-33
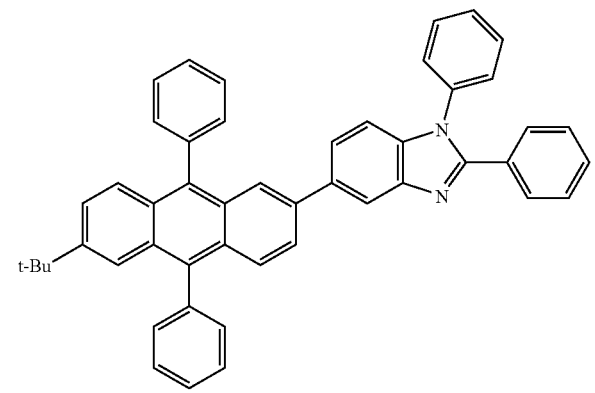
3-34
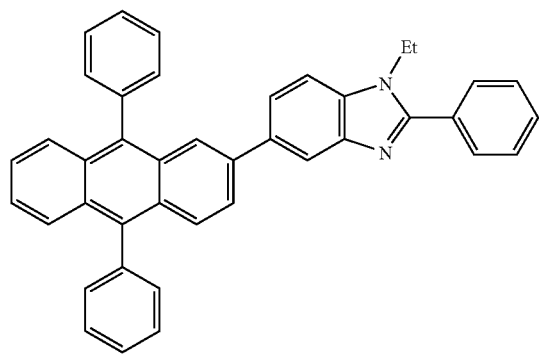
3-35
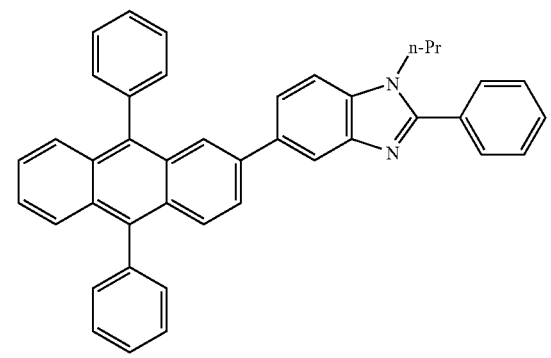
3-36
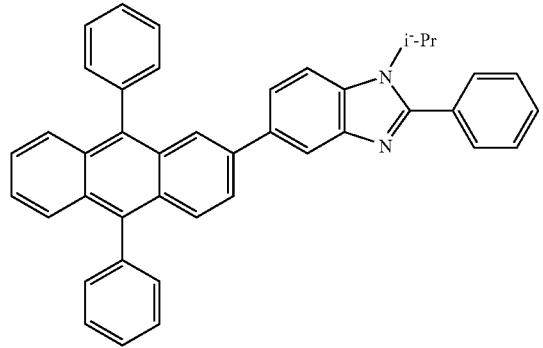
3-37
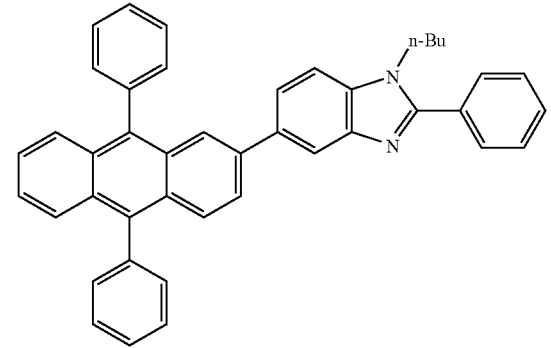

-continued
3-38
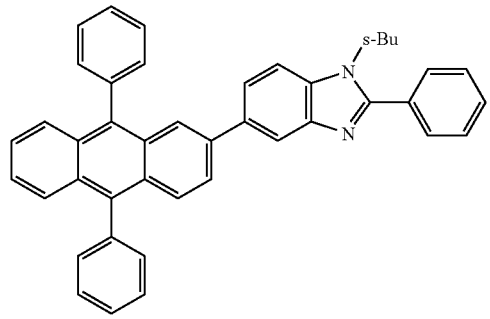
3-39
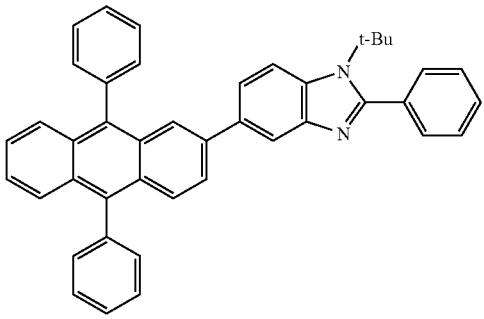
3-40
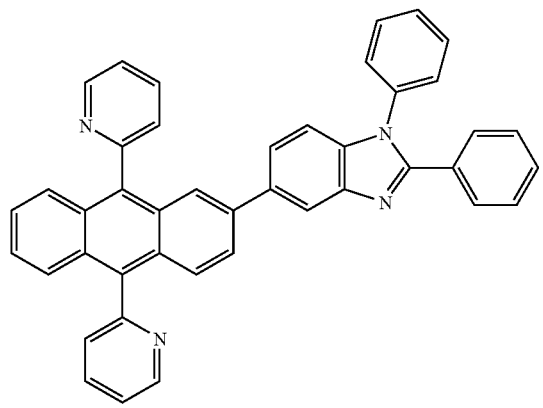
3-41
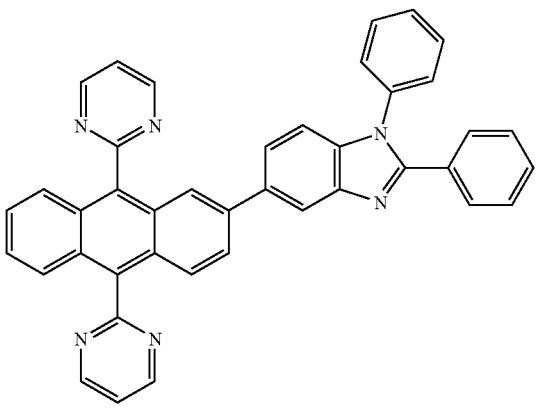
3-42
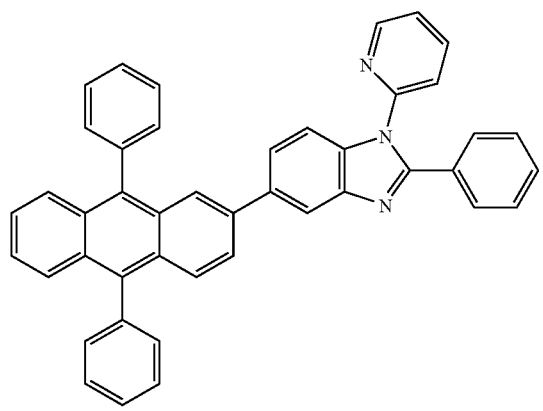
3-43
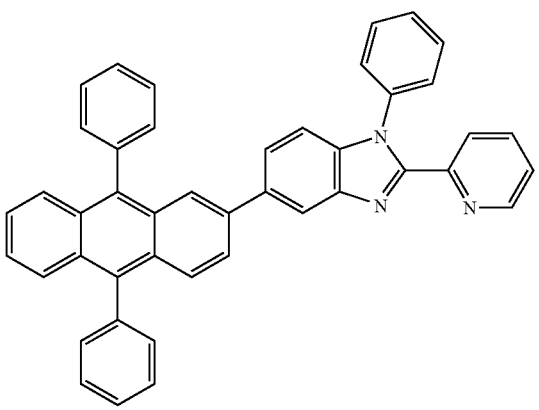
3-44
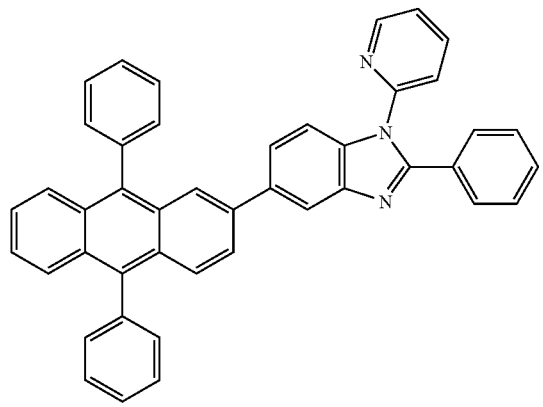
3-45
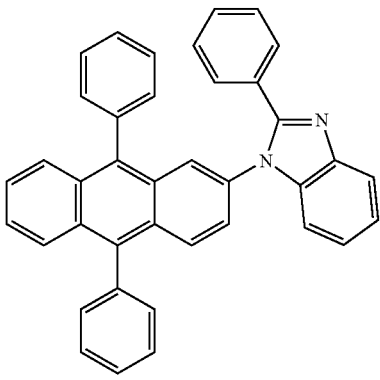

-continued
3-46
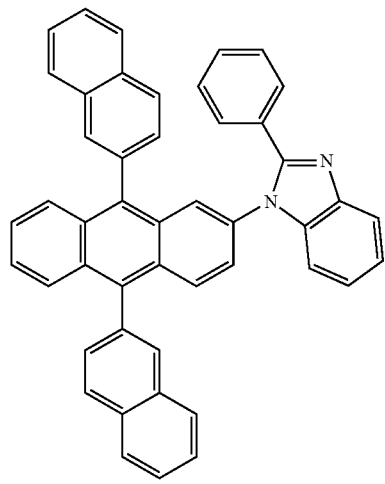
3-47
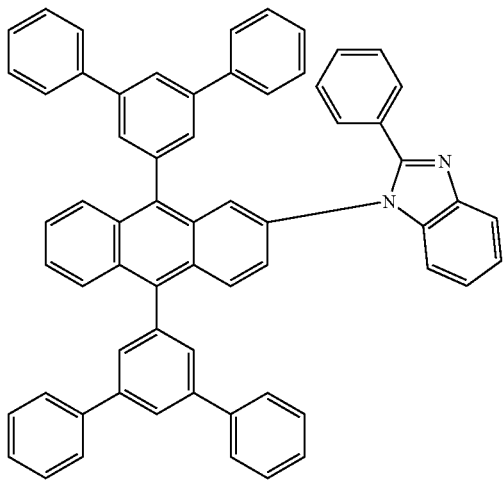
3-48
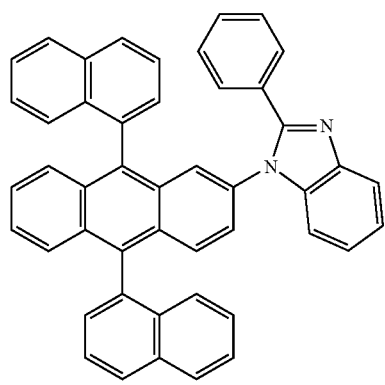
3-49
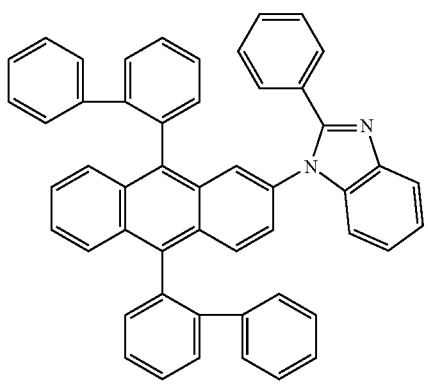
3-50
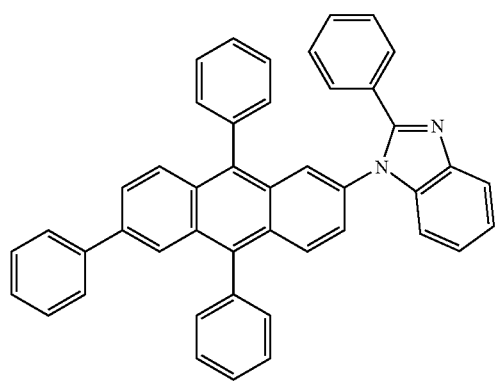
3-51
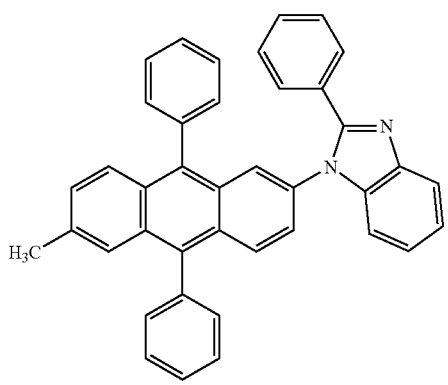
3-52
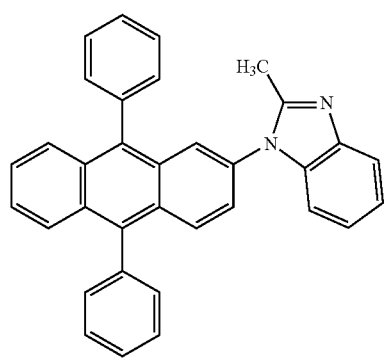
3-53
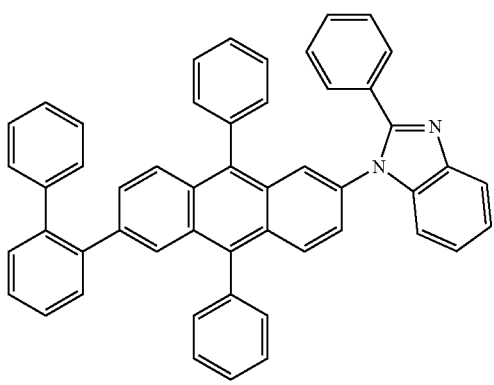

-continued
3-54
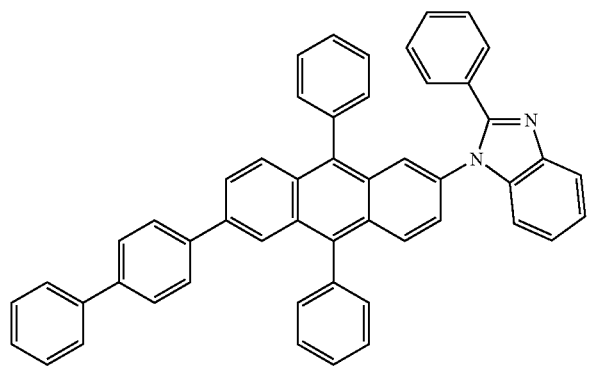
3-55
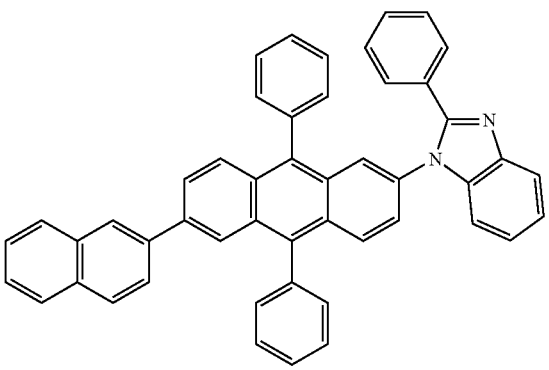
3-56
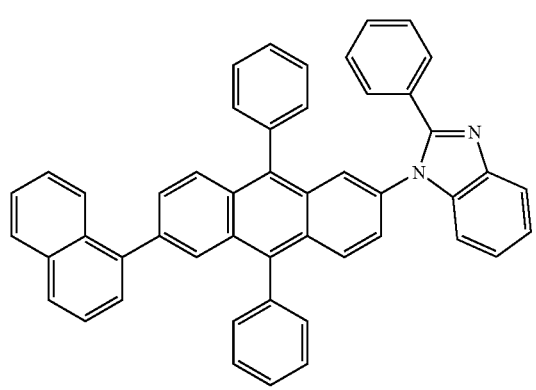
3-57
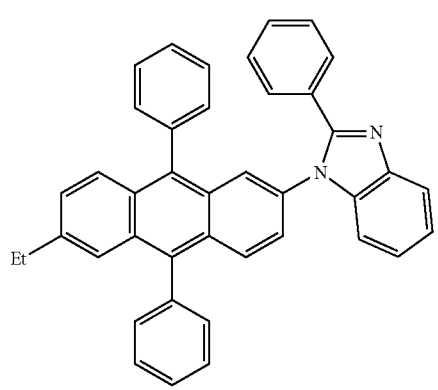
3-58
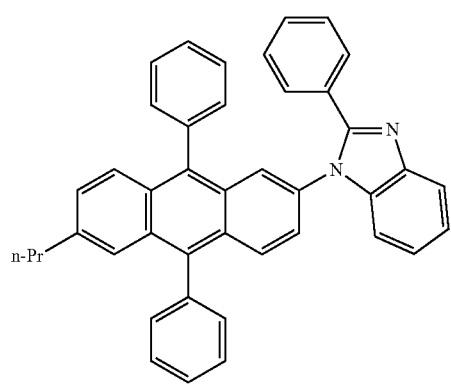
3-59
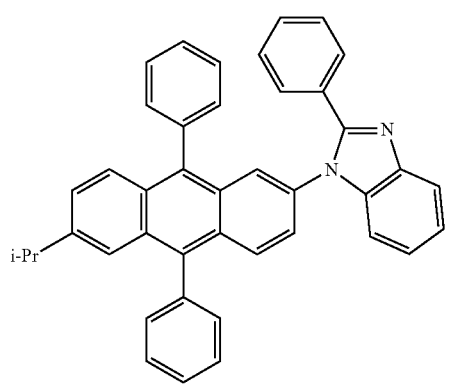
3-60
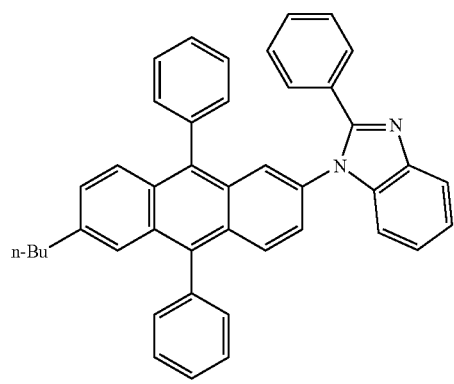
3-61
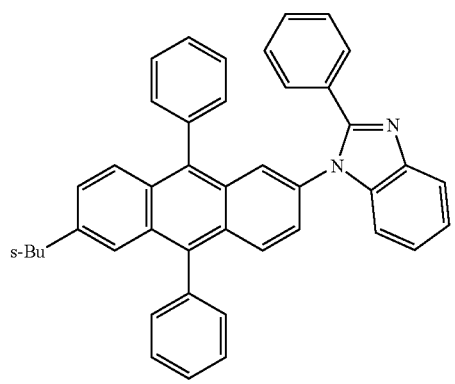

-continued
3-62
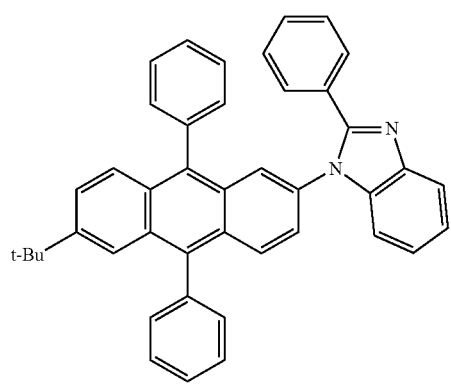
3-63
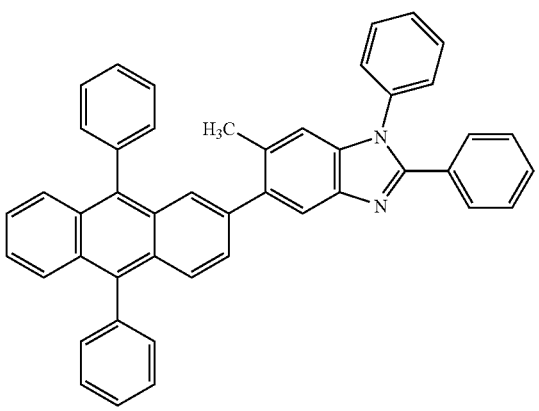
3-64
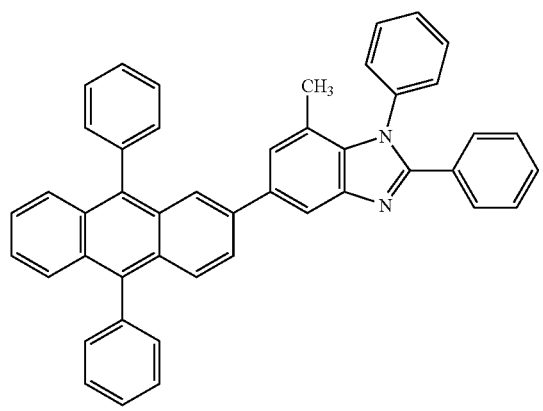
3-65
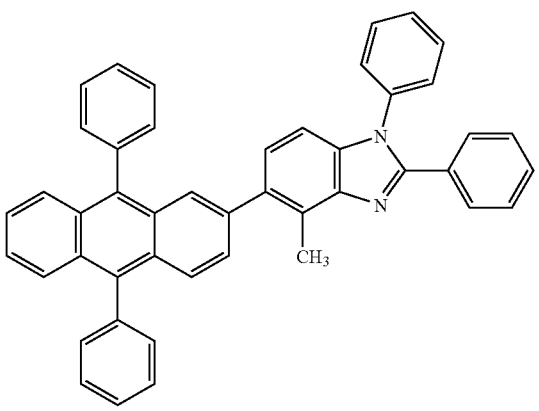
3-66
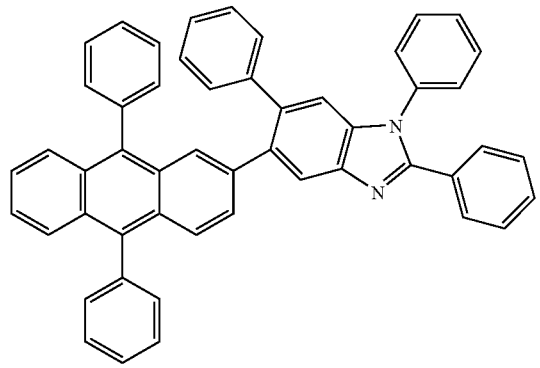
3-67
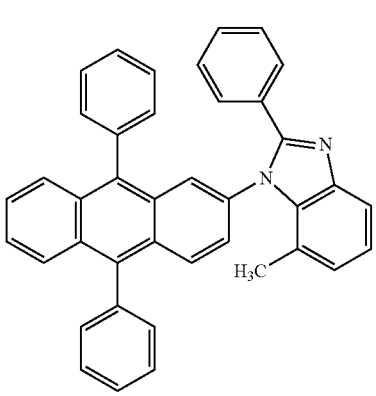
3-68
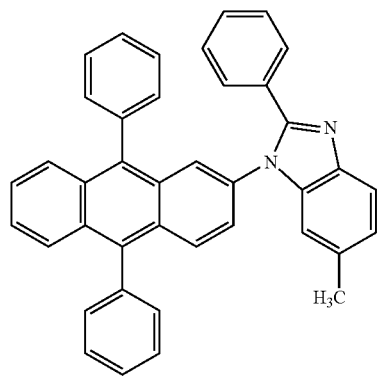
3-69
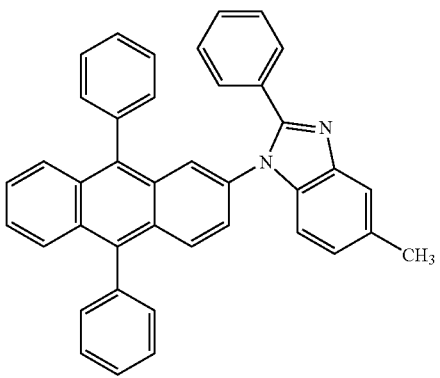

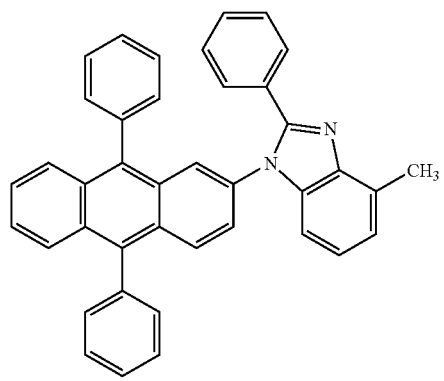
3-70
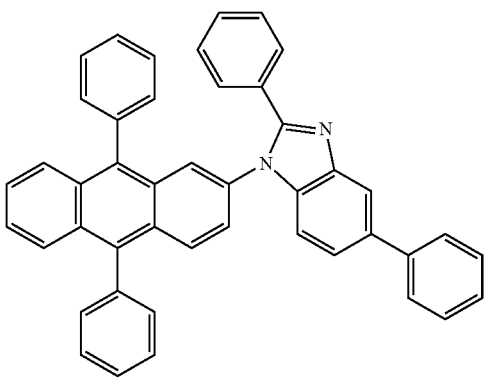
3-71
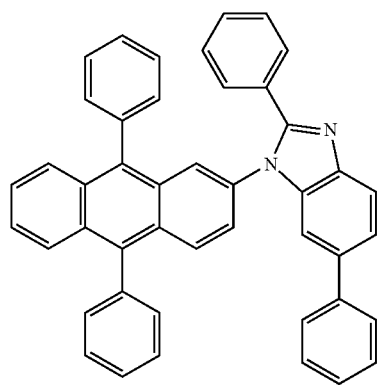
3-72
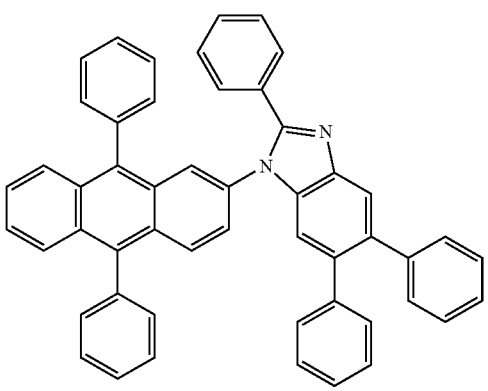
3-73
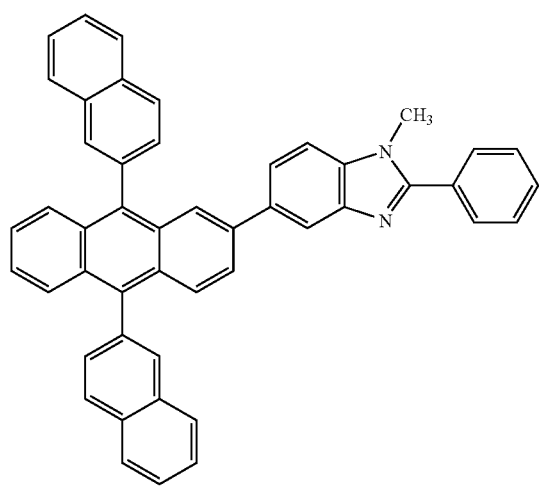
3-74
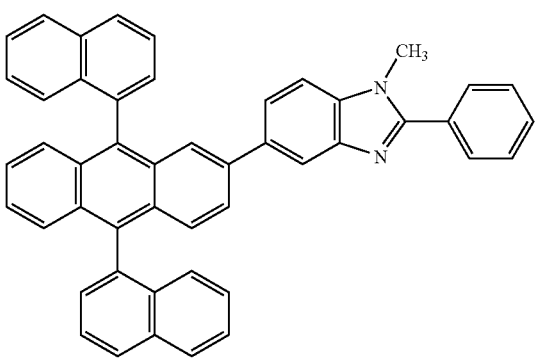
3-75

-continued
3-76
3-77
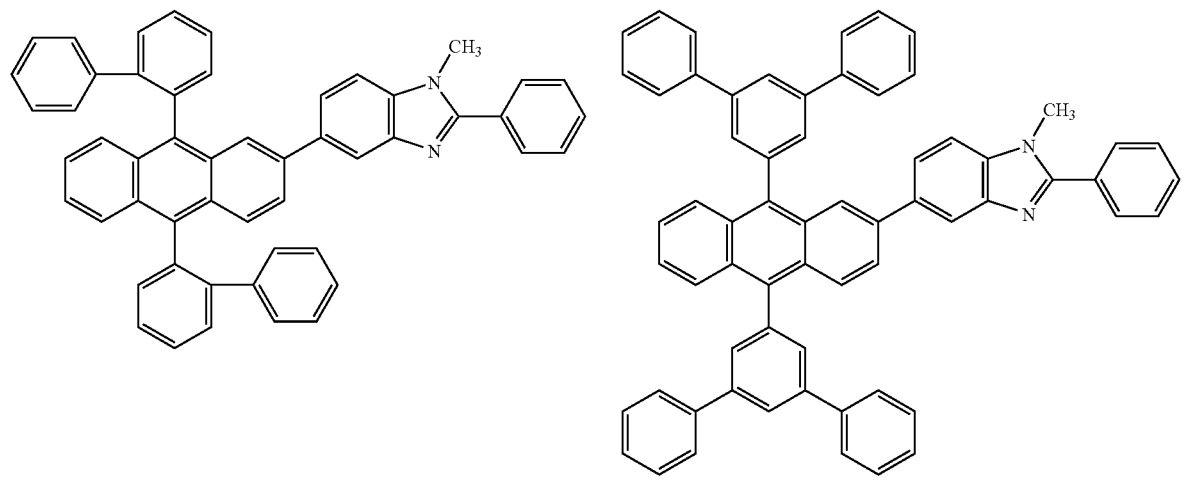
4-1
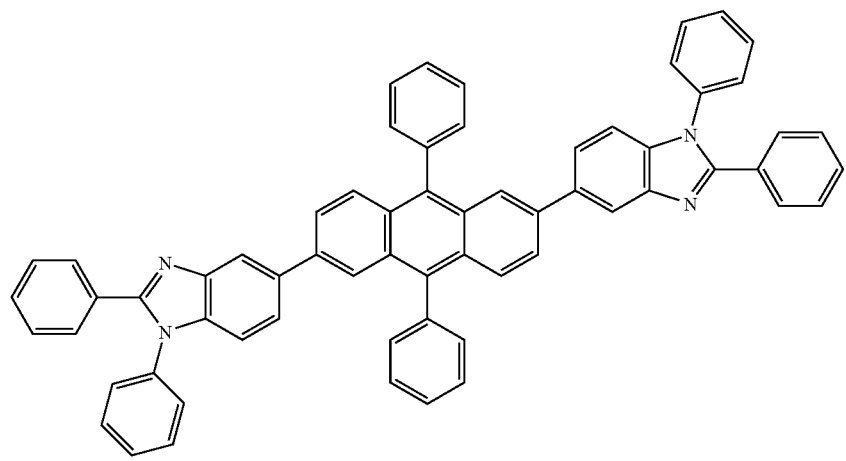
4-2
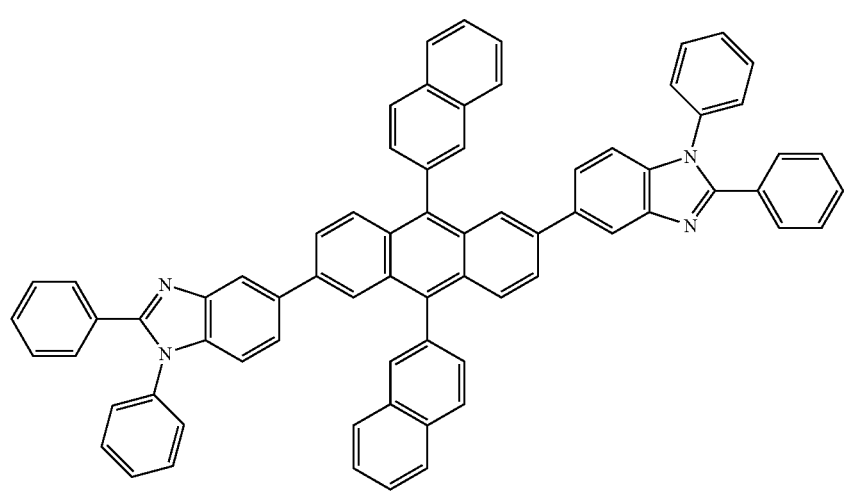

-continued
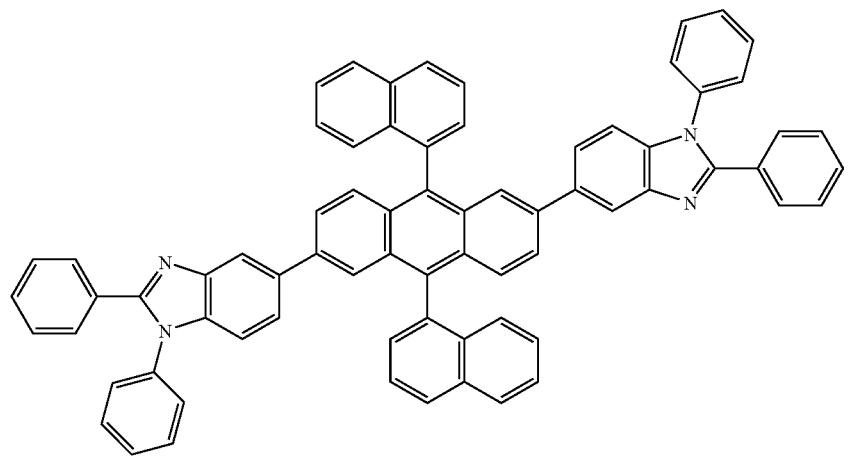
4-3
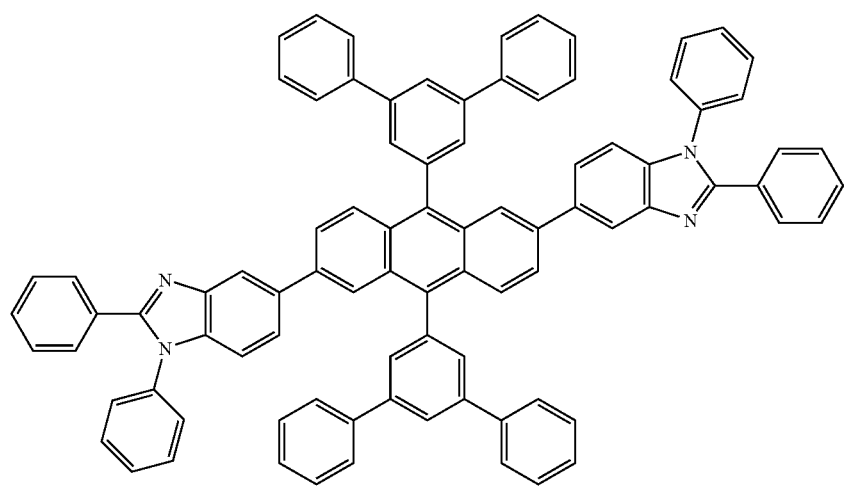
4-4
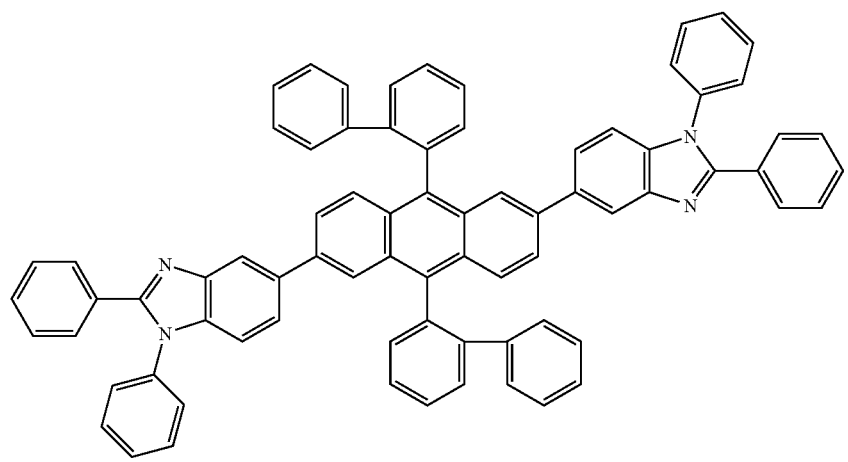
4-5

-continued
4-6
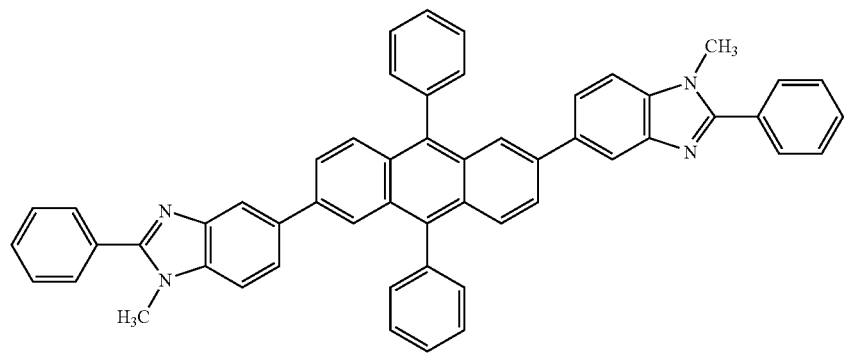
4-7
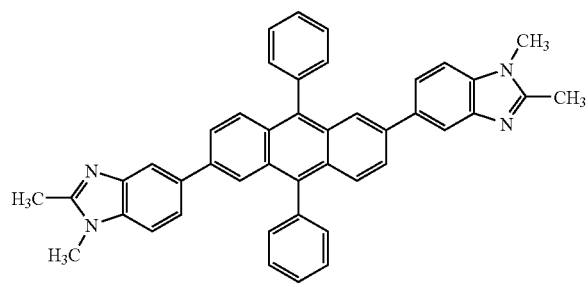
4-8
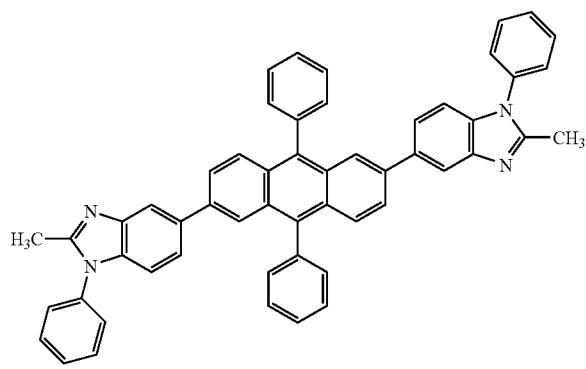
4-9
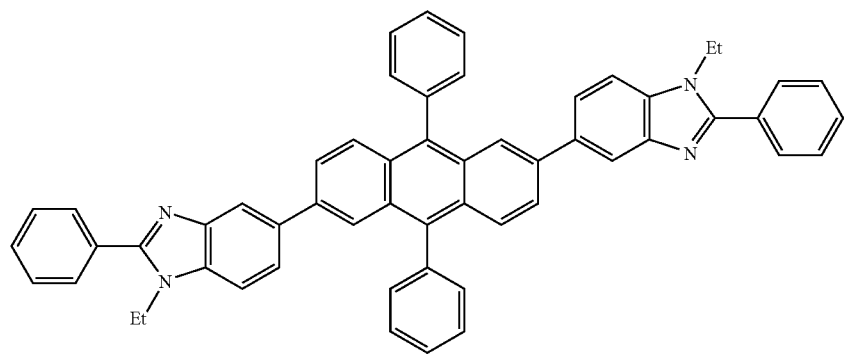
4-10
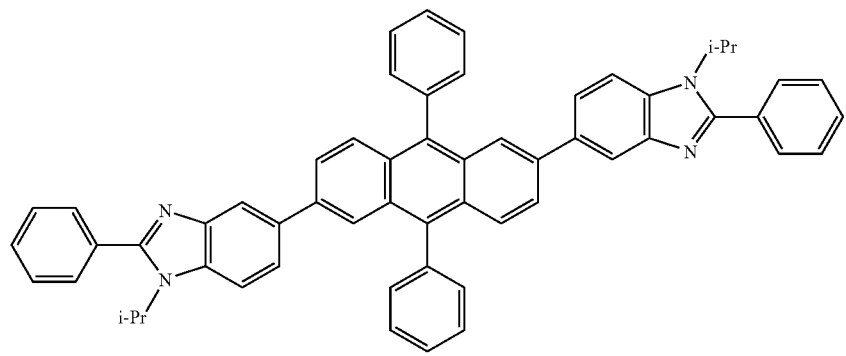

-continued
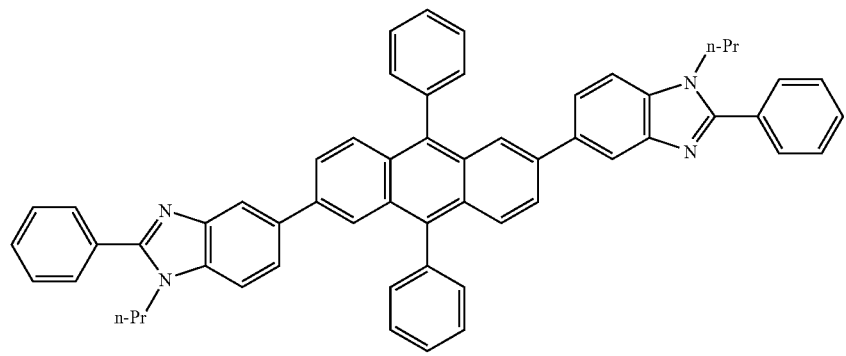
4-11
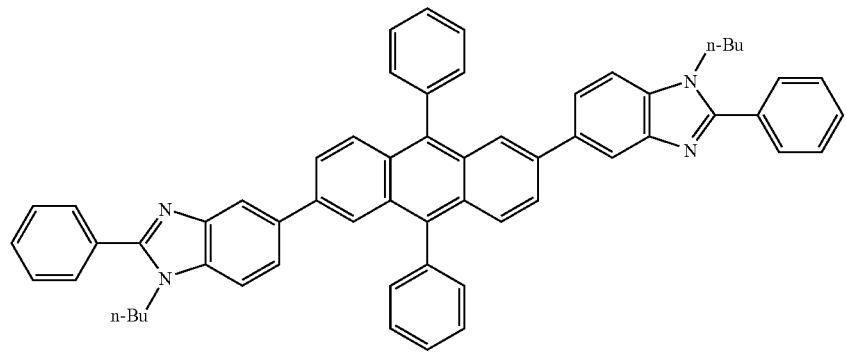
4-12
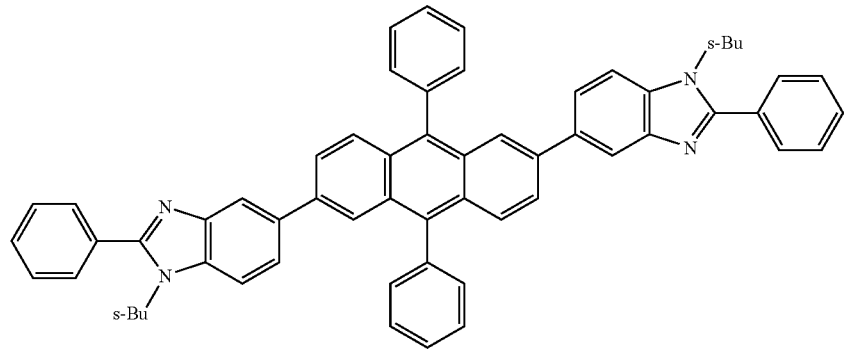
4-13
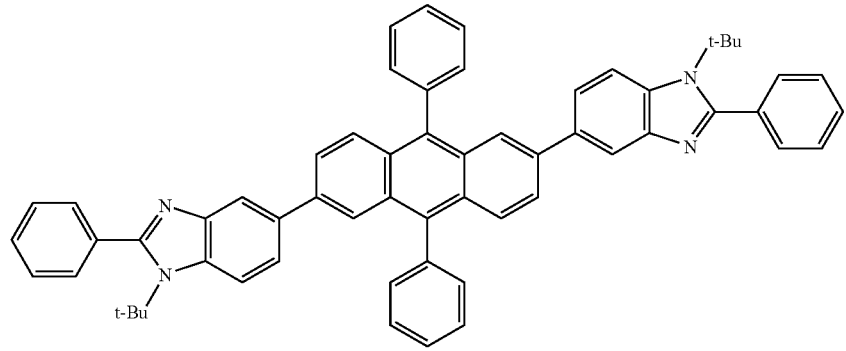
4-14

-continued
4-15
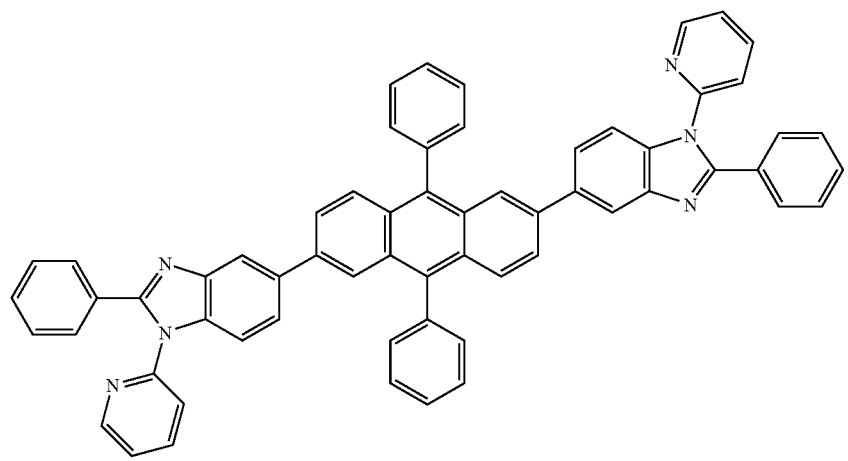
4-16
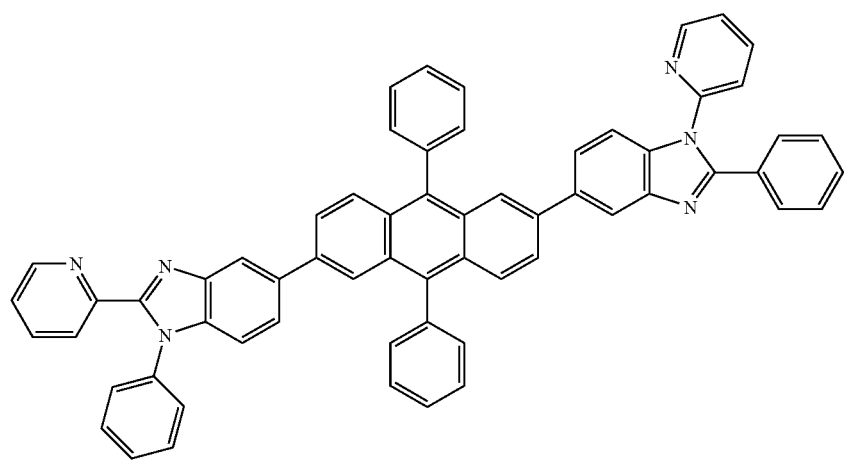
4-17
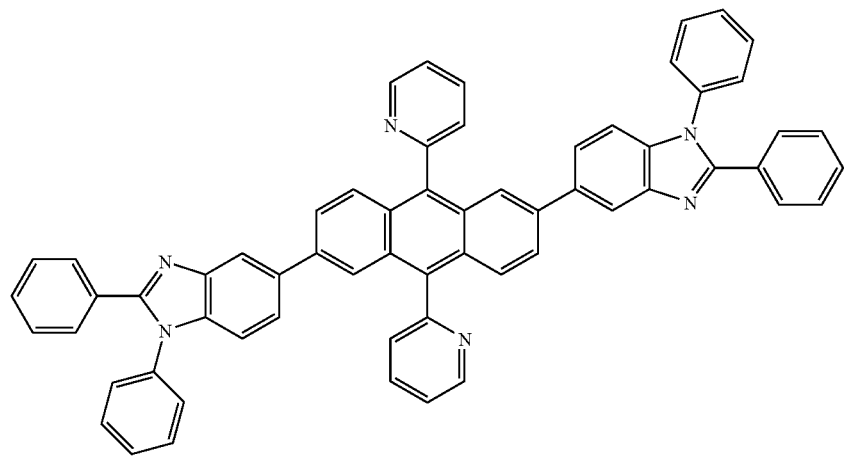

-continued
4-18
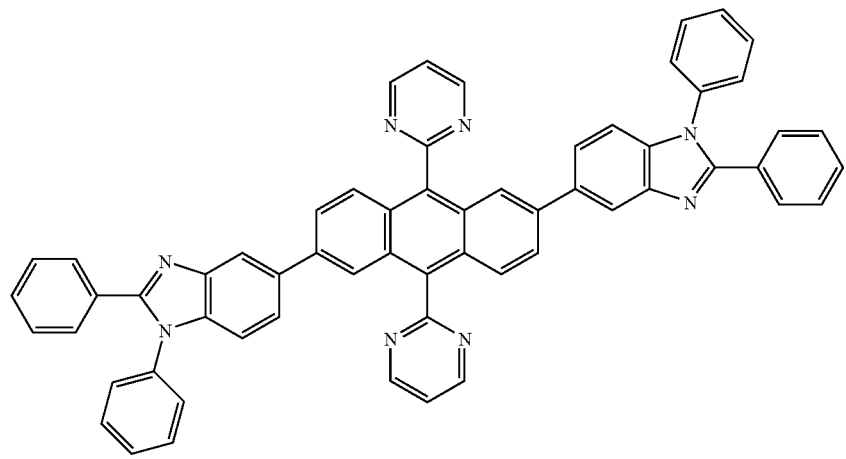
4-19
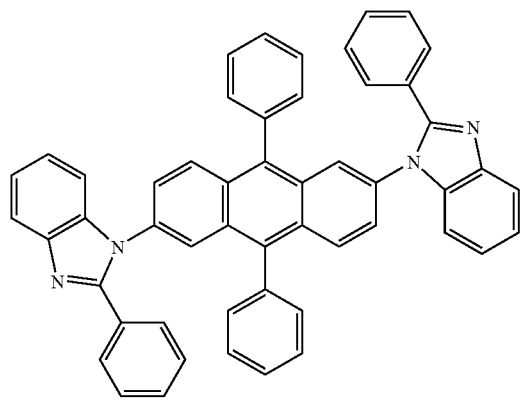
4-20
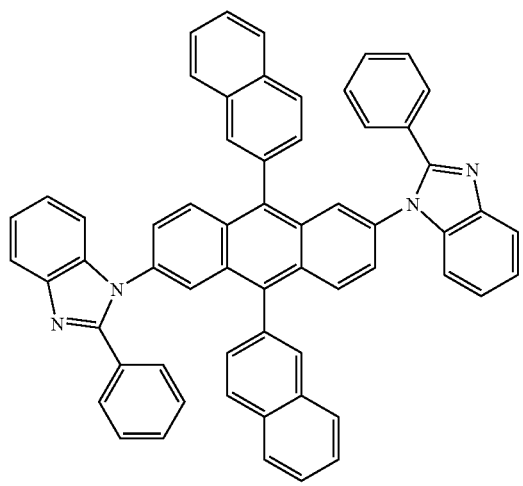
4-21
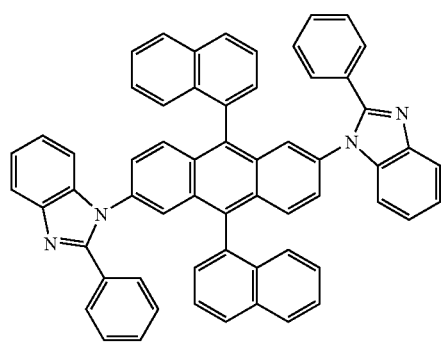
4-22
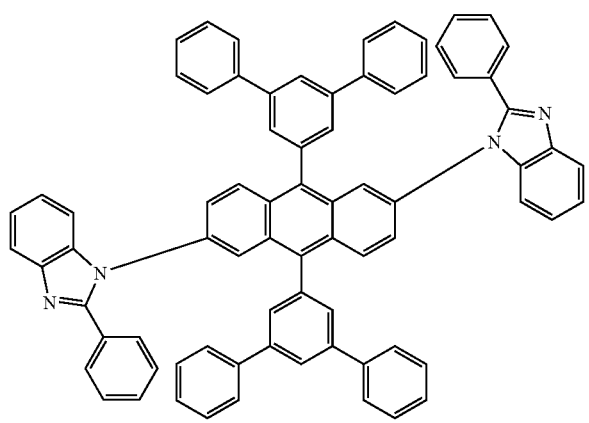

-continued
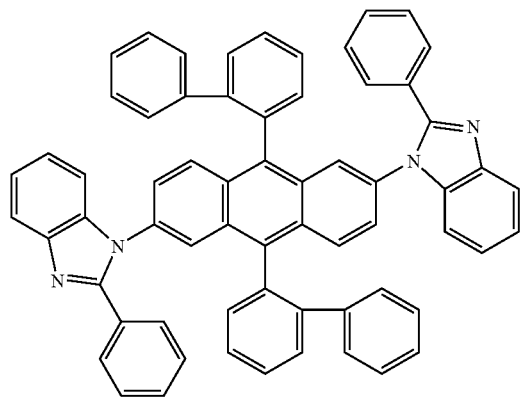
4-23
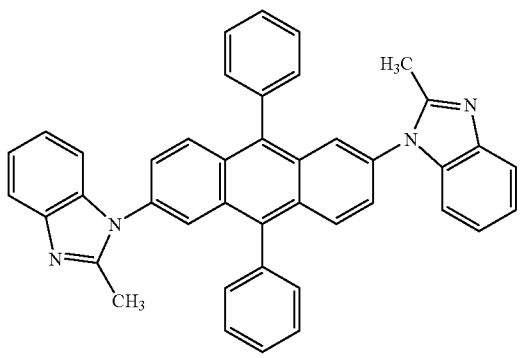
4-24
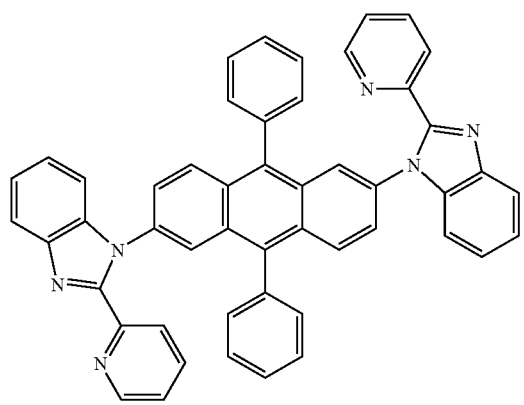
4-25
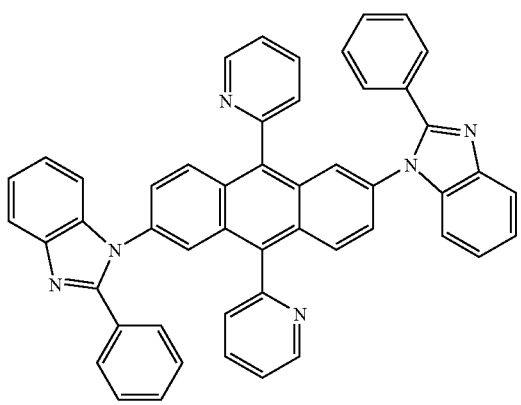
4-26
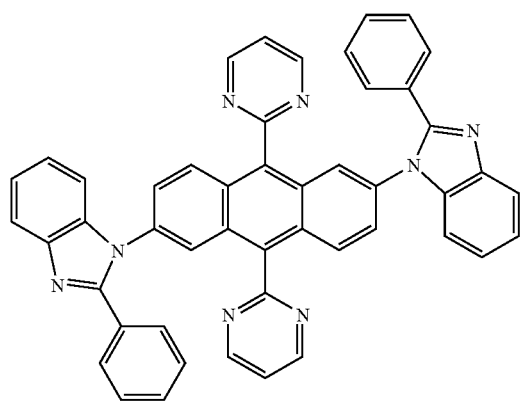
4-27

4-28
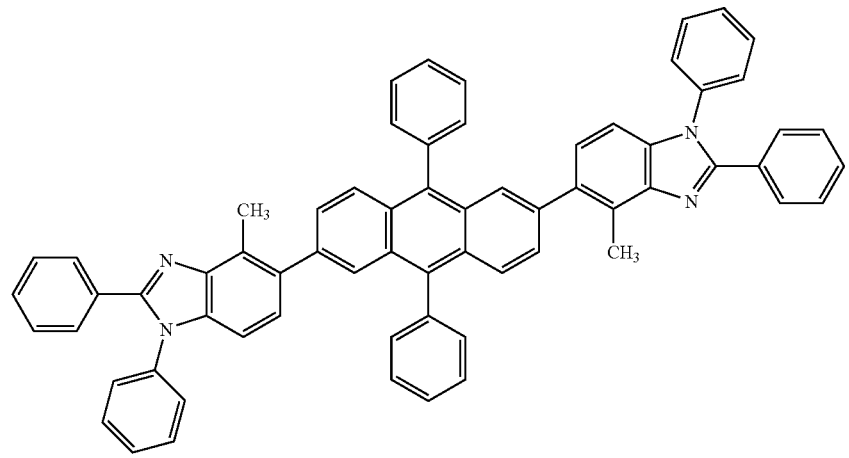
4-29
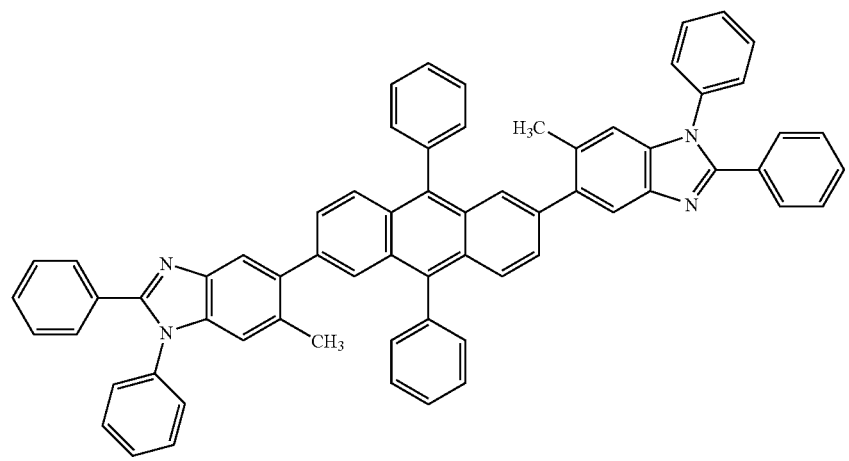
4-30
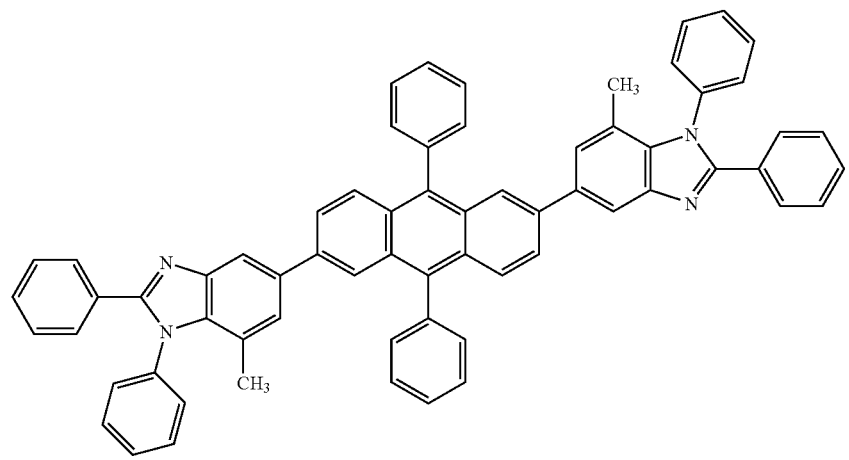

-continued
4-31
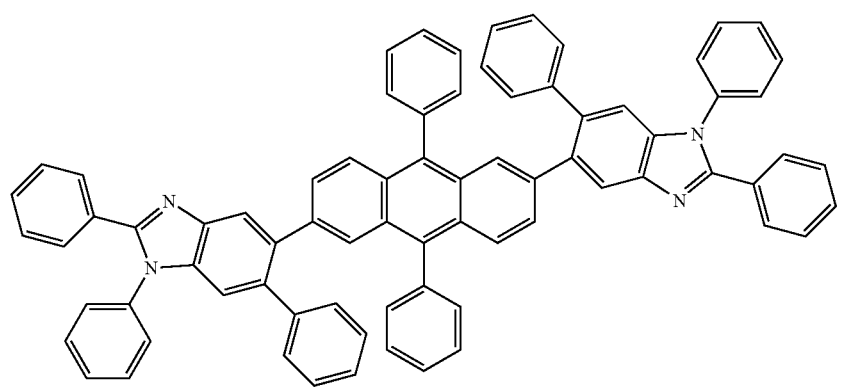
4-32
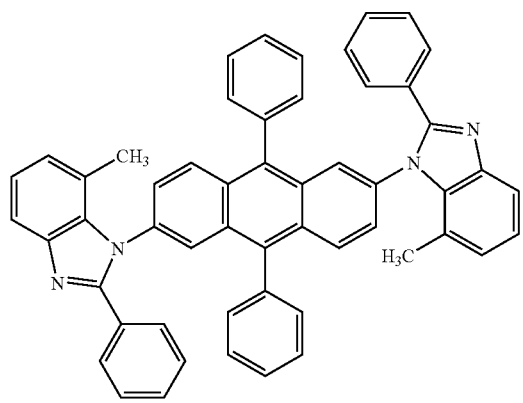
4-33
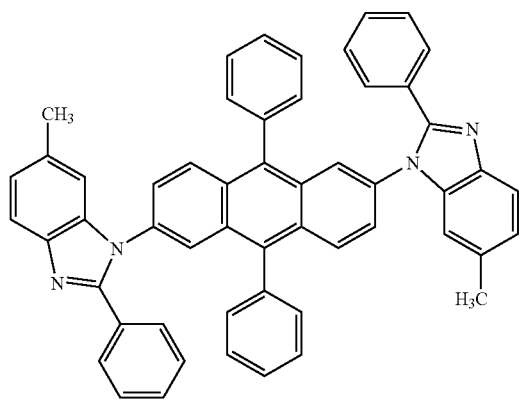
4-34
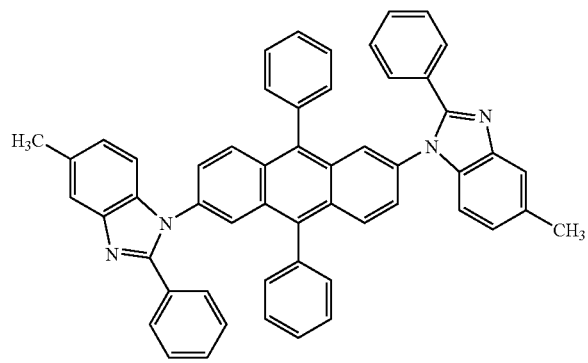
4-35
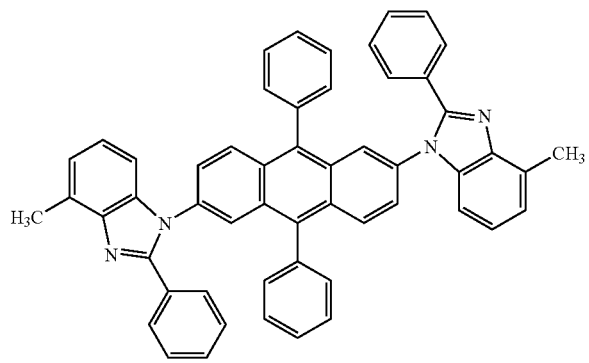
4-36
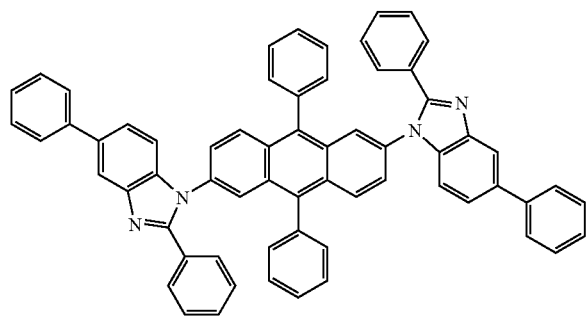
4-37
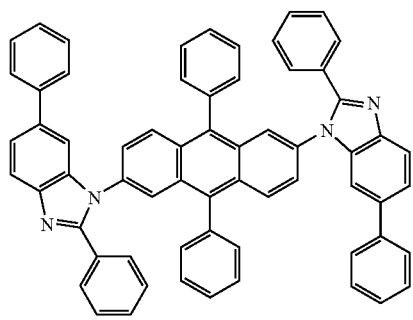

4-38
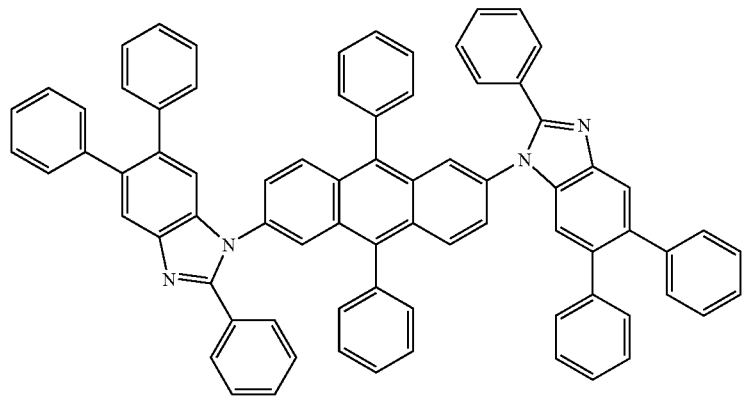
5-1
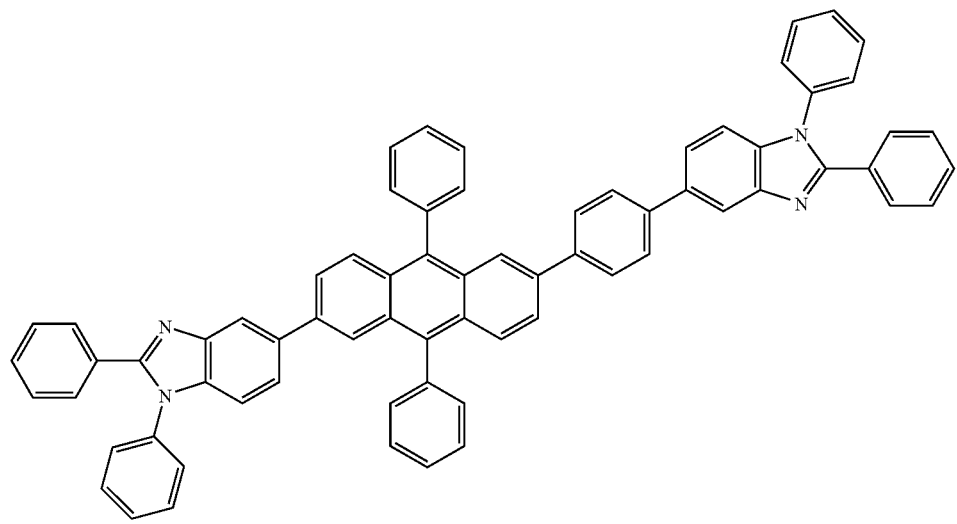
5-2
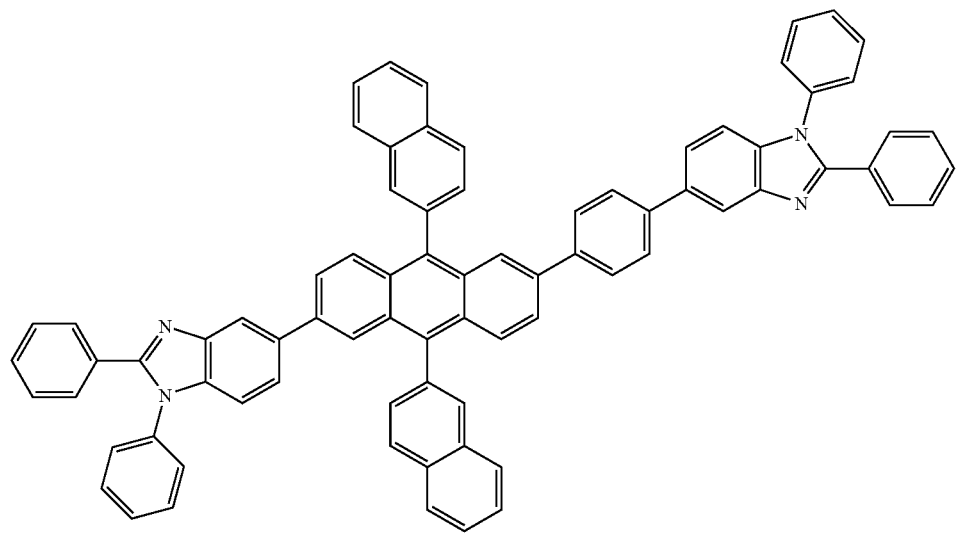

-continued
5-3
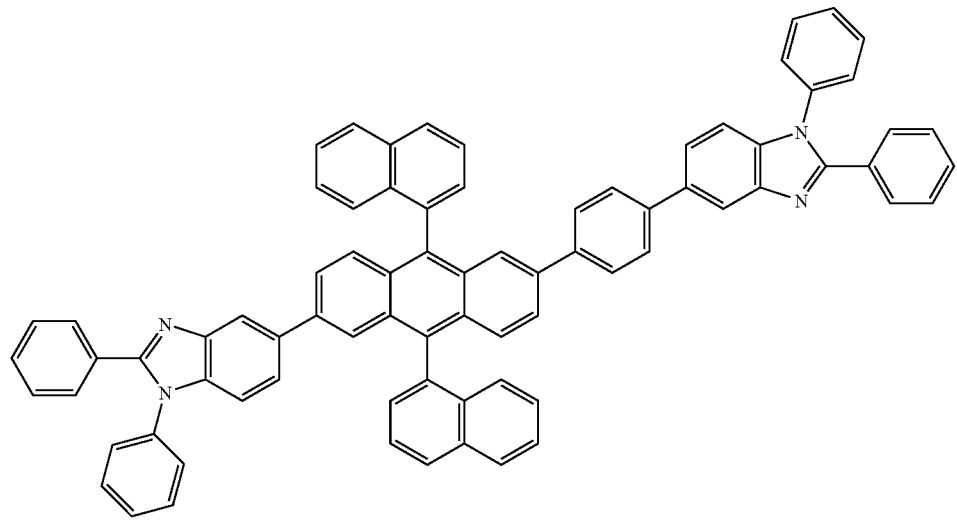
5-4
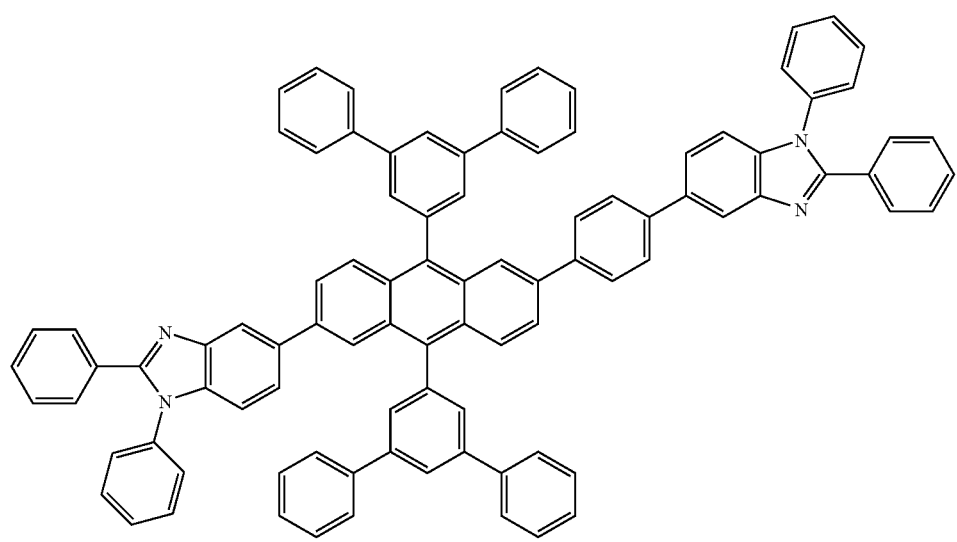
5-5
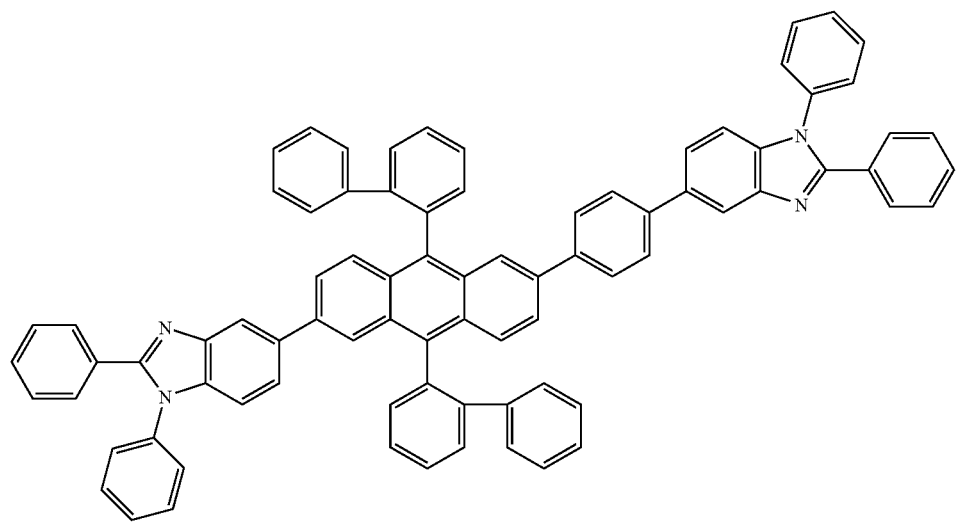

-continued
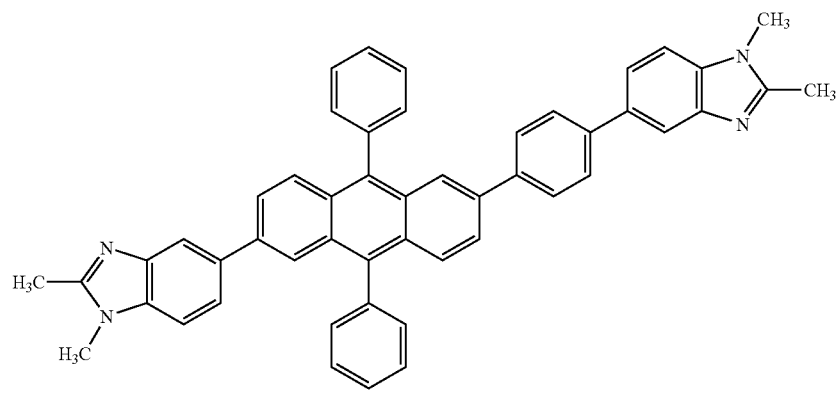
5-6
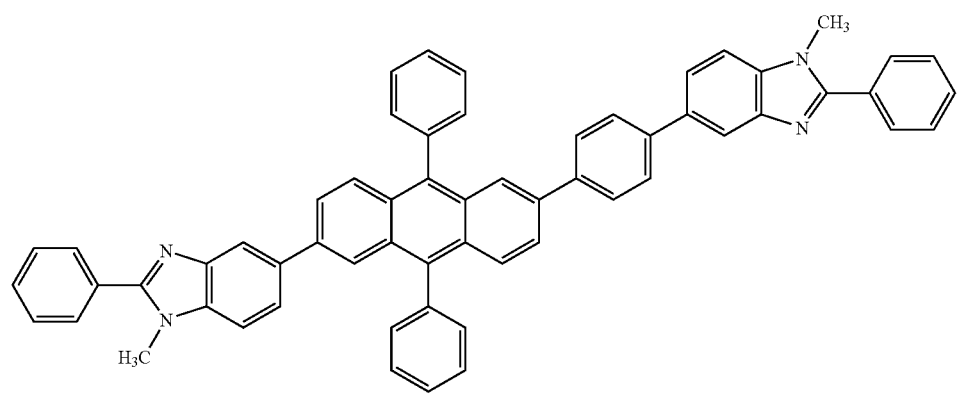
5-7
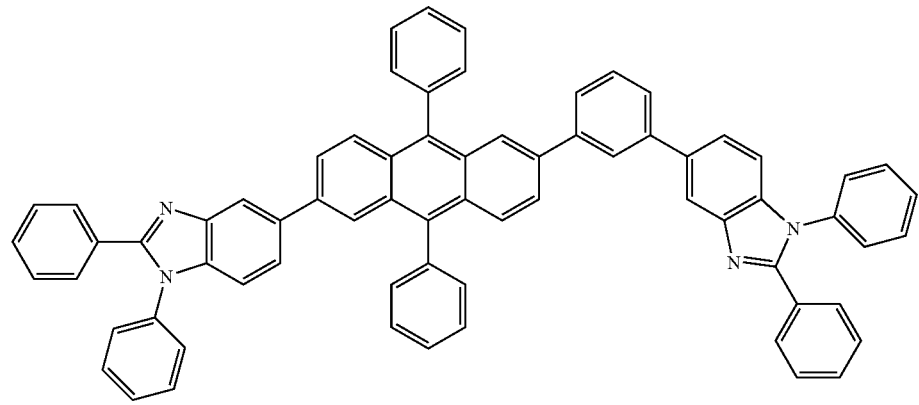
5-8
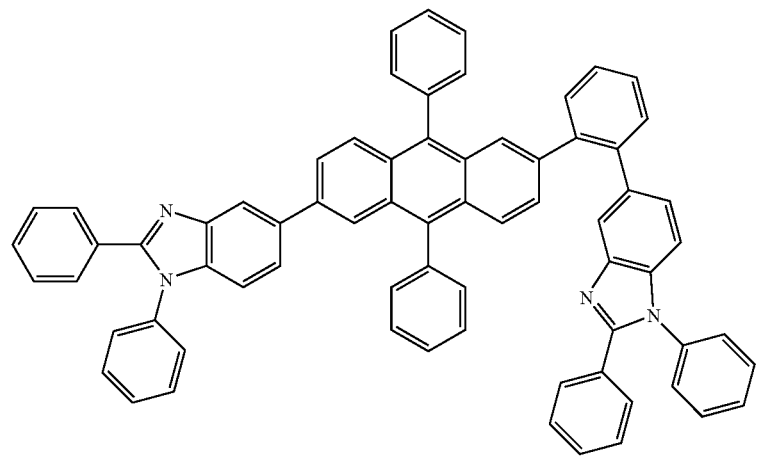
5-9

-continued
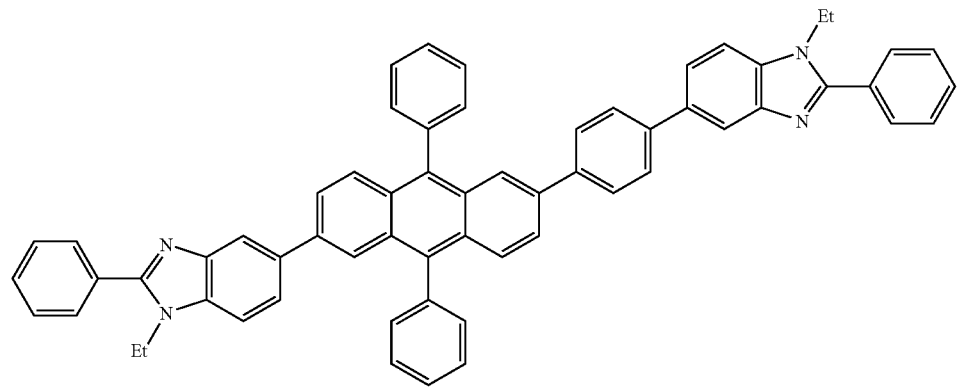
5-10
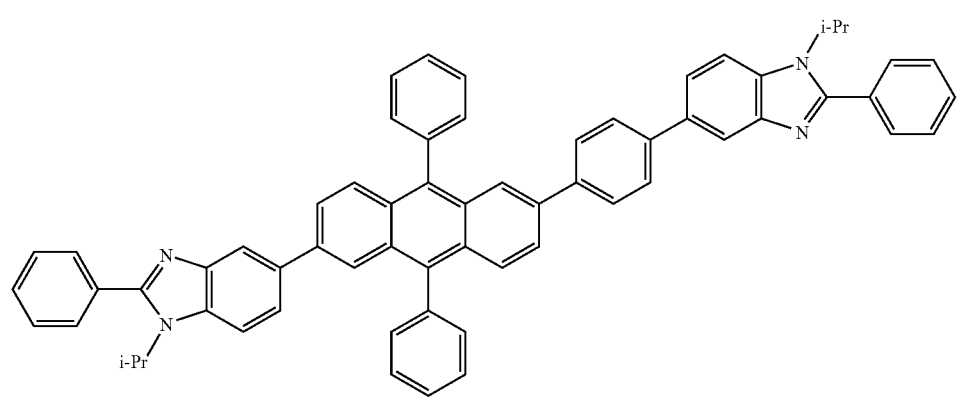
5-11
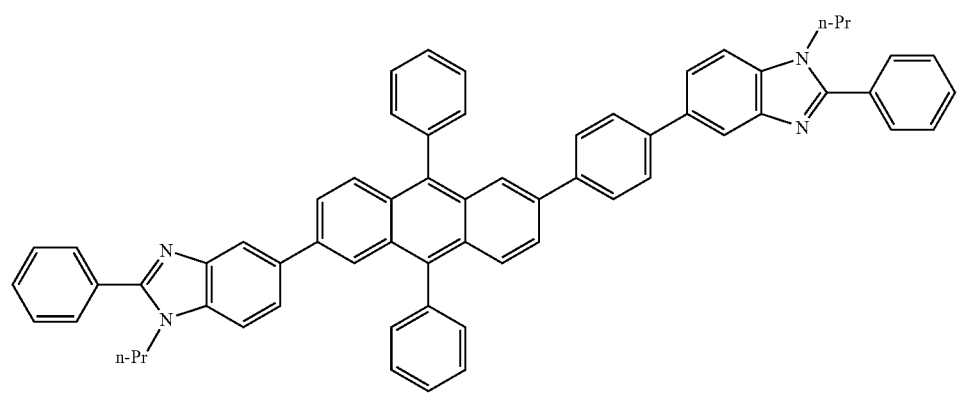
5-12
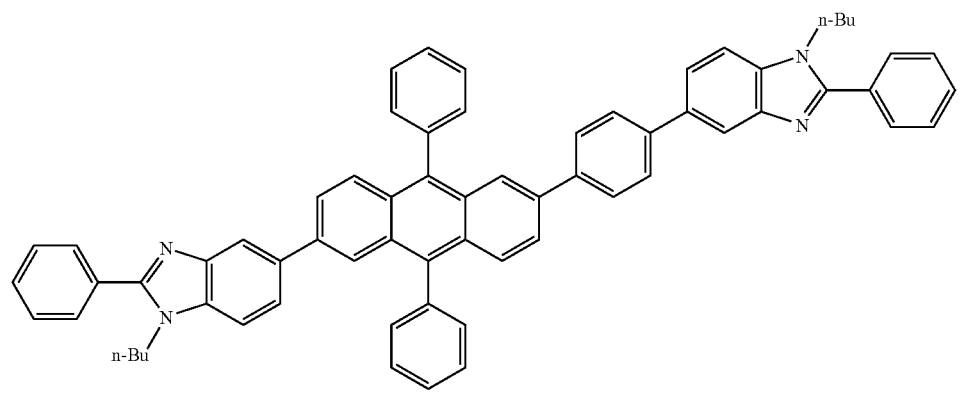
5-13

5-14
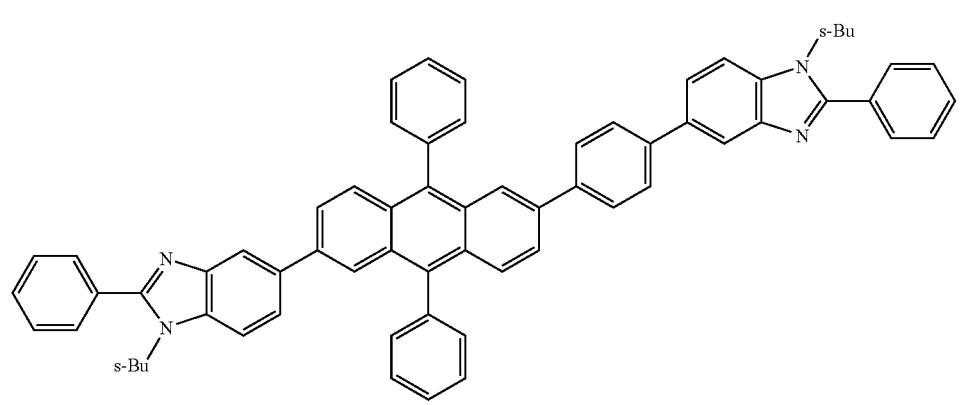
5-15
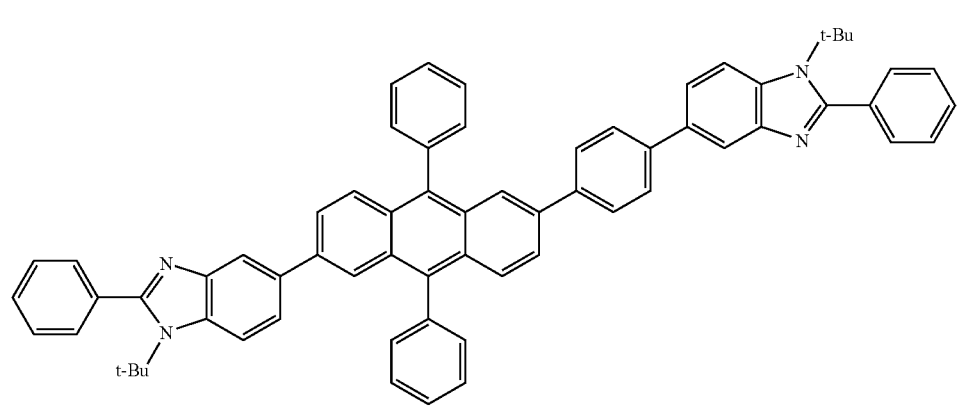
5-16
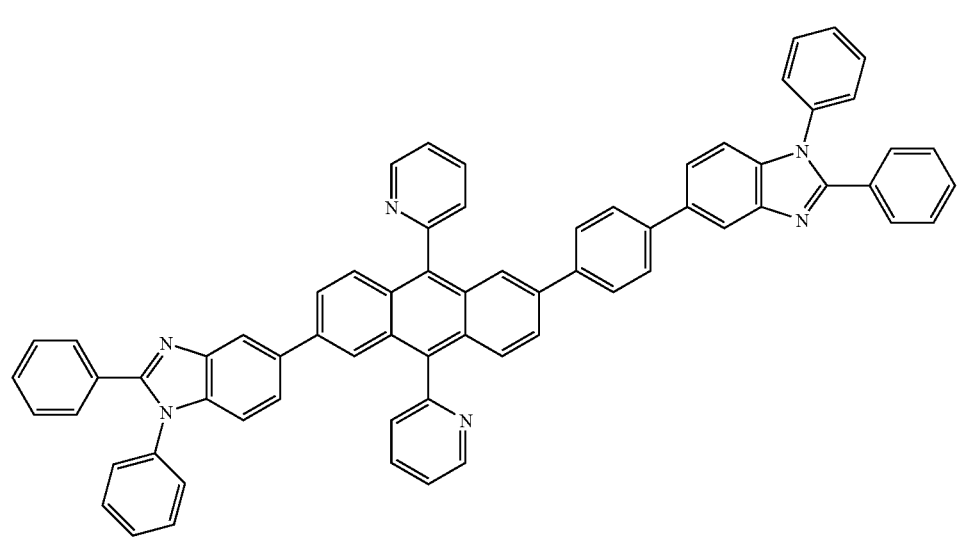

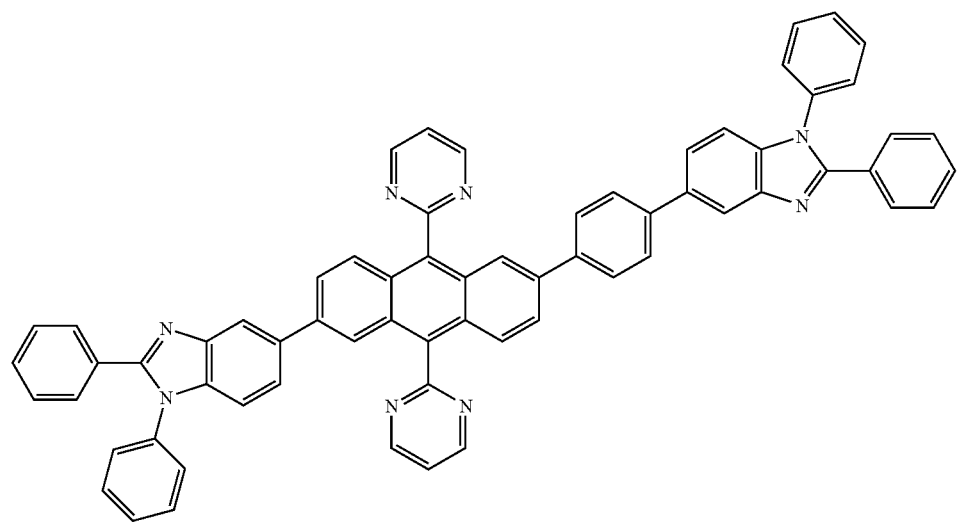
5-17
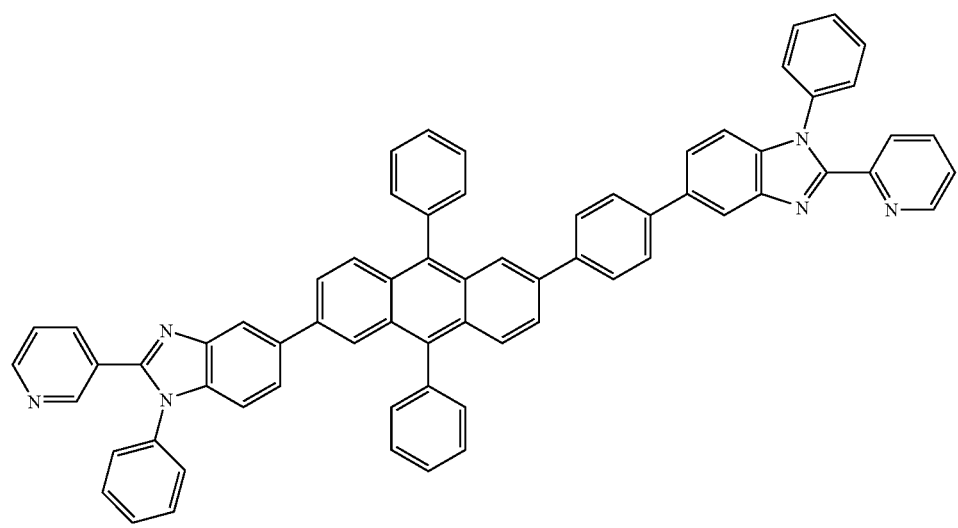
5-18
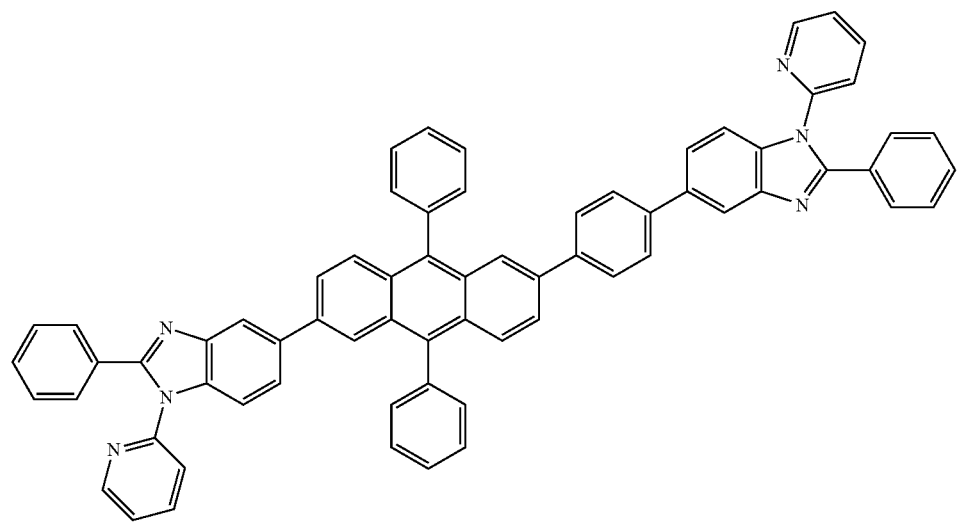
5-19

-continued
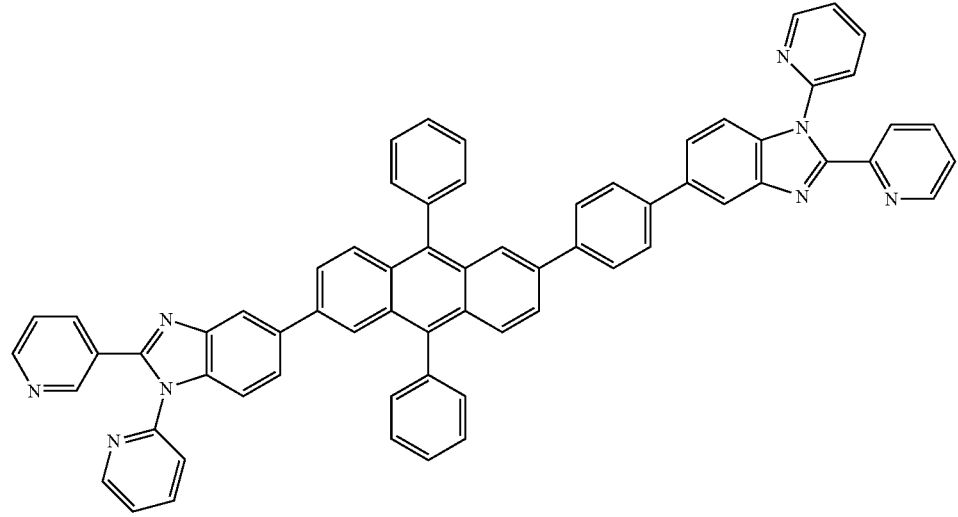
5-20
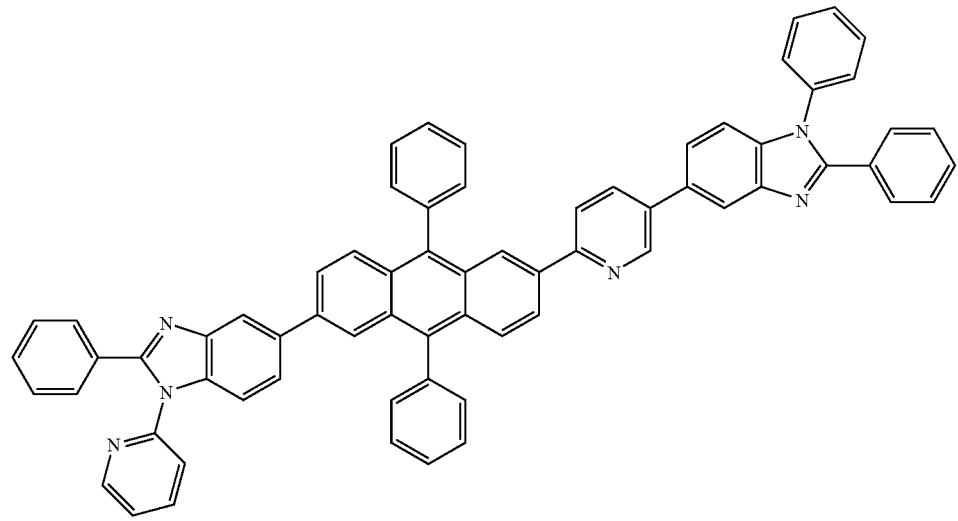
5-21
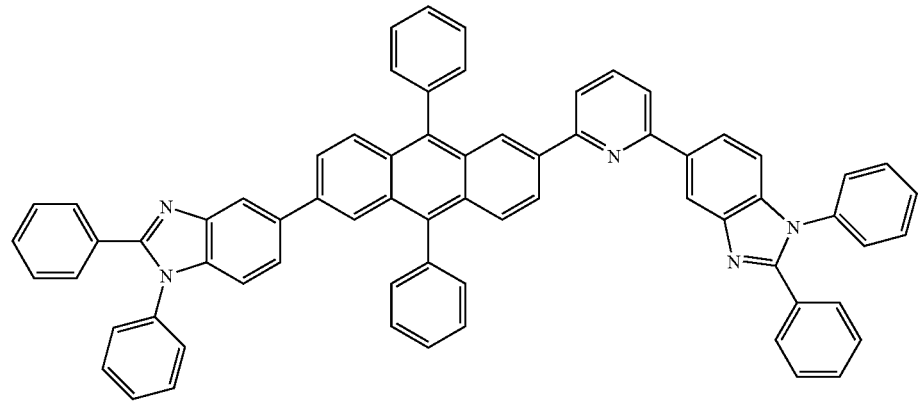
5-22

-continued
5-23
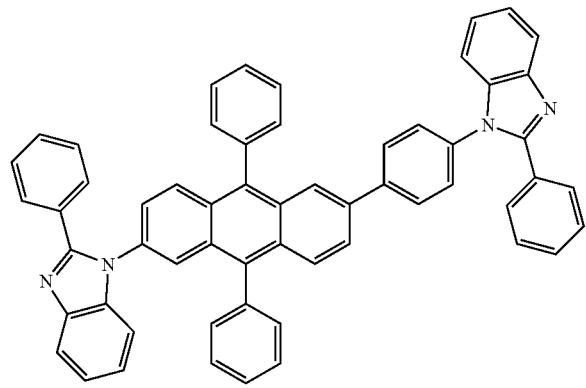
5-24
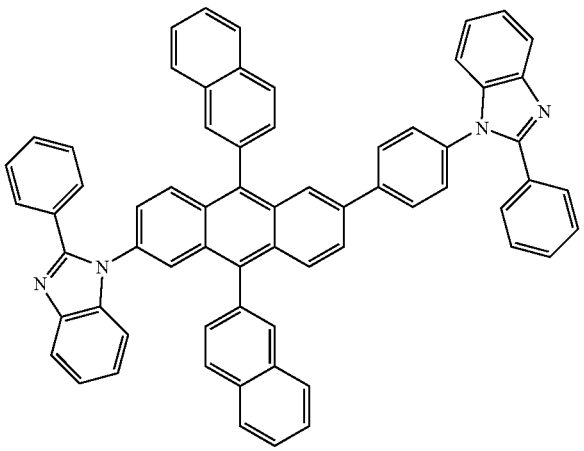
5-25
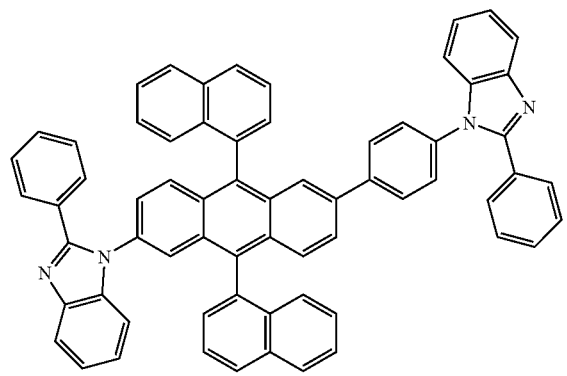
5-26
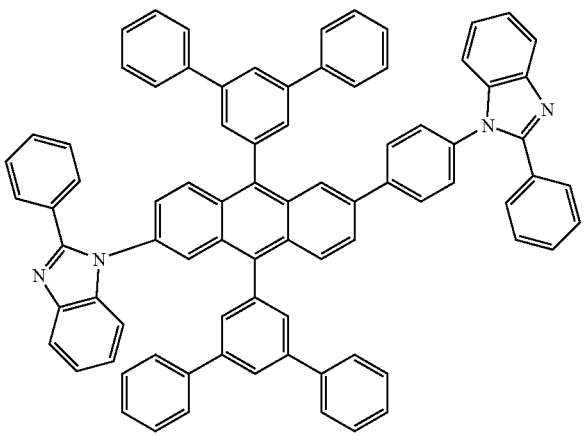
5-27
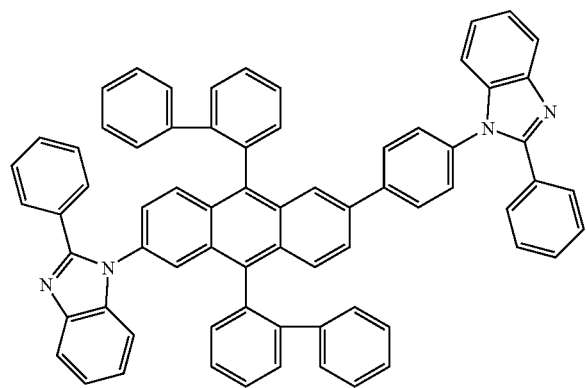
5-28
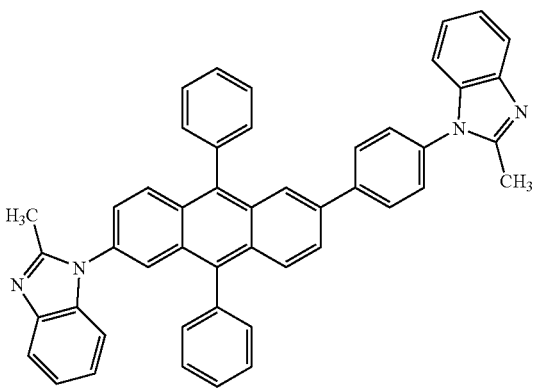

-continued
5-29
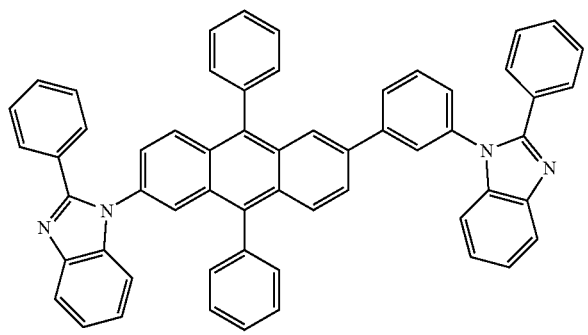
5-30
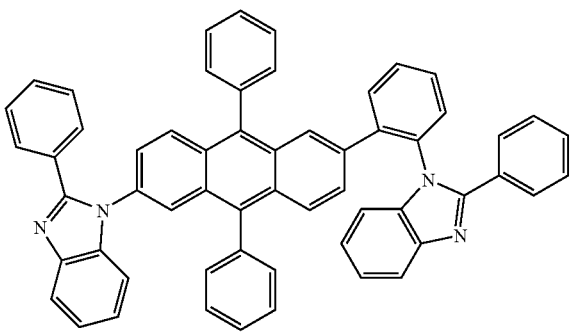
5-31
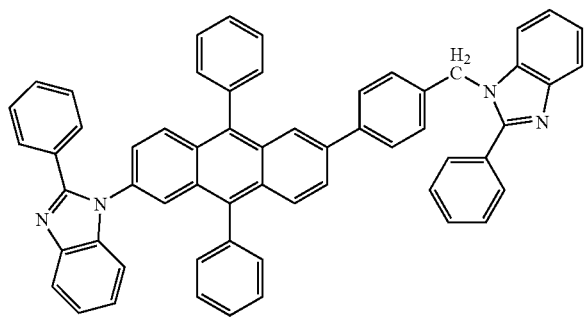
5-32
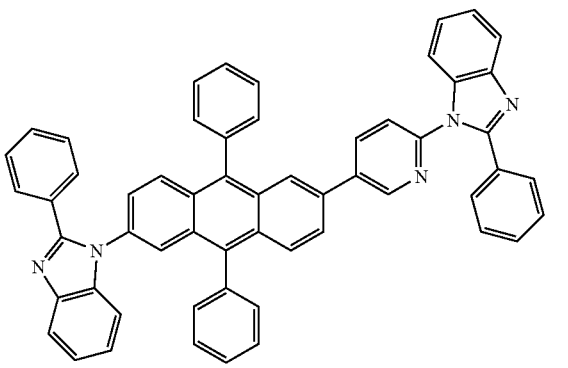
5-33
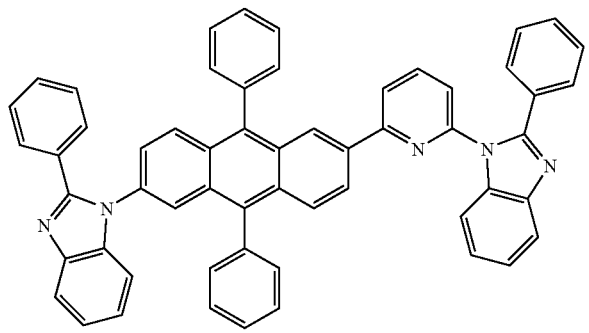
5-34
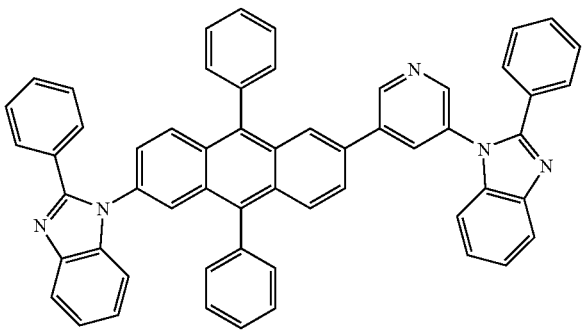
5-35
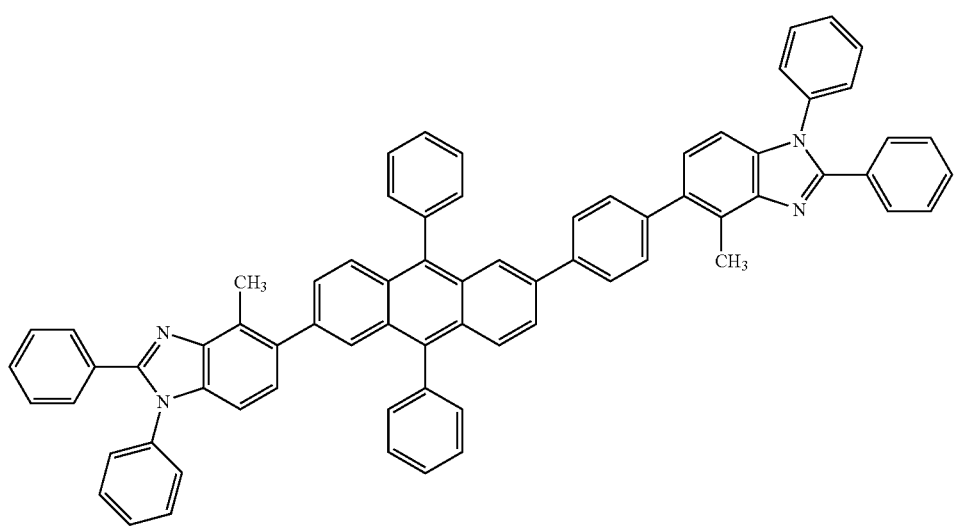

5-36
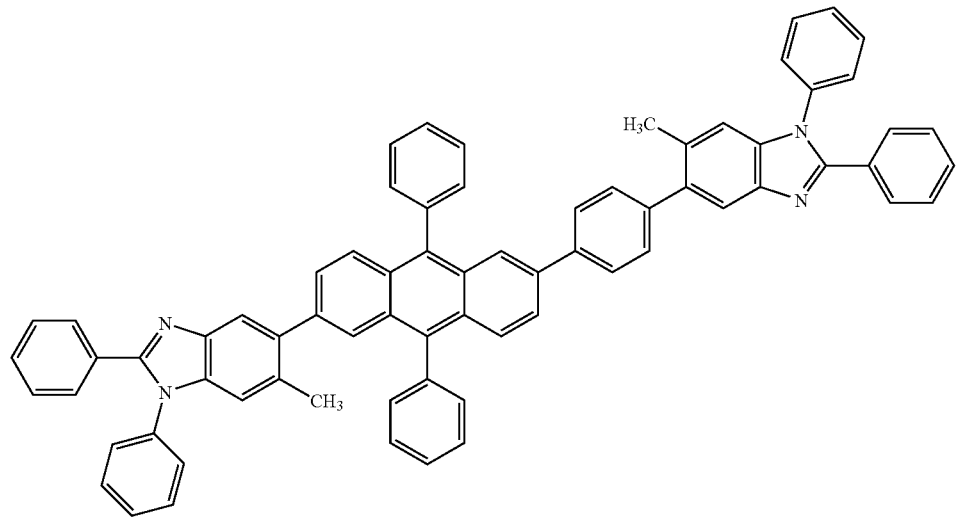
5-37
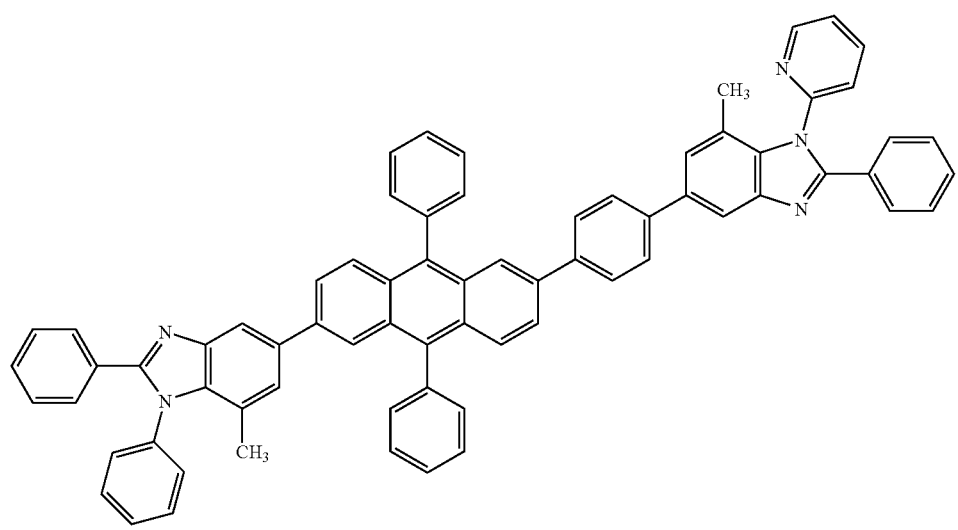
5-38
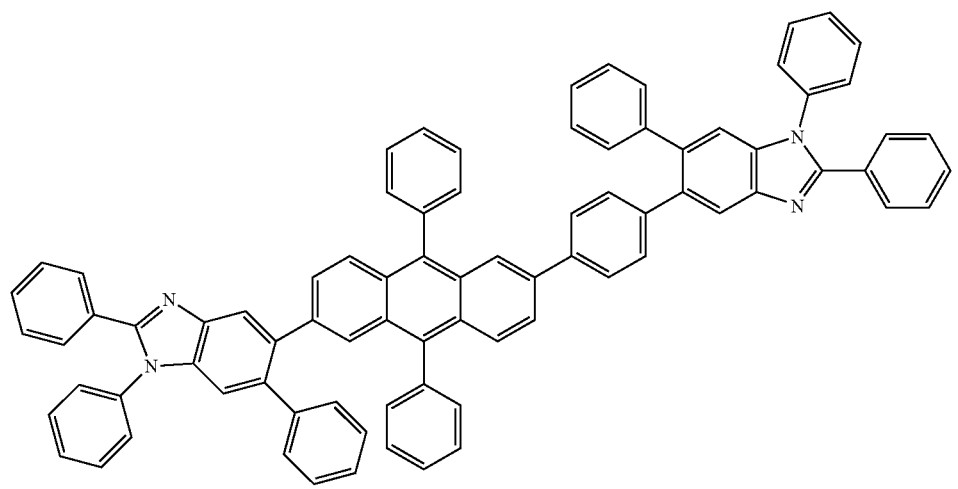

-continued
5-39
5-40
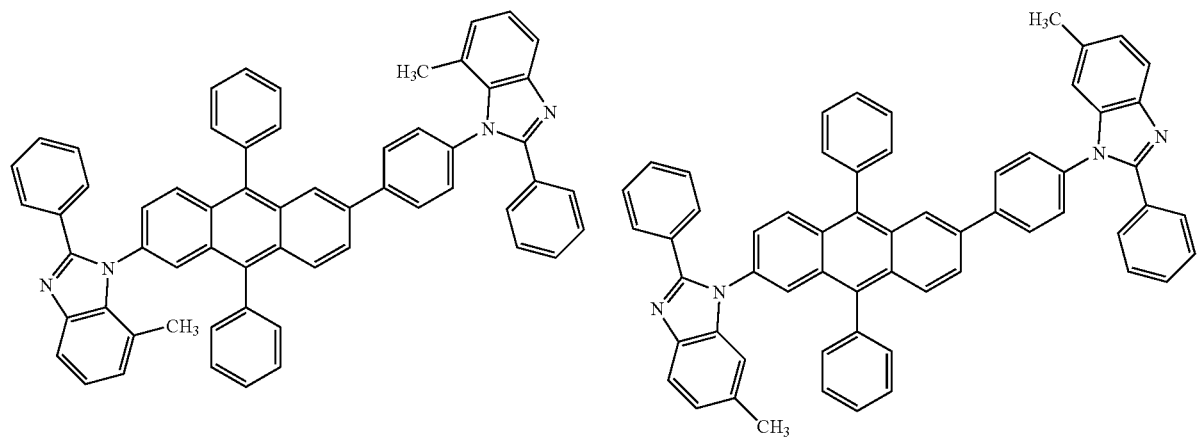
5-41
5-42
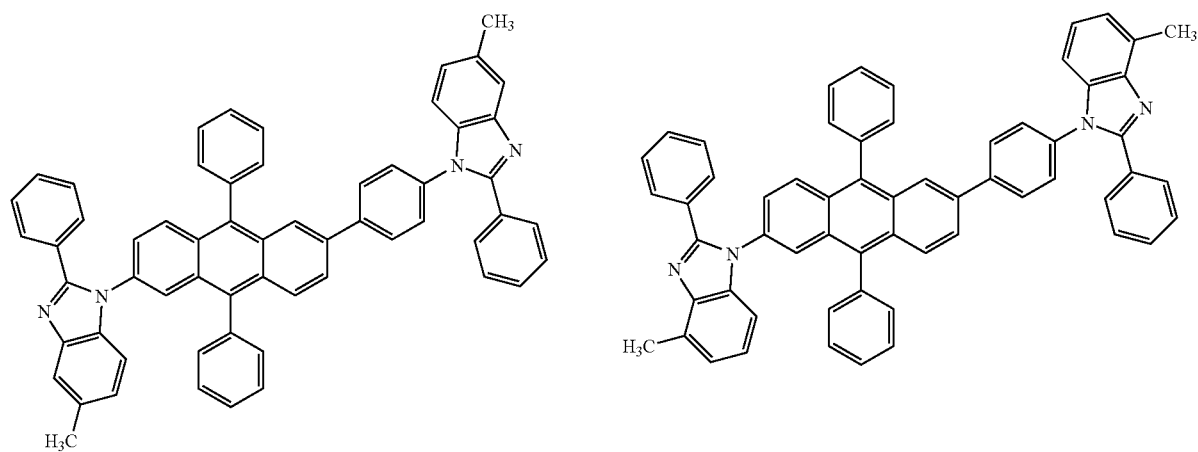
5-43
5-44
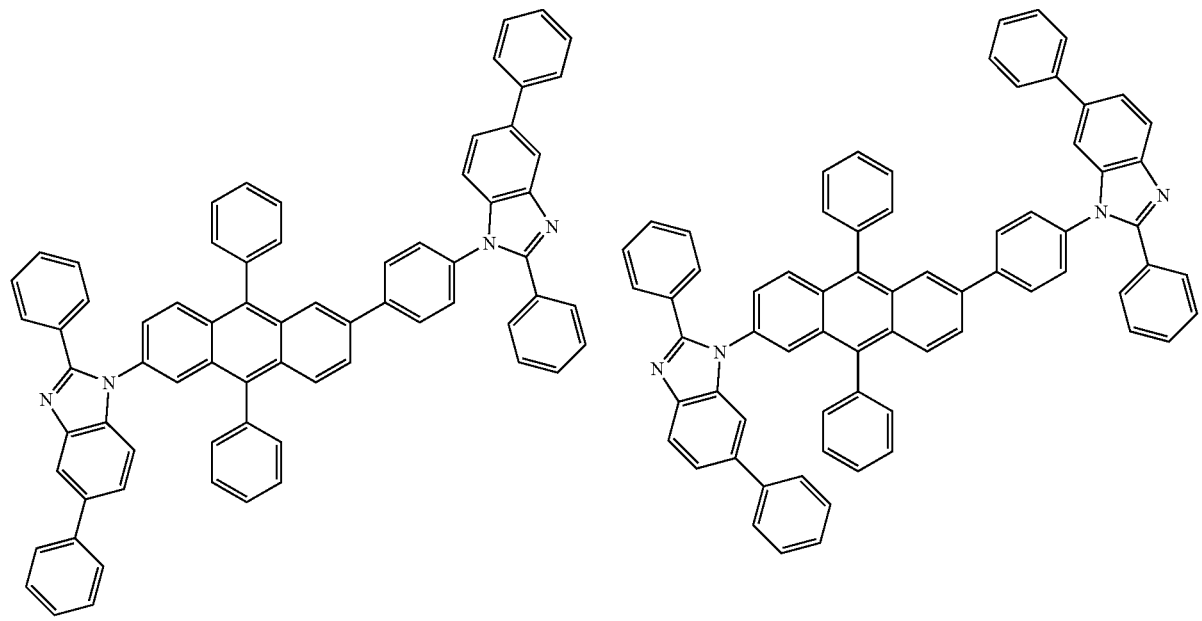

-continued 5-45

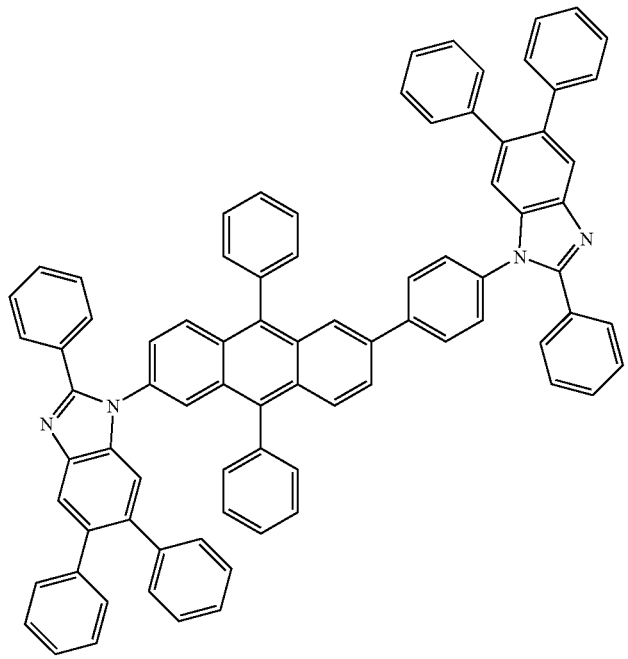

In the organic EL device of the present invention, at least one organic compound layer contains a derivative of heterocyclic compound having a nitrogen atom represented by the general formula (A-1) or (A-2), or preferably any one of the general formulae (1-I) to (5-II). The device is constituted in such a manner that one or more organic thin-film layers having at least a light-emitting layer are sandwiched between a cathode and an anode. Specific examples of the constitution include (anode/hole-injecting layer/light-emitting layer/electron-injecting layer/cathode), (anode/light-emitting layer/electron-injecting layer/cathode), (anode/hole-injecting layer/light-emitting layer/cathode), and (anode/light-emitting layer/cathode).

The derivative of heterocyclic compound having a nitrogen atom of the present invention is preferably incorporated into a light-emitting domain, or is more preferably incorporated into the light-emitting layer. Furthermore, the derivative is preferably incorporated into a hole-injecting layer and/or an electron-injecting layer. A n device constitution may be provided without a hole-injecting layer or without an electron-injecting layer, but an organic EL device having these layers each containing the derivative of heterocyclic compound having a nitrogen atom of the present invention has an advantage, that is, an improvement of light-emitting performance. Alternatively, the hole-injecting layer, the light-emitting layer, and the electron-injecting layer may be sandwiched between a pair of electrodes in a mixed manner. Furthermore, a binder such as a polymer compound may be used to produce a mixed layer in order that each component may be stably present.

Here, description will be given by taking the organic EL device of the present invention of a (anode/hole-injecting layer/light-emitting layer/electron-injecting layer/cathode) type as an example. The organic EL device of the present invention is preferably supported by a substrate. The substrate is not particularly limited, and any substrate generally used for a conventional organic EL device is permitted. For example, a substrate composed of glass, transparent plastic, quartz, or the like can be used.

A positive electrode using, as an electrode material, a metal, alloy, or electroconductive compound having a large work function (4 eV or more), or a mixture of them is preferably used as a positive electrode in the organic EL device of the present invention. Specific examples of such electrode material include: metals such as Au; and conductive transparent materials such as CuI, ITO, $SnO_2$, and ZnO. The positive electrode can be obtained by forming such electrode material into a film by means of a thin-film forming method such as vapor deposition or sputtering. When light emission is taken out of the electrode, the transmittance of the electrode is desirably 10% or more, and the sheet resistance of the electrode is preferably 500 Ω/square or less. The thickness of the electrode, which varies depending on a material for the electrode, is selected from the range of generally about 10 nm to 1 μm, or preferably 10 to 200 nm.

On the other hand, a cathode using, as an electrode material, a metal, alloy, or electroconductive compound having a small work function (less than 4 eV), or a mixture of them is used. Specific examples of such electrode material include sodium, a sodium-potassium alloy, magnesium, a magnesium-silver alloy, lithium, a magnesium/copper mixture, a magnesium-indium alloy, $Al/Al_2O_3$, indium, and an aluminum-lithium alloy. The cathode can be obtained by forming such electrode material into a film by means of a thin-film forming method such as vapor deposition or sputtering. In addition, the sheet resistance of the electrode is preferably 500 Ω/square or less. The thickness of the electrode is selected from the range of generally 10 nm to 500 nm, or preferably 50 to 200 nm. One of the anode and cathode of the organic EL device is conveniently transparent or semitransparent for causing emitted light to pass through the electrode because an efficiency of light emission increases.

The derivative of heterocyclic compound having a nitrogen atom of the present invention is preferably used as a light-emitting material for the light-emitting layer in the device of the present invention. When the derivative of heterocyclic compound having a nitrogen atom is used for any purpose other than the light-emitting layer, the light-emitting material for the light-emitting layer is not particularly limited, and an arbitrary one can be selected from conventionally known compounds and used. A compound having good thin-film forming ability such as: a polycyclic condensed aromatic compound; a benzoxazole-, benzothiazole-, or benzoimidazole-based or like other fluorescent bleach; a metal chelated oxanoid compound; or a distyrylbenzene-based compound can be used as the light-emitting material.

Here, examples of the polycyclic aromatic compound include condensed ring light-emitting substances each including an anthracene, naphthalene, phenanthrene, pyrene, chrysene, or perylene skeleton. To be specific, 1,1,4,4-tetraphenyl-1,3-butadiene, 4,4'-(2,2-diphenylvinyl)biphenyl, or the like can be used. The light-emitting layer may be constituted by one layer composed of one or two or more kinds of those light-emitting materials, or a light-emitting layer containing a compound different from that of the light-emitting layer may be laminated on the light-emitting layer.

Next, the hole-injecting layer in the organic EL device of the present invention is composed of a hole-transmitting compound, and has a function of transmitting a hole injected from the anode to the light-emitting layer. The hole-injecting layer is sandwiched between the anode and the light-emitting layer, with the result that a large number of holes are injected into the light-emitting layer even in a weakened electric field. Moreover, electrons injected into the light-emitting layer from the cathode or the electron-injecting layer are accumulated at an interface in the light-emitting layer owing to the barrier of an electron present at an interface between the light-emitting layer and the hole-injecting layer, so a efficiency of light emission or the like is improved. Accordingly, a device excellent in light-emitting performance can be obtained. Such hole-transmitting compound to be used for the hole-injecting layer is capable of appropriately transmitting a hole to the light-emitting layer when the compound is arranged between two electrodes placed in an electric field and the hole is injected from the anode. For example, a compound having a hole mobility of at least $10^{-6}$ cm$^2$/V·s upon application of an electric field of $10^4$ to $10^6$ V/cm is suitable. The hole-transmitting compound is not particularly limited as long as it has the above preferable property, and an arbitrary one can be selected from those generally used for hole-injecting/transmitting materials in photoconductive materials and from known compounds used for the hole-injecting layers of EL devices.

Examples of the hole-transmitting compound include: copper phthalocyanine; N,N,N',N'-tetraphenyl-4,4'-diaminophenyl; N,N'-diphenyl-N,N'-di(3-methylphenyl)-4,4'-diaminobiphenyl (TPDA); 2,2-bis(4-di-p-tolylaminophenyl)propane; 1,1-bis(4-di-p-tolylaminophenyl)cyclohexane; and N,N,N',N'-tetra-p-tolyl-4,4'-diaminobiphenyl. The crystal of an inorganic semiconductor such as Si, SiC, or CdS, and an amorphous material are also available. The hole-injecting layer may be constituted by one layer composed of one or two or more kinds of those hole-injecting materials, or a hole-injecting layer composed of a compound different from that of the hole-injecting layer may be laminated on the hole-injecting layer.

In addition, the electron-injecting layer in the organic EL device of the present invention is composed of an electron-injecting material, and has a function of transmitting an electron injected from the cathode to the light-emitting layer. In the organic EL device of the present invention, a derivative of heterocyclic compound having a nitrogen atom represented by any one of the general formulae (A-1), (A-2), and (1-I) to (5-II) is preferably used for the electron-injecting layer. When the derivative of heterocyclic compound having a nitrogen atom is used for any purpose other than the electron-injecting layer, the electron-injecting material is not particularly limited, and an arbitrary one can be selected from conventionally known compounds and used. Examples of the electron-injecting material include: a metal complex such as 8-hydroxyquinoline or a derivative thereof; a benzoxazole-based compound; and a benzothiazole-based compound.

A preferred embodiment of the organic EL device of the present invention is a device containing a reductive dopant in a region where an electron is transported or an interfacial region between the cathode and an organic layer. In the present invention, an device containing a reductive dopant in addition to the derivative of heterocyclic compound having a nitrogen atom represented by any one of the general formulae (A-1), (A-2), and (1-I) to (5-II) is preferably exemplified. The term "reductive dopant" as used herein is defined as a substance capable of reducing an electron transportable compound. Therefore, any one of various substances each having certain reducing property can be used. For example, at least one substance selected from the group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal can be suitably used.

Specific examples of a preferable reductive dopant include: at least one alkali metal selected from the group consisting of Na (having a work function of 2.36 eV), K (having a work function of 2.28 eV), Rb (having a work function of 2.16 eV), and Cs (having a work function of 1.95 eV); and at least one alkali earth metal selected from the group consisting of Ca (having a work function of 2.9 eV), Sr (having a work function of 2.0 to 2.5 eV), and Ba (having a work function of 2.52 eV). A reductive dopant having a work function of 2.9 eV or less is particularly preferable. Of those, a more preferable reductive dopant is at least one alkali metal selected from the group consisting of K, Rb, and Cs, a still more preferable reductive dopant is Rb or Cs, and the most preferable reductive dopant is Cs.

Each of those alkali metals has a particularly high reducing ability, so the addition of a relatively small amount of each of them to an electron injection region improves the efficiency of light emission of an organic EL device and prolongs the lifetime of the device. A combination of two or more kinds of those alkali metals is also a preferable reductive dopant having a work function of 2.9 eV or less. In particular, a combination including Cs such as a combination of Cs and Na, Cs and K, Cs and Rb, or Cs, Na, and K is preferable. A combination with Cs enables a reducing ability to be efficiently exerted. In addition, the addition of such combination to an electron injection region improves the efficiency of light emission of an organic EL device and prolongs the lifetime of the device. In addition to an alkali metal, the use of at least one metal compound selected from the group consisting of an alkali metal chalcogenide, an alkali earth metal chalcogenide, a halide of an alkali metal, and a halide of an alkali earth metal provides a similar effect. The use of an alkali metal organic complex or an alkali earth metal organic complex provides a similar effect.

In the present invention, an electron-injecting layer constituted by an insulator or by a semiconductor may be additionally arranged between the cathode and an organic layer. The arrangement of such electron-injecting layer can effectively prevent the leak of a current, and can improve electron-injecting property. At least one metal compound selected from the group consisting of an alkali metal chalcogenide, an alkali earth metal chalcogenide, a halide of an alkali metal, and a halide of an alkali earth metal is preferably used for such insulator. The electron-injecting layer is preferably constituted by such alkali metal chalcogenide or the like because electron-injecting property can be additionally improved.

Specific examples of a preferable alkali metal chalcogenide include $Li_2O$, LiO, $Na_2S$, $Na_2Se$, and NaO. Examples of a preferable alkali earth metal chalcogenide include CaO, BaO, SrO, BeO, BaS, and CaSe. Examples of a preferable halide of an alkali metal include LiF, NaF, KF, LiCl, KCl, and NaCl. Examples of a preferable halide of an alkali earth metal include: fluorides such as $CaF_2$, $BaF_2$, $SrF_2$, $MgF_2$, and $BeF_2$; and halides except fluorides.

Examples of the semiconductor include: a single kind of oxides, nitrides, oxynitrides, and the like each containing at least one element of Ba, Ca, Sr, Yb, Al, Ga, In, Li, Na, Cd, Mg, Si, Ta, Sb, and Zn; and a combination of two or more kinds of them. Each of those inorganic compounds is preferably a microcrystalline or amorphous insulating thin film. When an electron-injecting layer is constituted by such insulating thin film, defects in pixels such as a dark spot can be reduced because a thin film with improved homogeneity is formed. Examples of such inorganic compound include an alkali metal chalcogenide, an alkali earth metal chalcogenide, a halide of an alkali metal, and a halide of an alkali earth metal as described above.

The electron-injecting layer in the organic EL device of the present invention can be obtained by forming the derivative of heterocyclic compound having a nitrogen atom of the present invention into a film by means of a known thin-film forming method such as a vacuum vapor deposition method, a spin coating method, a cast method, or an LB method. The thickness of the electron-injecting layer, which is not particularly limited, is generally about 5 nm to 5 µm. The electron-injecting layer may be constituted by one layer composed of one or more kinds of those electron-injecting materials, or an electron-injecting layer composed of a compound different from that of the above layer may be laminated on the electron-injecting layer. Furthermore, a hole-injecting material by p-type Si or p-type SiC as an inorganic substance or an electron-injecting material by n-type α-Si or n-type α-SiC can be used as an electron-injecting material. For example, an inorganic semiconductor disclosed in WO 90/05998 can be exemplified.

Next, a preferable example of the production of the organic EL device of the present invention will be described. Description will be made by taking a method of producing an organic EL device having the above-described (anode/hole-injecting layer/light-emitting layer/electron-injecting layer/cathode) constitution as an example. At first, a thin film composed of a desired electrode material, for example, an anode material and having a thickness of 1 µm or less, or preferably in the range of 10 to 200 nm is formed on an appropriate substrate by means of a method such as vapor deposition or sputtering, to thereby produce an anode. Next, thin films composed of materials for a hole-injecting layer, a light-emitting layer, and an electron-injecting layer as device materials are formed on the anode. As described above, examples of a thin-film forming method intended for the production include a spin coating method, a cast method, and a vapor deposition method. A vacuum vapor deposition method is preferable because, for example, a homogeneous film can be easily obtained and a pin hole is hardly produced.

When a vapor deposition method is adopted for forming a thin film, the vapor deposition conditions of the method vary depending on the kind of a compound to be used, the target crystalline structure of a molecular deposited film, an association structure, and the like. In general, a boat heating temperature, a degree of vacuum, a vapor deposition rate, a substrate temperature, and a thickness are desirably appropriately selected from the ranges of 50 to 400° C., $10^{-6}$ to $10^{-3}$ Pa, 0.01 to 50 nm/s, −50 to 300° C., and 5 nm to 5 µm, respectively. After the formation of those layers, a thin film composed of a cathode material and having a thickness of 1 µm or less, or preferably in the range of 50 to 200 nm is formed on them by means of a method such as vapor deposition or sputtering, to thereby arrange a cathode. As a result, a desired organic EL device can be obtained. In the production of the organic EL device, the order in which the thin films are formed may be reversed; the cathode, the electron-injecting layer, the light-emitting layer, the hole-injecting/transporting layer, and the anode may be formed in the stated order.

In addition, an example of a method of producing a device composed of an anode, a light-emitting layer, and a cathode in which a hole-injecting layer, the light-emitting layer, and an electron-injecting layer are sandwiched between a pair of electrodes in a mixed manner involves: forming a thin film composed of an anode material on an appropriate substrate; applying a solution composed of a hole-injecting material, a light-emitting material, an electron-injecting material, a binder (such as polyvinyl carbazole, polycarbonate, polyallylate, polyester, or polyether), and the like, or forming a thin film from the solution by means of a dip coating method, to provide the light-emitting layer; and forming a thin film composed of a cathode material on the layer. Here, device materials serving as materials for a light-emitting layer and an electron-injecting layer may be deposited from the vapor on the produced light-emitting layer in a vacuum, and the thin film composed of the cathode material may be formed.

In the case where a DC voltage is applied to the organic EL device thus produced, light emission can be observed when a voltage of about 3 to 50V is applied with the anode and the cathode set to plus (+) polarity and minus (−) polarity, respectively. When a voltage is applied with the polarity of each of the anode and the cathode reversed, no current flows, and no light emission occurs. Furthermore, in the case where an alternating voltage is applied, light emission occurs only when a positive electrode has plus (+) polarity and a negative electrode has minus (−) polarity. The wave form of an alternating voltage to be applied is arbitrary.

EXAMPLES

Hereinafter, the present invention will be described in more detail by way of examples. However, the present invention is not limited to these examples at all.

Synthesis Example 1

A Compound 1-1 was synthesized as described below.

(1-a) Synthesis of 2-bromoanthraquinone 18 g (81 mmol) of copper bromide and 12 mL (101 mmol) of t-butyl nitrite were dispersed into acetonitrile at 65° C., and then 15 g (67 mmol) of 2-aminoanthraquinone were dropped while the solution was vigorously stirred. The mixture was stirred until the generation of a gas was completely stopped. Then, the temperature of the mixture was cooled to room temperature, and 1 L of 20-mass % hydrochloric acid was added. After that, the resultant was extracted with dichloromethane. An organic layer was dried with magnesium sulfate, and the solvent was distilled off under reduced pressure. The residue was purified by means of silica gel column chromatography to obtain 14 g of 2-bromoanthraquinone (75% yield).

(1-b) Synthesis of 2-bromo-9,10-diphenyl-9,9,10,10-tetrahydroanthracene-9,10-diol In an argon atmosphere, 5.4 mL (52 mmol) of bromobenzene were dissolved into 100 mL of dehydrated tetrahydrofuran (THF), and the temperature of the solution was cooled to −78° C. Then, 45 mL of t-butyllithium (in pentane, 1.5 mol/L) were dropped. After the mixture had been stirred at −78° C. for 1 hour, 4.9 g (17 mmol) of 2-bromoanthraquinone were added. After an aqueous solution of ammonium chloride had been added, the resultant was extracted with dichloromethane. An organic layer was dried with magnesium sulfate, and the solvent was distilled off under reduced pressure. The resultant solid was washed with ethanol to obtain 6.8 g of 2-bromo-9,10-diphenyl-9,9,10,10-tetrahydroanthracene-9,10-diol (90% yield).

(1-c) Synthesis of 2-bromo-9,10-diphenylanthracene

In an argon atmosphere, 4.5 g (10 mmol) of 2-bromo-9,10-diphenyl-9,9,10,10-tetrahydroanthracene-9,10-diol were dissolved into acetic acid, and 17 g (102 mmol) of potassium iodide and 18 g (167 mmol) of $NaH_2PO_2$ were added. The mixture was refluxed under heating while being vigorously stirred for 3 hours. The temperature of the mixture was cooled to room temperature, and then the mixture was filtered. The resultant solid was washed with water and methanol, and was then dried under reduced pressure to obtain 3.5 g of 2-bromo-9,10-diphenylanthracene (85% yield).

(1-d) Synthesis of 9,10-diphenylanthracene-2-boronic acid

In an argon atmosphere, 50 mL of dehydrated THF were added to 3.5 g (8.6 mmol) of 2-bromo-9,10-diphenylanthracene, and the temperature of the mixture was cooled to −78° C. Then, 6.0 mL of n-butyllithium (in hexane, 1.6 mol/L) were dropped. After the mixture had been stirred at −78° C. for 1 hour, the temperature of the mixture was increased to 0° C. The temperature of the mixture was cooled to −78° C. again, and 2.9 mL (26 mmol) of trimethoxyborane were dropped. The mixture was stirred at −78° C. for 1 hour, and was then stirred at room temperature for 2 hours. 50 mL of 10-mass % hydrochloric acid were added, and the whole was stirred for 1 hour, followed by filtration. The resultant solid was washed with toluene to obtain 2.6 g of 9,10-diphenylanthracene-2-boronic acid (80% yield).

(1-e) Synthesis of 4-bromo-2-nitrodiphenylamine 10 g (36 mmol) of 2,5-dibromonitrobenzene, 8.8 g (110 mmol) of sodium acetate, and 6.6 g (71 mmol) of aniline were stirred under heating at 160° C. for 9 hours in an argon atmosphere. The temperature of the reaction solution was cooled to room temperature, and the solution was extracted with ethylacetate and water. After an aqueous layer had been removed, an organic layer was washed with 10-mass % hydrochloric acid, a 10-mass % aqueous solution of potassium carbonate, and a saturated sodium chloride solution, and was dried with magnesium sulfate. The solvent was distilled off under reduced pressure, and the residue was purified by means of silica gel column chromatography to obtain 9.9 g of 4-bromo-2-nitrodiphenylamine (95% yield).

(1-f) Synthesis of 5-bromo-2-(N-phenylamino)-benzanilide 9.9 g (34 mmol) of 4-bromo-2-nitrodiphenylamine were dissolved into 75 mL of tetrahydrofuran. While the solution was stirred at room temperature in a nitrogen atmosphere, a solution of 30 g (170 mmol) of sodium hydrosulfite in 100 mL of water was added. Furthermore, 10 mL of methanol were added, and the whole was stirred for 3 hours. Next, 75 mL of ethyl acetate were added, and then a solution of 5.7 g (68 mmol) of sodium hydrogen carbonate in 60 mL of water was added. Furthermore, a solution of 4.8 g (34 mmol) of benzoyl chloride in 25 mL of ethyl acetate was dropped, and the whole was stirred at room temperature for 5 hours. The resultant was extracted with ethyl acetate, sequentially washed with a 10-mass % aqueous solution of potassium carbonate and a saturated sodium chloride solution, and dried with anhydrous magnesium sulfate. The solvent was distilled off under reduced pressure, with the result that 5.6 g of 5-bromo-2-(N-phenylamino)-benzanilide were obtained (45% yield).

(1-g) Synthesis of 5-bromo-1,2-diphenyl-1H-benzimidazole 5.6 g (15 mmol) of 5-bromo-2-(N-phenylamino)-benzanilide were suspended into 60 mL of xylene, 0.88 g (4.6 mmol) of p-toluenesulfonic acid monohydrate was added, and the whole was subjected to azeotropic dehydration while being refluxed under heating for 5 hours. The temperature of the reaction solution was cooled to room temperature, and the solvent was distilled off. The resultant solid was washed with ethanol to obtain 2.5 g of 5-bromo-1,2-diphenyl-1H-benzimidazole (46% yield).

(1-h) Synthesis of 5-(4-chlorophenyl)-1,2-diphenyl-1H-benzimidazole 2.5 g (7.2 mmol) of 5-bromo-1,2-diphenyl-1H-benzimidazole, 1.2 g (7.9 mmol) of 4-chlorophenylboronic acid, and 0.17 g (0.14 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the resultant had been stood to cool, an aqueous layer was removed and an organic layer was dried with magnesium sulfate. After the solvent had been distilled off under reduced pressure, the resultant solid was purified by means of silica gel column chromatography to obtain 2.3 g of 5-(4-chlorophenyl)-1,2-diphenyl-1H-benzimidazole (83% yield).

(1-i) Synthesis of 1,2-diphenyl-5-[4-(9,10-diphenylanthracen-2-yl)phenyl]-1H-benzimidazole 2.3 g (6.0 mmol) of 5-(4-chlorophenyl)-1,2-diphenyl-1H-benzimidazole, 2.5 g (6.6 mmol) of 9,10-diphenylanthracene-2-boronic acid, tris(dibenzylideneacetone)dipalladium (0) (0.14 g, 0.15 mmol), and cesium carbonate (4.7 g, 14 mmol) were suspended into 20 mL of anhydrous dioxane, a solution of tricyclohexylphosphine/toluene (25 mass %, 0.49 ml, 0.43 mmol) was added, and the whole was stirred at 80° C. for 10 hours. The reaction mixture was diluted with 200 mL of toluene and 100 mL of water, and was filtered through Celite 545 for removing Pd black. An organic layer was fractionated from the filtrate, washed with 50 mL of a saturated sodium chloride solution, and dried with anhydrous magnesium sulfate, and the solvent was distilled off, with the result that red oil was obtained. The oil was purified by means of silica gel column chromatography to obtain 3.0 g of a greenish white solid (75% yield). Mass spectral analysis confirmed that the solid was a target product. The solid had an m/e of 674 with respect to a molecular weight of 674.27.

Synthesis Example 2

A Compound 1-2 was synthesized as described below.

(2-a) Synthesis of 2-bromo-9,10-di(2-naphtyl)-9,9,10,10-tetrahydroanthracene-9,10-diol In an argon atmosphere, 11 g (53 mmol) of 2-bromonaphthalene were dissolved into 100 mL of dehydrated tetrahydrofuran (THF), and the temperature of the solution was cooled to −78° C. Then, 45 mL of t-butyllithium (in pentane, 1.5 mol/L) were dropped. After the mixture had been stirred at −78° C. for 1 hour, 6.3 g (22 mmol) of 2-bromoanthraquinone were added. After an aqueous solution of ammonium chloride had been added, the resultant was extracted with dichloromethane. An organic layer was dried with magnesium sulfate, and the solvent was distilled off under reduced pressure. The resultant solid was washed with ethanol to obtain 11 g of 2-bromo-9,10-di(2-naphtyl)-9,9,10,10-tetrahydroanthracene-9,10-diol (94% yield).

(2-b) Synthesis of 2-bromo-9,10-di(2-naphtyl)anthracene

In an argon atmosphere, 11 g (21 mmol) of 2-bromo-9,10-dinaphthyl-9,9,10,10-tetrahydroanthracene-9,10-diol were dissolved into acetic acid, and 34 g (206 mmol) of potassium iodide and 36 g (340 mmol) of $NaH_2PO_2$ were added. The mixture was refluxed under heating while being vigorously stirred for 3 hours. The temperature of the mixture was cooled to room temperature, and then the mixture was filtered. The resultant solid was washed with water and methanol, and was then dried under reduced pressure to obtain 10 g of 2-bromo-9,10-diphenylanthracene (16% yield).

(2-c) Synthesis of 9,10-di(2-naphtyl)anthracene-2-boronic acid

In an argon atmosphere, 100 mL of dehydrated THF were added to 10 g (20 mmol) of 2-bromo-9,10-di(2-naphtyl)anthracene, and the temperature of the mixture was cooled to −78° C. Then, 14 mL of n-butyllithium (in hexane, 1.6 mol/L) were dropped. After the mixture had been stirred at −78° C. for 1 hour, the temperature of the mixture was increased to 0° C. The temperature of the mixture was cooled to −78° C. again, and 6.6 mL (60 mmol) of trimethoxyborane were added. The mixture was stirred at −78° C. for 1 hour, and was then stirred at room temperature for 2 hours. 100 mL of 10-mass % hydrochloric acid were added, and the whole was stirred for 1 hour, followed by filtration. The resultant solid was washed with toluene to obtain 4.7 g of 9,10-diphenylanthracene-2-boronic acid (50% yield).

(2-d) Synthesis of 1,2-diphenyl-5-[4-[9,10-di(2-naphthyl)phenylanthracen-2-yl]phenyl]-1H-benzimidazole 2.3 g (6.0 mmol) of 5-(4-chlorophenyl)-1,2-diphenyl-1H-benzimidazole, 3.1 g (6.6 mmol) of 9,10-di(2-naphthyl)anthracene-2-boronic acid, tris(dibenzylideneacetone)dipalladium (0) (0.14 g, 0.15 mmol), and cesium carbonate (4.7 g, 14 mmol) were suspended into 20 mL of anhydrous dioxane, a solution of tricyclohexylphosphine/toluene (25 mass %, 0.49 ml, 0.43 mmol) was added, and the whole was stirred at 80° C. for 10 hours. The reaction mixture was diluted with 200 mL of toluene and 100 mL of water, and was filtered through Celite 545 for removing Pd black. An organic layer was fractionated from the filtrate, washed with 50 mL of a saturated sodium chloride solution, and dried with anhydrous magnesium sulfate, and the solvent was distilled off, with the result that red oil was obtained. The oil was purified by means of silica gel column chromatography to obtain 3.2 g of a greenish white solid (69% yield). Mass spectral analysis confirmed that the solid was a target product. The solid had an m/e of 774 with respect to a molecular weight of 774.30.

Synthesis Example 3

A Compound 1-9 was synthesized as described below.

(3-a) Synthesis of 4-bromo-N-methyl-2-nitroaniline 5.0 g (33 mmol) of N-methyl-2-nitroaniline and 5.9 g (33 mmol) of N-bromosuccinimide were added with 60 mL of acetic acid, and the whole was refluxed under heating for 7 hours. After the completion of the reaction, the reaction solution was poured into 500 mL of water, and the precipitated solid was filtered out. The solid that had been filtered out was dissolved into ethyl acetate and dried with magnesium sulfate. After filtration, the solvent was distilled off under reduced pressure, and the residue was dried at room temperature under reduced pressure to obtain 7.1 g of the orange solid of 4-bromo-N-methyl-2-nitroaniline (93% yield).

(3-b) Synthesis of 4'-bromo-N-methyl-2'-nitro-benzanilide 6.8 g (29 mmol) of 4-bromo-N-methyl-2-nitroaniline were dissolved into 20 mL of pyridine. Furthermore, 5.0 g (35 mmol) of benzoyl chloride were added, and the whole was stirred under heating at 90° C. for 7 hours in an argon atmosphere. After the completion of the reaction, 200 mL of ethyl acetate were added, and the whole was washed with 10-mass % hydrochloric acid, 10-mass % $K_2CO_3$, and a saturated sodium chloride solution, and dried with magnesium sulfate. After filtration, the solvent was distilled off under reduced pressure, and the residue was purified by means of silica gel column chromatography to obtain 9.5 g of 4'-bromo-N-methyl-2'-nitro-benzanilide as a greenish white solid (96% yield).

(3-c) Synthesis of 4'-bromo-N-methyl-2'-amino-benzanilide 9.5 g (28 mmol) of 4'-bromo-N-methyl-2'-nitro-benzanilide were dissolved into 100 mL of tetrahydrofuran. While the solution was stirred at room temperature in an argon atmosphere, a solution of 25 g (142 mmol) of sodium hydrosulfite in 90 mL of water was added. Furthermore, 10 mL of methanol were added, and the whole was stirred for 3 hours. Next, 100 mL of ethyl acetate were added, and then a solution of 12 g (142 mmol) of sodium hydrogen carbonate in 125 mL of water was added. After having been stirred for 1 hour, the resultant was extracted with ethyl acetate. An aqueous layer was removed, and an organic layer was washed with a 10-mass % aqueous solution of $K_2CO_3$ and a saturated sodium chloride solution, and dried with magnesium sulfate. After filtration, the solvent was distilled off under reduced pressure, with the result that 7.8 g of 4'-bromo-N-methyl-2'-amino-benzanilide were obtained as a white solid (90% yield). The coarse product was directly used for the next reaction.

(3-d) Synthesis of 5-bromo-1-methyl-2-phenyl-1H-benzimidazole 7.8 g (26 mmol) of 4'-bromo-N-methyl-2'-amino-benzanilide were suspended into 50 mL of xylene. Then, 1.5 g (7.7 mmol) of p-toluenesulfonic acid monohydrate was added, and the whole was refluxed under heating for 7 hours. After the completion of the reaction, the resultant was filtered. The resultant solid was dissolved into methylene chloride, washed with 10-mass % $K_2CO_3$ and a saturated sodium chloride solution, and dried with magnesium sulfate. After that, the solvent was distilled off under reduced pressure. The filtrate was washed with 10-mass % $K_2CO_3$ and a saturated sodium chloride solution, and dried with magnesium sulfate. After that, the solvent was distilled off under reduced pressure. The resultant two residues were coalesced, and the resultant was purified by means of silica gel column chromatography to obtain 6.5 g of 5-bromo-1-methyl-2-phenyl-1H-benzimidazole as a white solid (89% yield).

(3-e) Synthesis of 5-(4-chlorophenyl)-1-methyl-2-phenyl-1H-benzimidazole 2.0 g (7.2 mmol) of 5-bromo-1-methyl-2-phenyl-1H-benzimidazole, 1.2 g (7.9 mmol) of 4-chlorophenylboronic acid, and 0.17 g (0.14 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the resultant had been stood to cool, an aqueous layer was removed and an organic layer was dried with magnesium sulfate. After the solvent had been distilled off under reduced pressure, the resultant solid was purified by means of silica gel column chromatography to obtain 2.0 g of 5-(4-chlorophenyl)-1,2-diphenyl-1H-benzimidazole (87% yield).

(3-f) Synthesis of 5-[4-(9,10-diphenylanthracen-2-yl)phenyl]-1-methyl-2-phenyl-1H-benzimidazole 1.9 g (6.0 mmol) of 5-(4-chlorophenyl)-1,2-diphenyl-1H-benzimidazole, 2.5 g (6.6 mmol) of 9,10-diphenylanthracene-2-boronic acid, tris(dibenzylideneacetone)dipalladium (0) (0.14 g, 0.15 mmol), and cesium carbonate (4.7 g, 14 mmol) were suspended into 20 mL of anhydrous dioxane, a solution of tricyclohexylphosphine/toluene (25 mass %, 0.49 ml, 0.43 mmol) was added, and the whole was stirred at 80° C. for 10 hours. The reaction mixture was diluted with 200 mL of toluene and 100 mL of water, and was filtered through Celite 545 for removing Pd black. An organic layer was fractionated from the filtrate, washed with 50 mL of a saturated sodium chloride solution, and dried with anhydrous magnesium sulfate, and the solvent was distilled off, with the result that red oil was obtained. The oil was purified by means of silica gel column chromatography to obtain 3.2 g of a greenish white solid (87% yield). Mass spectral analysis confirmed that the solid was a target product. The solid had an m/e of 612 with respect to a molecular weight of 612.26.

Synthesis Example 4

A Compound 1-41 was synthesized as described below.

(4-a) Synthesis of 2-bromoanthraquinone 18 g (81 mmol) of copper bromide and 12 mL (101 mmol) oft-butyl nitrite were dispersed into acetonitrile at 65° C., and then 15 g (67 mmol) of 2-aminoanthraquinone were dropped while the solution was vigorously stirred. The mixture was stirred until the generation of a gas was completely stopped. Then, the temperature of the mixture was cooled to room temperature, and 1 L of 20-mass % hydrochloric acid was added. After that, the resultant was extracted with dichloromethane. An organic layer was dried with magnesium sulfate, and the solvent was distilled off under reduced pressure. The residue was purified by means of silica gel column chromatography to obtain 14 g of 2-bromoanthraquinone (75% yield).

(4-b) Synthesis of 2-bromo-9,10-diphenyl-9,9,10,10-tetrahydroanthracene-9,10-diol In an argon atmosphere, 5.4 mL (52 mmol) of bromobenzene were dissolved into 100 mL of dehydrated tetrahydrofuran (THF), and the temperature of the solution was cooled to −78° C. Then, 45 mL of t-butyllithium (in pentane, 1.5 mol/L) were dropped. After the mixture had been stirred at −78° C. for 1 hour, 4.9 g (17 mmol) of 2-bromoanthraquinone were added. After an aqueous solution of ammonium chloride had been added, the resultant was extracted with dichloromethane. An organic layer was dried with magnesium sulfate, and the solvent was distilled off under reduced pressure. The resultant solid was washed with ethanol to obtain 6.8 g of 2-bromo-9,10-diphenyl-9,9,10,10-tetrahydroanthracene-9,10-diol (90% yield).

(4-c) Synthesis of 2-bromo-9,10-diphenylanthracene

In an argon atmosphere, 4.5 g (10 mmol) of 2-bromo-9,10-diphenyl-9,9,10,10-tetrahydroanthracene-9,10-diol were dissolved into acetic acid, and 17 g (102 mmol) of potassium iodide and 18 g (167 mmol) of $NaH_2PO_2$ were added. The mixture was refluxed under heating while being vigorously stirred for 3 hours. The temperature of the mixture was cooled to room temperature, and then the mixture was filtered. The resultant solid was washed with water and methanol, and was then dried under reduced pressure to obtain 3.5 g of 2-bromo-9,10-diphenylanthracene (85% yield).

(4-d) Synthesis of 9,10-diphenylanthracene-2-boronic acid

In an argon atmosphere, 50 mL of dehydrated THF were added to 3.5 g (8.6 mmol) of 2-bromo-9,10-diphenylanthracene, and the temperature of the mixture was cooled to −78° C. Then, 6.0 mL of n-butyllithium (in hexane, 1.6 mol/L) were dropped. After the mixture had been stirred at −78° C. for 1 hour, the temperature of the mixture was increased to 0° C. The temperature of the mixture was cooled to −78° C. again, and 2.9 mL (26 mmol) of trimethoxyborane were dropped. The mixture was stirred at −78° C. for 1 hour, and was then stirred at room temperature for 2 hours. 50 mL of 10-mass % hydrochloric were added, and the whole was stirred for 1 hour, followed by filtration. The resultant solid was washed with toluene to obtain 2.6 g of 9,10-diphenylanthracene-2-boronic acid (80% yield).

(4-e) Synthesis of 4-bromo-2'-nitrodiphenylamine 10 g (50 mmol) of 2-bromonitrobenzene, 13 g (163 mmol) of sodium acetate, and 10 g (59 mmol) of 4-bromoaniline were stirred under heating at 180° C. for 8 hours in an argon atmosphere. The temperature of the reaction solution was cooled to room temperature, and the solution was diluted with ethyl acetate and filtered. After the filtrate had been concentrated, the residue was washed with methanol to obtain 3.8 g of 4-bromo-2'-nitrodiphenylamine (22% yield).

(4-f) Synthesis of N-[2-(4-bromophenylamino)phenyl]benzamide 3.8 g (13 mmol) of 4-bromo-2'-nitrodiphenylamine were dissolved into 30 mL of THF. While the solution was stirred at room temperature in an argon atmosphere, a solution of 11 g (64 mmol) of sodium hydrosulfite in 30 mL of water was dropped. After having been stirred for 5 hours, the mixture was added with 20 mL of ethyl acetate and a solution of 2.2 g (26 mmol) of sodium hydrogen carbonate in 20 mL of water. Furthermore, a solution of 2.5 g (18 mmol) of benzoyl chloride in 10 mL of ethyl acetate was dropped, and the whole was stirred at room temperature for 1 hour. The resultant was extracted with ethylacetate, sequentially washed with a 10-mass % aqueous solution of potassium carbonate, water, and a saturated sodium chloride solution, and dried with anhydrous sodium sulfate. The solvent was distilled off under reduced pressure, with the result that 2.1 g of N-[2-(4-bromophenylamino)phenyl]benzamide were obtained (45% yield).

(4-g) Synthesis of 1-(4-bromophenyl)-2-phenyl-1H-benzimidazole 2.1 g (5.7 mmol) of N-[2-(4-bromophenylamino)phenyl]benzamide were suspended into 30 mL of xylene, 0.6 g (2.9 mmol) of p-toluenesulfonic acid monohydrate was added, and the whole was refluxed under heating for 3 hours. After the resultant had been stood to cool, the reaction solution was added with ethyl acetate, dichloromethane, and water for filtering insoluble matter out. An organic layer was extracted from a mother liquor, washed with water and a saturated sodium chloride solution, and dried with anhydrous sodium sulfate, and the solvent was distilled off under reduced pressure. The residue was purified by means of silica gel column chromatography to obtain 1.0 g of 1-(4-bromophenyl)-2-phenyl-1H-benzimidazole (52% yield).

(4-h) Synthesis of 1-[4-(9,10-diphenylanthracen-2-yl)phenyl]-2-phenyl-1H-benzimidazole 1.0 g (2.9 mmol) of 1-(4-bromophenyl)-2-phenyl-1H-benzimidazole, 1.2 g (3.2 mmol) of 9,10-diphenylanthracene-2-boronic acid, and 0.067 g (0.058 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the completion of the reaction, the resultant was filtered, and the resultant solid was washed with water, methanol, and toluene to obtain 1.6 g of a greenish white solid (90% yield). Mass spectral analysis confirmed that the solid was a target product. The solid had an m/e of 598 with respect to a molecular weight of 598.24.

Synthesis Example 5

A Compound 1-42 was synthesized as described below.

(5-a) Synthesis of 1-[4-[9,10-di(2-naphtyl)anthracen-2-yl]phenyl]-2-phenyl-1H-benzimidazole 1.0 g (2.9 mmol) of 1-(4-bromophenyl)-2-phenyl-1H-benzimidazole, 1.5 g (3.2 mmol) of 9,10-di(2-naphtyl)anthracene-2-boronic acid, and 0.067 g (0.058 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the completion of the reaction, the resultant was filtered, and the resultant solid was washed with water, methanol, and toluene to obtain 1.7 g of a greenish white solid (84% yield). Mass spectral analysis confirmed that the solid was a target product. The solid had an m/e of 698 with respect to a molecular weight of 698.27.

Synthesis Example 6

A Compound 1-43 was synthesized in the same manner as in the synthesis of the compound 1-41 except that 2-bromo-3,5-diphenylbenzene was used instead of bromobenzene in the step (4-b). Mass spectral analysis confirmed that the compound was a target product. The compound had an m/e of 902 with respect to a molecular weight of 902.37.

Synthesis Example 7

A Compound 1-44 was synthesized in the same manner as in the synthesis of the Compound 1-41 except that 2-bromo biphenyl was used instead of bromobenzene in the step (4-b). Mass spectral analysis confirmed that the compound was a target product. The compound had an m/e of 750 with respect to a molecular weight of 750.30.

Synthesis Example 8

A Compound 1-45 was synthesized in the same manner as in the synthesis of the Compound 1-41 except that 1-bromo naphthalene was used instead of bromobenzene in the step (4-b). Mass spectral analysis confirmed that the compound was a target product. The compound had an m/e of 698 with respect to a molecular weight of 698.27.

Synthesis Example 9

A Compound 2-2 was synthesized as described below.

(9-a) Synthesis of 2,6-dibromoanthraquinone 23.8 g (100 mmol) of 2,6-diaminoanthraquinone were dispersed into a 48-mass % aqueous solution of hydrogen bromide, and then 14.1 g (204 mmol) of sodium nitrite were added. After the generation of a gas had been completely stopped, 63 mL of an aqueous solution of 30 g (206 mmol) of copper bromide/48-mass % hydrogen bromide were dropped together with 50 mL of ethanol. The reaction solution was gradually heated, and was refluxed under heating. The reaction solution was stood to cool to room temperature, and water was added. The precipitated solid was filtered out and washed with water. The resultant solid was purified by means of silica gel column chromatography to obtain 10.0 g of 2,6-dibromoanthraquinone (27% yield).

(9-b) Synthesis of 2,6-dibromo-9,10-di(2-naphtyl)-9,9,10,10-tetrahydroanthracene-9,10-diol In an argon atmosphere, 11 g (53 mmol) of 2-bromonaphthalene were dissolved into 100 mL of dehydrated THF, and the temperature of the solution was cooled to −78° C. Then, 45 mL of t-butyllithium (in pentane, 1.5 mol/L) were dropped. After the mixture had been stirred at −78° C. for 1 hour, 8.1 g (22 mmol) of 2,6-dibromoanthraquinone were added. After an aqueous solution of ammonium chloride had been added, the resultant was extracted with dichloromethane. An organic layer was dried with magnesium sulfate, and the solvent was distilled off under reduced pressure. The resultant solid was washed with ethanol to obtain 12 g of 2,6-dibromo-9,10-(2-naphtyl)-9,9,10,10-tetrahydroanthracene-9,10-diol (90% yield).

(9-c) Synthesis of 2,6-dibromo-9,10-di(2-naphtyl)anthracene

In an argon atmosphere, 12 g (19 mmol) of 2,6-dibromo-9,10-di(2-naphtyl)-9,9,10,10-tetrahydroanthracene-9,10-diol were dissolved into acetic acid, and 31 g (186 mmol) of potassium iodide and 33 g (307 mmol) of $NaH_2PO_2$ were added. The mixture was refluxed under heating while being vigorously stirred for 3 hours. The temperature of the mixture was cooled to room temperature, and then the mixture was filtered. The resultant solid was washed with water and methanol, and was then dried under reduced pressure to obtain 10 g of 2-bromo-9,10-diphenylanthracene (89% yield).

(9-d) Synthesis of 2,6-bis(4-chlorophenyl)-9,10-di(2-naphthyl)anthracene 5.0 g (8.5 mmol) of 2-bromo-9,10-diphenylanthracene, 2.9 g (18.7 mmol) of 4-chlorophenylboronic acid, and 0.20 g (0.17 mmol) of tetrakis(triphenylphosphine)palladium were dissolved into 50 mL of 1,2-dimethoxyethane. Then, 25 mL of a 2 M aqueous solution of sodium carbonate were added, and the whole was refluxed under heating for 8 hours in an argon atmosphere. The resultant was stood to cool. After the completion of the reaction, the resultant was filtered, and the resultant solid was washed with water, methanol, and toluene to obtain 4.8 g of 2,6-bis(4-chlorophenyl)-9,10-di(2-naphthyl)anthracene (86% yield).

(9-e) Synthesis of 1,2-diphenyl-1H-benzimidazole-5-boronic acid

In an argon atmosphere, 10 g (29 mmol) of 5-bromo-1,2-diphenyl-1H-benzimidazole were dissolved into 100 mL of dehydrated THF, and the temperature of the solution was cooled to −78° C. Then, 20 mL of n-butyllithium (in hexane, 1.6 mol/L) were dropped. After the mixture had been stirred at −78° C. for 1 hour, the temperature of the mixture was increased to 0° C. The temperature of the mixture was cooled to −78° C. again, and 9.7 mL (87 mmol) of trimethoxyborane were dropped. The mixture was stirred at −78° C. for 1 hour, and was then stirred at room temperature for 2 hours. 100 mL of 10-mass % hydrochloric acid were added, and the whole was stirred for 1 hour, followed by filtration. The organic layer of the filtrate was washed with a saturated sodium chloride solution and dried with magnesium sulfate. The solvent was distilled off under reduced pressure, and the residue was purified by means of silica gel column chromatography to obtain 3.2 g of 1,2-diphenyl-1H-benzimidazole-5-boronic acid (35% yield).

(9-f) Synthesis of 2,6-bis[4-(1,2-diphenyl-1H-benzimidazol-5-yl)-phenyl]-9,10-di(2-naphthyl)anthracene 2.0 g (3.1 mmol) of 2,6-bis(4-chlorophenyl)-9,10-di(2-naphthyl)anthracene, 2.1 g (6.8 mmol) of 1,2-di-1H-benzimidazol-5-boronic acid, tris(dibenzylideneacetone)dipalladium (0) (0.14 g, 0.16 mmol), and cesium carbonate (1.4 g, 7.44 mmol) were suspended into 20 mL of anhydrous dioxane, a solution of tricyclohexylphosphine/toluene (25 mass %, 0.13 ml, 0.11 mmol) was added, and the whole was stirred at 80° C. for 10 hours. The reaction mixture was diluted with 100 mL of toluene and 500 mL of water, and was filtered through Celite 545 for removing Pd black. An organic layer was fractionated from the filtrate, washed with 50 mL of a saturated sodium chloride solution, and dried with anhydrous magnesium sulfate, and the solvent was distilled off, with the result that red oil was obtained. The oil was purified by means of silica gel column chromatography to obtain 2.6 g of a greenish white solid (82% yield). Mass spectral analysis confirmed that the solid was a target product. The solid had an m/e of 1,118 with respect to a molecular weight of 1,118.43.

Synthesis Example 10

A Compound 2-12 was synthesized as described below.

(10-a) Synthesis of 4-(2-phenyl-1H-benzimidazol-1-yl)phenylboronic acid

In an argon atmosphere, 10 g (29 mmol) of 1-(4-bromophenyl)-phenyl-1H-benzimidazole were dissolved into 100 mL of dehydrated THF, and the temperature of the solution was cooled to −78° C. Then, 20 mL of n-butyllithium (in hexane, 1.6 mol/L) were dropped. After the mixture had been stirred at −78° C. for 1 hour, the temperature of the mixture was increased to 0° C. The temperature of the mixture was cooled to −78° C. again, and 9.7 mL (87 mmol) of trimethoxyborane were dropped. The mixture was stirred at −78° C. for 1 hour, and was then stirred at room temperature for 2 hours. 100 mL of 10-mass % hydrochloric acid were added, and the whole was stirred for 1 hour, followed by filtration. The organic layer of the filtrate was washed with a saturated sodium chloride solution and dried with magnesium sulfate. The solvent was distilled off under reduced pressure, and the residue was purified by means of silica gel column chromatography to obtain 4.2 g of 4-(2-phenyl-1H-benzimidazol-1-yl)phenylboronic acid (46% yield).

(10-b) Synthesis of 2,6-bis[4-(2-phenyl-1H-benzimidazol-1-yl)-phenyl]-9,10-di(2-naphthyl)anthracene 2.0 g (3.4 mmol) of 2,6-dibromo-9,10-di(2-naphthyl)anthracene, 2.4 g (7.5 mmol) of 4-(2-phenyl-1H-benzimidazol-1-yl)phenylboronic acid, and 0.16 g (0.14 mmol) of tetrakis(triphenylphosphine)palladium were dissolved into 30 mL of 1,2-dimethoxyethane. Then, 15 mL of a 2 M aqueous solution of sodium carbonate were added, and the whole was refluxed under heating for 8 hours in an argon atmosphere. The resultant was stood to cool. After the completion of the reaction, the resultant was filtered, and the resultant solid was washed with water, methanol, and toluene to obtain 2.4 g of a greenish white solid (73% yield). Mass spectral analysis confirmed that the solid was a target product. The solid had an m/e of 966 with respect to a molecular weight of 966.37.

Synthesis Example 11

A Compound 3-2 was synthesized as described below.

(11-a) Synthesis of 1,2-diphenyl-5-[9,10-di(2-napthyl)]anthracen-2-yl]-1H-benzimidazole 1.7 g (4.9 mmol) of 5-bromo-1,2-diphenyl-1H-benzimidazole, 2.5 g (5.3 mmol) of 9,10-di(2-naphtyl)anthracene-2-boronic acid, and 0.11 g (0.097 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the completion of the reaction, the resultant was filtered, and the resultant solid was washed with water, methanol, and toluene to obtain 2.1 g of a greenish white solid (61% yield). Mass spectral analysis confirmed that the solid was a target product. The solid had an m/e of 698 with respect to a molecular weight of 698.27.

Synthesis Example 12

A Compound 3-3 was synthesized in the same manner as in the synthesis of the Compound 3-2 except that 9,10-di(1-naphthyl)anthracene-2-boronic acid was used instead of 9,10-di(2-naphtyl)anthracene-2-boronic acid. Mass spectral analysis confirmed that the compound was a target product. The compound had an m/e of 698 with respect to a molecular weight of 698.27.

Synthesis Example 13

A Compound 3-4 was synthesized in the same manner as in the synthesis of the Compound 3-2 except that 9,10-bis(3,5-diphenylphenyl)anthracene-boronic acid was used instead of 9,10-di(2-naphtyl)anthracene-2-boronic acid. Mass spectral analysis confirmed that the compound was a target product. The compound had an m/e of 902 with respect to a molecular weight of 902.37.

Synthesis Example 14

A Compound 3-5 was synthesized in the same manner as in the synthesis of the Compound 3-2 except that 9,10-bis(biphenyl-2-yl)anthracene-2-boronic acid was used instead of 9,10-di(2-naphtyl)anthracene-2-boronic acid in the step (4-b). Mass spectral analysis confirmed that the compound was a target product. The compound had an m/e of 750 with respect to a molecular weight of 750.30.

Synthesis Example 15

A Compound 3-9 was synthesized as described below.

(15-a) Synthesis of 5-(9,10-diphenylanthracen-2-yl)-1-methyl-2-phenyl-1H-benzimidazole 1.4 g (4.9 mmol) of 5-bromo-1-methyl-2-phenyl-1H-benzimidazole, 2.0 g (5.3 mmol) of 9,10-diphenylanthracene-2-boronic acid, and 0.11 g (0.097 mmol) of tetrakis(triphenylphosphine)palladium were dissolved into 20 mL of 1,2-dimethoxyethane. Then, 10 mL of a 2 M aqueous solution of sodium carbonate were added, and the whole was refluxed under heating for 8 hours in an argon atmosphere. After the completion of the reaction, the resultant was filtered, and the resultant solid was washed with water, methanol, and toluene to obtain 2.0 g of a greenish white solid (76% yield). Mass spectral analysis confirmed that the solid was a target product. The solid had an m/e of 536 with respect to a molecular weight of 536.23.

Synthesis Example 16

A Compound 3-46 was synthesized as described below.

(16-a) Synthesis of 9,10-di(2-naphthyl)-2-(2-phenyl-1H-benzimidazol-1-yl)anthracene 5.1 g (10 mmol) of 2-bromo-9,10-di(2-naphthyl)anthracene, 2.3 g (12 mmol) of 2-phenyl-1H-benzimidazole, 0.19 g (11.0 mmol) of copper iodide, and 3.6 g (2.0 mmol) of 9,10-phenanthroline were dissolved into a 2 M solution of cesium carbonate in dimethylformamide (DMF), and the whole was refluxed under heating for 48 hours in an argon atmosphere. After the completion of the reaction, the resultant was filtered. The filtrate was poured into 1 L of 10-mass % hydrochloric acid, and the whole was extracted with methylene chloride. An organic layer was taken out and dried with magnesium sulfate, and then the solvent was distilled off under reduced pressure. The resultant solid was purified by means of silica gel column chromatography to obtain 2.2 g of a pale yellow solid (35% yield). Mass spectral analysis confirmed that the solid was a target product. The solid had an m/e of 622 with respect to a molecular weight of 622.24.

Synthesis Example 17

A Compound 3-74 was synthesized in the same manner as in the synthesis of the Compound 3-9 except that 9,10-di(2-naphthyl)anthracene-2-boronic acid was used instead of 9,10-diphenylanthracene-2-boronic acid. Mass spectral analysis confirmed that the compound was a target product. The compound had an m/e of 636 with respect to a molecular weight of 636.26.

Synthesis Example 18

A Compound 3-75 was synthesized in the same manner as in the synthesis of the Compound 3-9 except that 9,10-di(1-naphthyl)anthracene-2-boronic acid was used instead of 9,10-diphenylanthracene-2-boronic acid. Mass spectral analysis confirmed that the compound was a target product. The compound had an m/e of 636 with respect to a molecular weight of 636.26.

Synthesis Example 19

A Compound 3-76 was synthesized in the same manner as in the synthesis of the Compound 3-9 except that 9,10-bis(biphenyl-2-yl)anthracene-2-boronic acid was used instead of 9,10-diphenylanthracene-2-boronic acid. Mass spectral analysis confirmed that the compound was a target product. The compound had an m/e of 688 with respect to a molecular weight of 688.29.

Synthesis Example 20

A Compound 3-77 was synthesized in the same manner as in the synthesis of the Compound 3-9 except that 9,10-bis(3, 5-diphenylphenyl)anthracene-2-boronic acid was used instead of 9,10-diphenylanthracene-2-boronic acid. Mass spectral analysis confirmed that the compound was a target product. The compound had an m/e of 840 with respect to a molecular weight of 840.35.

Synthesis Example 21

A Compound 4-2 was synthesized as described below.

(21-a) Synthesis of 2,6-bis(1,2-diphenyl-1H-benzimidazol-5-yl)-9,10-di(2-naphthyl)anthracene 2.0 g (3.4 mmol) of 2,6-dibromo-9,10-di(2-naphthyl)anthracene, 2.4 g (7.5 mmol) of 1,2-diphenyl-1H-benzimidazole-5-boronic acid, and 0.16 g (0.14 mmol) of tetrakis(triphenylphosphine)palladium were dissolved into 30 mL of 1,2-dimethoxyethane. Then, 15 mL of a 2 M aqueous solution of sodium carbonate were added, and the whole was refluxed under heating for 8 hours in an argon atmosphere. The resultant was stood to cool. After the completion of the reaction, the resultant was filtered, and the resultant solid was washed with water, methanol, and toluene to obtain 2.4 g of a greenish white crystal (73% yield). Mass spectral analysis confirmed that the crystal was a target product. The crystal had an m/e of 966 with respect to a molecular weight of 966.37.

Synthesis Example 22

A Compound 4-20 was synthesized as described below.

(22-a) Synthesis of 2,6-bis(2-phenyl-1H-benzimidazol-1-yl)-9,10-di(2-naphtyl)anthracene 5.9 g (10 mmol) of 2,6-dibromo-9,10-di(2-naphthyl)anthracene, 4.3 g (22 mmol) of 2-phenyl-1H-benzimidazole, 0.38 g (2.0 mmol) of copper iodide, and 7.2 g (4.0 mmol) of 9,10-phenanthroline were dissolved into a 2 M solution of cesium carbonate in dimethylformamide (DMF), and the whole was refluxed under heating for 48 hours in an argon atmosphere. After the completion of the reaction, the resultant was filtered. The filtrate was poured into 1 L of 10-mass % hydrochloric acid, and the whole was extracted with methylene chloride. An organic layer was taken out and dried with magnesium sulfate, and then the solvent was distilled off under reduced pressure. The resultant solid was purified by means of silica gel column chromatography to obtain 2.5 g of a pale yellow solid (31% yield). Mass spectral analysis confirmed that the solid was a target product. The solid had an m/e of 814 with respect to a molecular weight of 814.31.

Synthesis Example 23

A Compound 5-24 was synthesized as described below.

(23-a) Synthesis of 2-bromo-9,10-di(2-naphthyl)-6-(2-phenyl-1H-benzimidazol-1-yl)anthracene 5.9 g (10 mmol) of 2,6-dibromo-9,10-di(2-naphthyl)anthracene, 2.2 g (11 mmol) of 2-phenyl-1H-benzimidazole, 0.19 g (1.0 mmol) of copper iodide, and 3.6 g (2.0 mmol) of 9,10-phenanthroline were dissolved into a 2 M solution of cesium carbonate in dimethylformamide (DMF), and the whole was refluxed under heating for 48 hours in an argon atmosphere. After the completion of the reaction, the resultant was filtered. The filtrate was poured into 1 L of 10-mass % hydrochloric acid, and the whole was extracted with methyl-ene chloride. An organic layer was taken out and dried with magnesium sulfate, and then the solvent was distilled off under reduced pressure. The resultant solid was purified by means of silica gel column chromatography to obtain 2.5 g of a pale yellow solid (36% yield).

(23-b) Synthesis of 9,10-di(2-naphthyl)-2-(2-phenyl)-1H-benzimidazol-1-yl)-6-[4-(2-phenyl-1H-benzimidazol-yl)-phenyl]anthracene 2.5 g (3.6 mmol) of 2-bromo-9,10-di(2-naphthyl)-6-(2-phenyl-1H-benzimidazol-1-yl)anthracene, 1.4 g (4.3 mmol) of 4-(2-phenyl-1H-benzimidazol-1-yl)phenyl boronic acid, and 0.16 g (0.14 mmol) of tetrakis(triphenylphosphine)palladium were dissolved into 30 mL of 1,2-dimethoxyethane. Then, 15 mL of a 2 M aqueous solution of sodium carbonate were added, and the whole was refluxed under heating for 8 hours in an argon atmosphere. The resultant was stood to cool. After the completion of the reaction, the resultant was filtered, and the resultant solid was washed with water, methanol, and toluene to obtain 2.4 g of a greenish white crystal (76% yield). Mass spectral analysis confirmed that the crystal was a target product. The crystal had an m/e of 890 with respect to a molecular weight of 890.34.

Example 1

A glass substrate with an ITO transparent electrode measuring 25 mm long by 75 mm wide by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes. The glass substrate with a transparent electrode line after the cleaning was mounted on the substrate holder of a vacuum vapor deposition apparatus. At first, an N,N'-bis(N,N'-diphenyl-4-aminophenyl)-N,N-diphenyl-4,4'-diamino-1,1'-biphenyl film having a thickness of 60 nm (hereinafter, abbreviated as the "TPD232 film") was formed by means of resistive heating vapor deposition on the surface of the side on which the transparent electrode line was formed in such a manner that the transparent electrode would be covered with the film. The TPD232 film functions as a first hole-injecting layer (hole-transporting layer). Subsequent to the formation of the TPD232 film, a 4,4'-bis[N-(1-naphthyl)-N-phenylamino]biphenyl film having a thickness of 20 nm (hereinafter, abbreviated as the "NPD film") was formed by means of resistive heating vapor deposition on the TPD232 film. The NPD film functions as a second hole-injecting layer (hole-transporting layer). Furthermore, subsequent to the formation of the NPD film, 4',4"-bis(2,2-diphenylvinyl)-9,10-diphenylanthracene (hereinafter, abbreviated as "DPVDPAN") was formed into a film having a thickness of 40 nm by means of resistive heating vapor deposition on the NPD film. The DPVDPAN film functions as a light-emitting layer.

Then, subsequent to the formation of the DPVDPAN film, the Compound 1-41 was deposited from the vapor on the DPVDPAN film to form a Compound 1-41 film having a thickness of 10 nm. The compound 1-41 film functions as an electron-injecting layer. After that, Li (Li source: manufactured by SAES Getters) and the Compound 1-41 were subjected to binary vapor deposition to form a compound 1-41:Li film having a thickness of 10 nm as an electron-injecting layer (or a cathode) at film forming rates of 1.5 Å/sec:1 Å/min. Metal Al was deposited from the vapor on the compound 1-41:Li film to form a metal cathode having a thickness of 130 nm, with the result that an organic EL device was formed.

The emission luminance and current efficiency of the resultant organic EL device were measured with a predetermined direct voltage shown in Table 1 being applied to the device. Table 1 shows the results.

Examples 2 to 7

Similar organic EL devices were produced with the use of the Compounds shown in Table 1 instead of the Compound 1-41 in Example 1, and the devices were each subjected to similar measurement. Table 1 shows the results.

Comparative Example 1

A similar organic EL device was produced with the use of an aluminum complex of 8-hydroxyquinoline (Alq) represented by the following formula instead of the Compound 1-41 in Example 1, and the device was subjected to similar measurement. Table 1 shows the results.

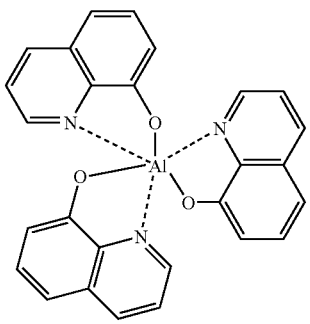

Comparative Example 2

A similar organic EL device was produced with the use of a Compound A described in U.S. Pat. No. 5,645,948 represented by the following formula instead of the Compound 1-41 in Example 1, and the device was subjected to similar measurement. Table 1 shows the results.

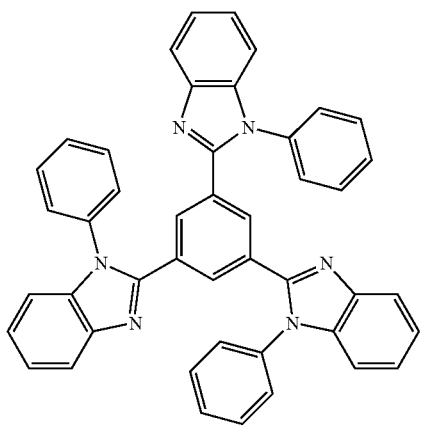

Comparative Example 3

A similar organic EL device was produced with the use of a Compound B described in WO 03/060956 A represented by the following formula instead of the Compound 1-41 in Example 1, and the device was subjected to similar measurement. Table 1 shows the results.

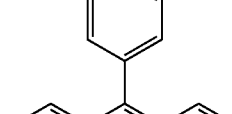

Comparative Example 4

A similar organic EL device was produced with the use of a Compound C described in JP 2002-038141 A represented by the following formula instead of the Compound 1-41 in Example 1.

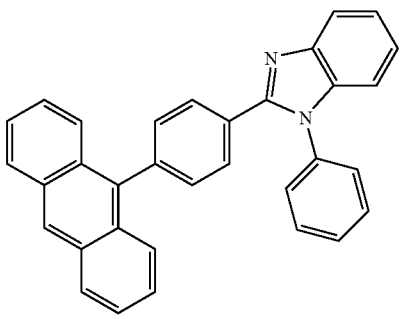

TABLE 1

| | Electron-injecting material | Voltage (V) | Current density (mA/cm2) | Luminance (nit) | Current efficiency (cd/A) |
|---|---|---|---|---|---|
| Example 1 | Compound 1-41 | 7.0 | 22 | 1466 | 6.7 |
| Example 2 | Compound 1-42 | 7.0 | 22 | 1452 | 6.6 |
| Example 3 | Compound 2-12 | 7.0 | 21 | 1365 | 6.5 |
| Example 4 | Compound 3-2 | 7.0 | 20 | 1282 | 6.4 |
| Example 5 | Compound3-9 | 7.0 | 26 | 1846 | 7.1 |
| Example 6 | Compound 4-2 | 7.0 | 20 | 1240 | 6.2 |
| Example 7 | Compound 5-24 | 7.0 | 21 | 1344 | 6.4 |
| Comparative example 1 | ALq | 7.0 | 13 | 500 | 3.8 |
| Comparative example 2 | Compound A | 7.0 | 7.4 | 185 | 2.5 |
| Comparative example 3 | Compound B | 7.0 | 15 | 624 | 4.1 |
| Comparative example 4 | Compound C | 7.0 | 15 | 600 | 4.0 |

As can be seen from the results shown in Table 1 above, the use of the derivative of heterocyclic compound having a nitrogen atom of the present invention as an electron-injecting layer enables a device having a high emission luminance and a high current efficiency to be produced. In particular, a device of each of the examples has an efficiency twice or more as high as that of an device of Comparative Example 1 or 2. In addition, a device of each of Comparative Examples 3 and 4 employs a compound similar to a compound used in each of the examples, but has a lower emission luminance and a lower current efficiency than those of a device of each of the examples. In contrast, the compounds used in the examples are different from each other in manner in which a benzimidazole portion and an anthracene nucleus bind to each other, so each of the compounds is observed to exert a significant effect. That is, electron-injecting property increases, a device can be driven at a reduced voltage, and the current efficiency of the device increases by 50% or more. Of those examples, in Example 5, the introduction of an alkyl group into a benzimidazole ring is found to be particularly effective in reducing a voltage and increasing the current efficiency.

Examples 8 to 16

Similar organic EL devices were produced with the use of the Compounds shown in Table 2 instead of the Compound 1-41 in Example 1, and the devices were each subjected to similar measurement. Table 2 shows the results.

TABLE 2

|  | Electron-injecting material | Voltage (V) | Current density (mA/cm2) | Luminance (nit) | Current efficiency (cd/A) |
|---|---|---|---|---|---|
| Example 8 | Compound 1-43 | 7.0 | 22 | 1,462 | 6.6 |
| Example 9 | Compound 1-44 | 7.0 | 23 | 1,450 | 6.3 |
| Example 10 | Compound 1-45 | 7.0 | 21 | 1,365 | 6.5 |
| Example 11 | Compound 3-3 | 7.0 | 20 | 1,246 | 6.2 |
| Example 12 | Compound 3-4 | 7.0 | 20 | 1,246 | 6.2 |
| Example 13 | Compound 3-5 | 7.0 | 20 | 1,286 | 6.4 |
| Example 14 | Compound 3-75 | 7.0 | 26 | 1,846 | 7.1 |
| Example 15 | Compound 3-76 | 7.0 | 27 | 1,912 | 7.1 |
| Example 16 | Compound 3-77 | 7.0 | 26 | 1,806 | 6.9 |

INDUSTRIAL APPLICABILITY

The derivative of heterocyclic compound having a nitrogen atom of the present invention qualifies as an electron-injecting/transporting material for an organic EL device and as an electron-injecting material for an electrophotographic photosensitive member. In addition, the derivative qualifies as an electron-injecting material for an organic semiconductor as well.

The invention claimed is:

1. A derivative of heterocyclic compound having a nitrogen atom represented by the following general formula (A-1) or (A-2):

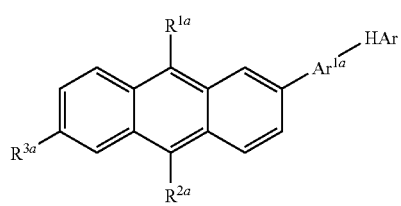
(A-1)

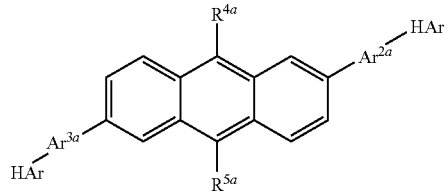
(A-2)

wherein $R^{1a}$ to $R^{5a}$ each represent a substituent, $Ar^{1a}$ to $Ar^{3a}$ each represent a single bond or a divalent connecting group, and HAr represents a group represented by the following general formula (A-3) or (A-4):

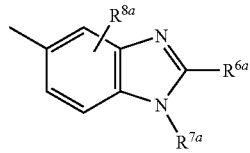
(A-3)

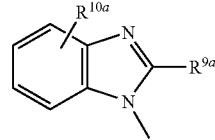
(A-4)

wherein $R^{6a}$ to $R^{10a}$ each represent a substituent, with the proviso that $R^{9a}$ does not include an anthracene moiety.

2. A derivative of heterocyclic compound having a nitrogen atom according to claim 1, which has the general formula (A-1) and is represented by the following general formula (1-I) or (1-II):

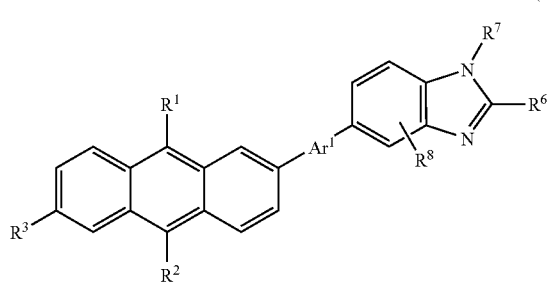
(1-I)

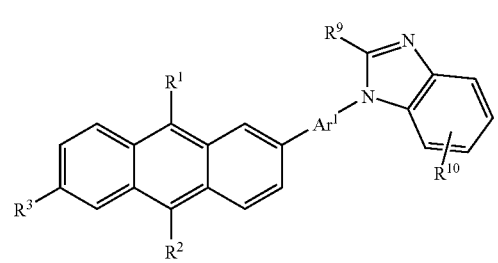
(1-II)

wherein $R^1$ and $R^2$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^1$ and $R^2$ cannot simultaneously represent hydrogen atoms; $R^3$ represents any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group, with the proviso that $R^9$ does not include an anthracene moiety; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; and $Ar^1$ represents a group selected from a substituted or unsubstituted arylene group, a substituted or unsubstituted heteroarylene group, and a substituted or unsubstituted divalent aliphatic hydrocarbon group.

3. A derivative of heterocyclic compound having a nitrogen atom according to claim 1, which has the general formula (A-2) and is represented by the following general formula (2-I) or (2-II):

group, and a substituted or unsubstituted heteroaryl group; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; and $Ar^2$ and $Ar^3$ each independently represent a group selected from a substituted or unsubstituted arylene group, a substituted or unsubstituted heteroarylene group, and a substituted or unsubstituted divalent aliphatic hydrocarbon group.

4. A derivative of heterocyclic compound having a nitrogen atom according to claim 1, which has the general formula (A-1) and is represented by the following general formula (3-I) or (3-II):

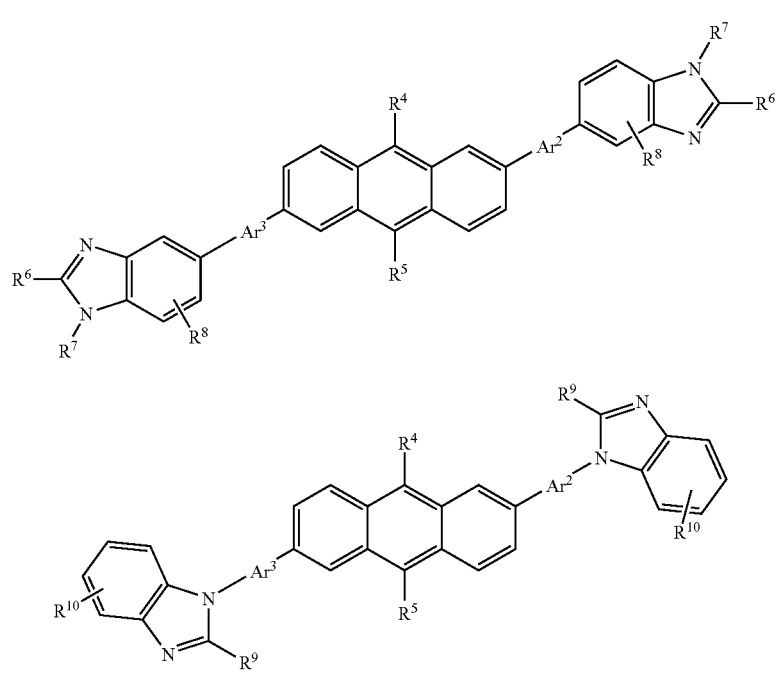

(2-I)

(2-II)

wherein $R^4$ and $R^5$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^4$ and $R^5$ cannot simultaneously represent hydrogen atoms; $R^6$ and $R^9$ each represent any one selected from a group consisting of a hydrogen atom, a halogen atom, a substituted or unsubstituted hydrocarbon group, a substituted or unsubstituted aryl

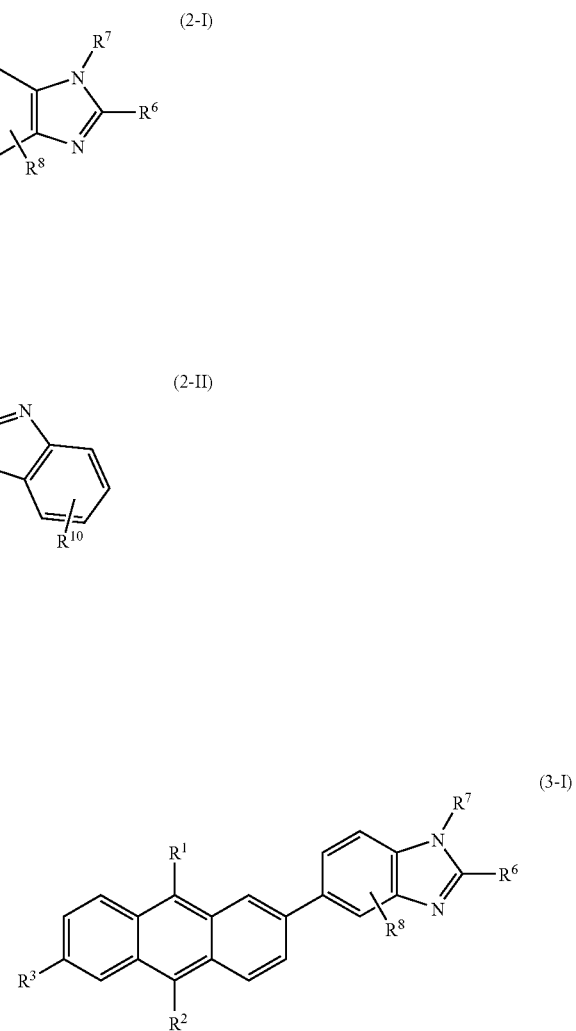

(3-I)

-continued (3-II)

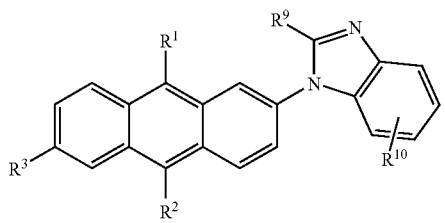

(4-II)

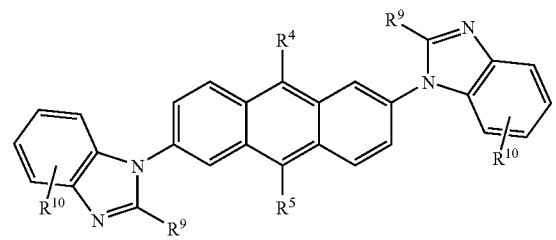

wherein $R^1$ and $R^2$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^1$ and $R^2$ cannot simultaneously represent hydrogen atoms; $R^3$ represents any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group, with the proviso that $R^9$ does not include an anthracene moiety; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group.

5. A derivative of heterocyclic compound having a nitrogen atom according to claim 1, which has the general formula (A-2) and is represented by the following general formula (4-I) or (4-II):

wherein $R^4$ and $R^5$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^4$ and $R^5$ cannot simultaneously represent hydrogen atoms; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group.

6. A derivative of heterocyclic compound having a nitrogen atom according to claim 1, which has the general formula (A-2) and is represented by the following general formula (5-I) or (5-II):

(5-I)

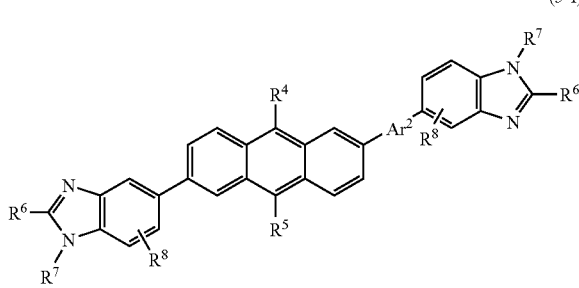

(4-I)

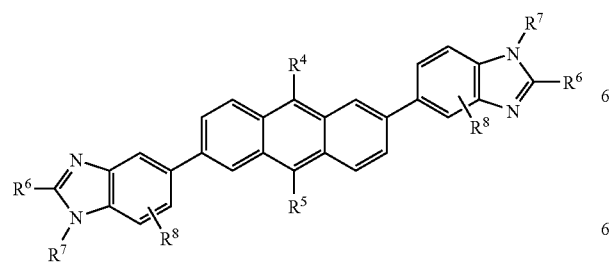

(5-II)

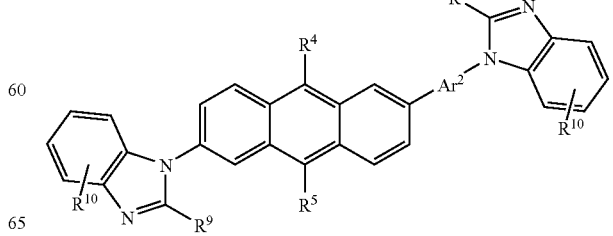

wherein $R^4$ and $R^5$ each independently represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; provided that $R^4$ and $R^5$ cannot simultaneously represent hydrogen atoms; $R^6$ and $R^9$ each represent any one selected from a group consisting of a hydrogen atom, a halogen atom, a substituted or unsubstituted aliphatic hydrocarbon group, a substituted or unsubstituted aryl group, and a substituted or unsubstituted heteroaryl group; $R^7$ represents any one selected from a group consisting of a hydrogen atom, a substituted or unsubstituted aliphatic hydrocarbon group, a substituted or unsubstituted aryl group, and a substituted or unsubstituted heteroaryl group; $R^8$ and $R^{10}$ each represent any one selected from a group consisting of a hydrogen atom, a halogen atom, a substituted or unsubstituted aliphatic hydrocarbon group, a substituted or unsubstituted alkoxy group, a substituted or unsubstituted aryl group, and a substituted or unsubstituted heteroaryl group; and $Ar^2$ represents a group selected from a substituted or unsubstituted arylene group, a substituted or unsubstituted heteroarylene group, and a substituted or unsubstituted divalent aliphatic hydrocarbon group.

7. A derivative of heterocyclic compound having a nitrogen atom according to claim 1, wherein HAr is represented by general formula (A-3) and wherein $R^{7a}$ represents a substituted or unsubstituted aliphatic hydrocarbon group, or $Ar^{1a}$ to $Ar^{3a}$ in the general formulae (A-1) and (A-2) each represent a substituted or unsubstituted divalent aliphatic hydrocarbon group.

8. A derivative of heterocyclic compound having a nitrogen atom according to claim 2, which has the general formula (1-I) and wherein $R^7$ represents a substituted or unsubstituted aliphatic hydrocarbon group, or $Ar^1$ represents a substituted or unsubstituted divalent aliphatic hydrocarbon group.

9. A derivative of heterocyclic compound having a nitrogen atom according to claim 2, which has the general formula (1-II) and wherein $Ar^1$ represents a substituted or unsubstituted divalent aliphatic hydrocarbon group.

10. An organic electroluminescence device comprising:
a cathode;
an anode; and
one or more organic thin-film layers sandwiched between the two electrodes and having at least a light-emitting layer, wherein at least one layer among the organic thin-film layers comprises the derivative of heterocyclic compound having a nitrogen atom according to claim 1.

11. An organic electroluminescence device according to claim 10, which comprises the derivative of heterocyclic compound having a nitrogen atom mainly in a light-emitting domain.

12. An organic electroluminescence device according to claim 10, which comprises the derivative of heterocyclic compound having a nitrogen atom mainly in a light-emitting layer.

13. An organic electroluminescence device according to claim 10, wherein:
the organic thin-film layer comprises at least one of an electron-injecting layer or an electron-transporting layer; and
the derivative of heterocyclic compound having a nitrogen atom comprises at least one of a material for the electron-injecting layer or a material for the electron-transporting layer.

14. An organic electroluminescence device according to claim 13, wherein at least one of the electron-injecting layer or the electron-transporting layer contains a reductive dopant.

15. An organic electroluminescence device according to claim 14, wherein the reductive dopant comprises one or more kinds of substances selected from the group consisting of an alkali metal, an alkali earth metal, a rare earth metal, an oxide of an alkali metal, a halide of an alkali metal, an oxide of an alkali earth metal, a halide of an alkali earth metal, an oxide of a rare earth metal, a halide of a rare earth metal, an organic complex of an alkali metal, an organic complex of an alkali earth metal, and an organic complex of a rare earth metal.

16. A derivative of heterocyclic compound having a nitrogen atom according to claim 3, which has the general formula (2-I) and wherein $R^7$ represents a substituted or unsubstituted aliphatic hydrocarbon group, or $Ar^2$ and $Ar^3$ each represent a substituted or unsubstituted divalent aliphatic hydrocarbon group.

17. A derivative of heterocyclic compound having a nitrogen atom according to claim 4, which has the general formula (3-I) and wherein $R^7$ represents a substituted or unsubstituted aliphatic hydrocarbon group.

18. A derivative of heterocyclic compound having a nitrogen atom according to claim 5, which has the general formula (4-I) and wherein $R^7$ represents a substituted or unsubstituted aliphatic hydrocarbon group.

19. A derivative of heterocyclic compound having a nitrogen atom according to claim 6, which has the general formula (5-I) and wherein $R^7$ represents a substituted or unsubstituted aliphatic hydrocarbon group, or $Ar^2$ represents a substituted or unsubstituted divalent aliphatic hydrocarbon group.

20. A derivative of heterocyclic compound having a nitrogen atom according to claim 3, which has the general formula (2-II) and wherein $Ar^2$ and $Ar^3$ each represent a substituted or unsubstituted divalent aliphatic hydrocarbon group.

21. A derivative of heterocyclic compound having a nitrogen atom according to claim 6, which has the general formula (5-II) and wherein $Ar^2$ represents a substituted or unsubstituted divalent aliphatic hydrocarbon group.

* * * * *